US012721833B2

(12) United States Patent
Law et al.

(10) Patent No.: US 12,721,833 B2
(45) **Date of Patent: *Sep. 1, 2026**

(54) SMALL MOLECULE ANTICANCER AGENTS, COMBINATIONS AND USES THEREOF

(71) Applicant: University of Florida Research Foundation, Incorporated, Gainesville, FL (US)

(72) Inventors: Brian Keith Law, Gainesville, FL (US); Ronald K. Castellano, Gainesville, FL (US); Stephan Jahn, Gainesville, FL (US); Elham Yaaghubi, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 903 days.

This patent is subject to a terminal disclaimer.

(21) Appl. No.: 17/912,477

(22) PCT Filed: Mar. 16, 2021

(86) PCT No.: PCT/US2021/022542

§ 371 (c)(1),
(2) Date: Sep. 16, 2022

(87) PCT Pub. No.: WO2021/188523

PCT Pub. Date: Sep. 23, 2021

(65) Prior Publication Data

US 2023/0122505 A1 Apr. 20, 2023

Related U.S. Application Data

(60) Provisional application No. 63/067,651, filed on Aug. 19, 2020, provisional application No. 62/990,544, filed on Mar. 17, 2020.

(51) Int. Cl.
*A61K 31/385* (2006.01)
*A61P 35/00* (2006.01)
*C07D 339/08* (2006.01)

(52) U.S. Cl.
CPC ............ *A61K 31/385* (2013.01); *A61P 35/00* (2018.01); *C07D 339/08* (2013.01)

(58) Field of Classification Search
CPC ...... A61K 31/385; A61P 35/00; C07D 339/08
See application file for complete search history.

(56) References Cited

U.S. PATENT DOCUMENTS 12,030,864 B2 * 7/2024 Law ........................ A61P 35/00
2011/0052586 A1 3/2011 Barraclough et al.
2012/0189543 A1 7/2012 Wang et al.
2013/0273574 A1 10/2013 Kidd et al.
2017/0240570 A1 8/2017 Jahn et al.
2024/0118281 A1 4/2024 Law et al.

FOREIGN PATENT DOCUMENTS

WO WO 2008/104606 A1 9/2008
WO WO 2011/103091 A1 8/2011
WO WO 2014/048865 A1 4/2014
WO WO 2018/156600 A1 8/2018
WO WO 2019/241644 A 12/2019
WO WO 2021/188523 A1 9/2021
WO WO 2022/150754 A1 7/2022

OTHER PUBLICATIONS

Bass, Journal of Organic Chemistry, vol. 45, Issue 4, 1980, 710-715 (Year: 1980).*

Meanwell, Journal of Medicinal Chemistry, 2018, 61, 5822-5880 (Year: 2018).*

Jach, American Journal of Cancer Research, Nov. 15, 2021; 11 (11): 5249-5262 (Year: 2021).*

Schraps Cancer Medicine, 2024, 13: e70407 (Year: 2024).*

Meanwell, J. Med. Chem., 2018, 61, 5822-5880 (Year: 2018).*

Invitation to Pay Additional Fees for App. No. PCT/US2021/022542 mailed May 19, 2021.

International Search Report and Written Opinion for App. No. PCT/US2021/022542 mailed Jul. 28, 2021.

International Preliminary Report on Patentability for App. No. PCT/US2021/022542 mailed Sep. 29, 2022.

Gray et al., Development of a fluorescent monoclonal antibody-based assay to measure the allosteric effects of synthetic peptides on self-oligomerization of AGR2 protein. Protein Sci. Sep. 2013;22(9):1266-78. doi: 10.1002/pro.2299. Epub Jul. 25, 2013.

Law et al., Inhibitors of ERp44, PDIA1, and AGR2 induce disulfide-mediated oligomerization of Death Receptors 4 and 5 and cancer cell death. Cancer Lett. May 28, 2022;534:215604. doi: 10.1016/j.canlet.2022.215604. Epub Mar. 2, 2022.

Anelli et al., Sequential steps and checkpoints in the early exocytic compartment during secretory IgM biogenesis. EMBO J. Oct. 3, 2007;26(19):4177-88. doi: 10.1038/sj.emboj.7601844. Epub Sep. 6, 2007.

Arumugam et al., New Blocking Antibodies against Novel AGR2-C4.4A Pathway Reduce Growth and Metastasis of Pancreatic Tumors and Increase Survival in Mice. Mol Cancer Ther. Apr. 2015;14(4):941-51. doi: 10.1158/1535-7163.MCT-14-0470. Epub Feb. 2, 2015.

Ashkenazi et al., Safety and antitumor activity of recombinant soluble Apo2 ligand. J Clin Invest. Jul. 1999;104(2):155-62. doi: 10.1172/JCI6926.

(Continued)

*Primary Examiner* — Andrew D Kosar
*Assistant Examiner* — Phillip Matthew Rzeczycki
(74) *Attorney, Agent, or Firm* — Wolf, Greenfield & Sacks, P.C.

(57) ABSTRACT

The invention relates to methods of treating cell proliferative disorders. The invention further relates to pharmaceutical compositions for treating cell proliferative disorders, especially cancer.

20 Claims, 15 Drawing Sheets

(56) References Cited

OTHER PUBLICATIONS

Barraclough et al., The metastasis-associated anterior gradient 2 protein is correlated with poor survival of breast cancer patients. Am J Pathol. Nov. 2009;175(5):1848-57. doi: 10.2353/ajpath.2009.090246. Epub Oct. 15, 2009.
Bertoli et al., Two conserved cysteine triads in human Erolalpha cooperate for efficient disulfide bond formation in the endoplasmic reticulum. J Biol Chem. Jul. 16, 2004;279(29):30047-52. doi: 10.1074/jbc.M403192200. Epub May 10, 2004.
Besse et al., A metabolic switch in proteasome inhibitor-resistant multiple myeloma ensures higher mitochondrial metabolism, protein folding and sphingomyelin synthesis. Haematologica. Sep. 2019;104(9):e415-e419. doi: 10.3324/haematol.2018.207704. Epub Feb. 21, 2019.
Bondi, van der Waals Volumes and Radii. J. Phys. Chem. 1964;68(3):441-51.
Brychtova et al., Anterior gradient 2 and mucin 4 expression mirrors tumor cell differentiation in pancreatic adenocarcinomas, but aberrant anterior gradient 2 expression predicts worse patient outcome in poorly differentiated tumors. Pancreas. Jan. 2014;43(1):75-81.
Cha et al., Crystal structure of TRAIL-DR5 complex identifies a critical role of the unique frame insertion in conferring recognition specificity. J Biol Chem. Oct. 6, 2000;275(40):31171-7. doi: 10.1074/jbc.M004414200.
Cho et al., Glioblastoma-derived epidermal growth factor receptor carboxyl-terminal deletion mutants are transforming and are sensitive to EGFR-directed therapies. Cancer Res. Dec. 15, 2011;71(24):7587-96. doi: 10.1158/0008-5472.CAN-11-0821. Epub Oct. 14, 2011.
Corsino et al., A novel class of cyclin-dependent kinase inhibitors identified by molecular docking act through a unique mechanism. J Biol Chem. Oct. 23, 2009;284(43):29945-55. doi: 10.1074/jbc.M109.055251. Epub Aug. 26, 2009.
Cortini et al., ERp44 and ERGIC-53 synergize in coupling efficiency and fidelity of IgM polymerization and secretion. Traffic. May 2010;11(5):651-9. doi: 10.1111/j.1600-0854.2010.01043.x.
Cortini et al., From antibodies to adiponectin: role of ERp44 in sizing and timing protein secretion. Diabetes Obes Metab. Oct. 2010;12 Suppl 2:39-47. doi: 10.1111/j.1463-1326.2010.01272.x.
Costero et al., Crown ethers derived from cyclohexane. Influence of their stereohemistry in complexation and transport. Tetrahedron. 2002;58:6729-34.
De Ruijter et al., Characteristics of triple-negative breast cancer. J Cancer Res Clin Oncol. Feb. 2011;137(2):183-92. doi: 10.1007/s00432-010-0957-x. Epub Nov. 11, 2010.
Derose et al., Patient-derived models of human breast cancer: protocols for in vitro and in vivo applications in tumor biology and translational medicine. Curr Protoc Pharmacol. Mar. 2013;Chapter 14:Unit14.23. doi: 10.1002/0471141755.ph1423s60. Author manuscript, 52 pages.
Derose et al., Tumor grafts derived from women with breast cancer authentically reflect tumor pathology, growth, metastasis and disease outcomes. Nat Med. Oct. 23, 2011;17(11):1514-20. doi: 10.1038/nm.2454. Author manuscript, 21 pages.
Desantis et al., Breast cancer statistics, 2019. CA Cancer J Clin. Nov. 2019;69(6):438-451. doi: 10.3322/caac.21583. Epub Oct. 2, 2019.
Di Maro et al., Anterior gradient protein 2 promotes survival, migration and invasion of papillary thyroid carcinoma cells. Mol Cancer. Jun. 30, 2014;13:160.
Dong et al., Epidermal growth factor receptor (EGFR) signaling requires a specific endoplasmic reticulum thioredoxin for the post-translational control of receptor presentation to the cell surface. J Biol Chem. Mar. 27, 2015;290(13):8016-27. doi: 10.1074/jbc.M114.623207. Epub Feb. 9, 2015.
Dumartin et al., ER stress protein AGR2 precedes and is involved in the regulation of pancreatic cancer initiation. Oncogene. Jun. 1, 2017;36(22):3094-3103. doi: 10.1038/onc.2016.459. Epub Dec. 12, 2016.
Eriksson et al., Identification of PDI Substrates by Mechanism-Based Kinetic Trapping. Methods Mol Biol. 2019;1967:165-182. doi: 10.1007/978-1-4939-9187-7_10.
Ferreira et al., Disulfide bond disrupting agents activate the unfolded protein response in EGFR- and HER2-positive breast tumor cells. Oncotarget. Apr. 25, 2017;8(17):28971-28989. doi: 10.18632/oncotarget.15952.
Ferreira et al., Novel agents that downregulate EGFR, HER2, and HER3 in parallel. Oncotarget. Apr. 30, 2015;6(12):10445-59. doi: 10.18632/oncotarget.3398.
Fraldi et al., Multistep, sequential control of the trafficking and function of the multiple sulfatase deficiency gene product, SUMF1 by PDI, ERGIC-53 and ERp44. Hum Mol Genet. Sep. 1, 2008;17(17):2610-21. doi: 10.1093/hmg/ddn161. Epub May 28, 2008.
Frand et al., The ERO1 gene of yeast is required for oxidation of protein dithiols in the endoplasmic reticulum. Mol Cell. Jan. 1998;1(2):161-70. doi: 10.1016/s1097-2765(00)80017-9.
Fritzsche et al., Prognostic relevance of AGR2 expression in breast cancer. Clin Cancer Res. Mar. 15, 2006;12(6):1728-34. doi: 10.1158/1078-0432.CCR-05-2057.
Galligan et al., The human protein disulfide isomerase gene family. Hum Genomics. Jul. 5, 2012;6(1):6. doi: 10.1186/1479-7364-6-6.
Ghilardi et al., Anticancer Agents Derived from Cyclic Thiosulfonates: Structure-Reactivity and Structure-Activity Relationships. ChemMedChem. Jul. 19, 2022;17(14):e202200165. doi: 10.1002/cmdc.202200165. Epub May 23, 2022.
Ghilardi et al., Structure-reactivity studies involving thiosulfonate compounds capable of selectively killing HER2+ and EGFR+ breast cancer cells. American Chemical Society Fall 2020 Virtual Meeting. Aug. 2020. Poster and Abstract.
Gillis et al., Applications of Fluorine in Medicinal Chemistry. J Med Chem. Nov. 12, 2015;58(21):8315-59. doi: 10.1021/acs.jmedchem.5b00258. Epub Jul. 22, 2015.
Guo et al., A humanized monoclonal antibody targeting secreted anterior gradient 2 effectively inhibits the xenograft tumor growth. Biochem Biophys Res Commun. Jun. 17, 2016;475(1):57-63. doi: 10.1016/j.bbrc.2016.05.033. Epub May 7, 2016.
Guo et al., Tumor-secreted anterior gradient-2 binds to VEGF and FGF2 and enhances their activities by promoting their homodimerization. Oncogene. Sep. 7, 2017;36(36):5098-5109. doi: 10.1038/onc.2017.132. Epub May 8, 2017.
Gupta et al., AGR2 gene function requires a unique endoplasmic reticulum localization motif. J Biol Chem. Feb. 10, 2012;287(7):4773-82. doi: 10.1074/jbc.M111.301531. Epub Dec. 19, 2011.
Hampe et al., Regulation and Quality Control of Adiponectin Assembly by Endoplasmic Reticulum Chaperone ERp44. J Biol Chem. Jul. 17, 2015;290(29):18111-18123. doi: 10.1074/jbc.M115.663088. Epub Jun. 9, 2015.
Hisatsune et al., ERp44 Exerts Redox-Dependent Control of Blood Pressure at the ER. Mol Cell. Jun. 18, 2015;58(6):1015-27. doi: 10.1016/j.molcel.2015.04.008. Epub May 7, 2015.
Hu et al., Knockdown of AGR2 induces cellular senescence in prostate cancer cells. Carcinogenesis. Jun. 2012;33(6):1178-86. doi: 10.1093/carcin/bgs141. Epub Mar. 31, 2012.
Innes et al., Significance of the metastasis-inducing protein AGR2 for outcome in hormonally treated breast cancer patients. Br J Cancer. Apr. 10, 2006;94(7):1057-65. doi: 10.1038/sj.bjc.6603065.
Jia et al., Pro-metastatic activity of AGR2 interrupts angiogenesis target bevacizumab efficiency via direct interaction with VEGFA and activation of NF-κB pathway. Biochim Biophys Acta Mol Basis Dis. May 2018;1864(5 Pt A):1622-1633. doi: 10.1016/j.bbadis.2018.01.021. Epub Feb. 1, 2018.
Keller et al., Empirical statistical model to estimate the accuracy of peptide identifications made by MS/MS and database search. Anal Chem. Oct. 15, 2002;74(20):5383-92. doi: 10.1021/ac025747h.
Koller et al., Zinc-mediated formation of trifluoromethyl ethers from alcohols and hypervalent iodine trifluoromethylation reagents. Angew Chem Int Ed Engl. 2009;48(24):4332-6.
Kubyshkin et al., Amide rotation trajectories probed by symmetry. Organic & Biomolecular Chemistry. Jul. 2017;15(32):6764-72.

(56) References Cited

OTHER PUBLICATIONS

Kubyshkin et al., Energetic contribution to both acidity and conformational stability in peptide models. New Journal of Chemisty. Mar. 2016;40(6):5209-20.
Laboissiere et al., The essential function of protein-disulfide isomerase is to unscramble non-native disulfide bonds. J Biol Chem. Nov. 24, 1995;270(47):28006-9. doi: 10.1074/jbc.270.47.28006.
Lacambra et al., Anterior Gradient 2 is a Poor Outcome Indicator in Luminal Breast Cancer. Ann Surg Oncol. Oct. 2015;22(11):3489-96. doi: 10.1245/s10434-015-4420-8. Epub Feb. 7, 2015.
Law et al., CUB domain-containing protein 1 and the epidermal growth factor receptor cooperate to induce cell detachment. Breast Cancer Res. Aug. 5, 2016;18(1):80. doi: 10.1186/s13058-016-0741-1.
Law et al., Farnesyltransferase inhibitor induces rapid growth arrest and blocks p70s6k activation by multiple stimuli. J Biol Chem. Apr. 14, 2000;275(15):10796-801. doi: 10.1074/jbc.275.15.10796.
Law et al., Glucocorticoids and histone deacetylase inhibitors cooperate to block the invasiveness of basal-like breast cancer cells through novel mechanisms. Oncogene. Mar. 7, 2013;32(10):1316-29. doi: 10.1038/onc.2012.138. Epub Apr. 30, 2012. Author manuscript, 25 pages.
Law et al., Rapamycin potentiates transforming growth factor beta-induced growth arrest in nontransformed, oncogene-transformed, and human cancer cells. Mol Cell Biol. Dec. 2002;22(23):8184-98. doi: 10.1128/MCB.22.23.8184-8198.2002.
Law et al., Repurposing Tranexamic Acid as an Anticancer Agent. bioRxiv. Oct. 17, 2021; doi: 10.1101/2021.10.17.464714. https://www.biorxiv.org/content/10.1101/2021.10.17.464714v1, 27 pages.
Law et al., Repurposing Tranexamic Acid as an Anticancer Agent. Front Pharmacol. Jan. 13, 2022;12:792600.
Law et al., Salicylate-induced growth arrest is associated with inhibition of p70s6k and down-regulation of c-myc, cyclin D1, cyclin A, and proliferating cell nuclear antigen. J Biol Chem. Dec. 8, 2000;275(49):38261-7. doi: 10.1074/jbc.M005545200.
Lemmon et al., Cell signaling by receptor tyrosine kinases. Cell. Jun. 25, 2010;141(7):1117-34. doi: 10.1016/j.cell.2010.06.011.
Liu et al., AGR2, a unique tumor-associated antigen, is a promising candidate for antibody targeting. Oncotarget. Jul. 2, 2019;10(42):4276-4289. doi: 10.18632/oncotarget.26945.
Liu et al., EGFR expression correlates with decreased disease-free survival in triple-negative breast cancer: a retrospective analysis based on a tissue microarray. Med Oncol. Jun. 2012;29(2):401-5. doi: 10.1007/s12032-011-9827-x. Epub Jan. 25, 2011.
Liu et al., Human homologue of cement gland protein, a novel metastasis inducer associated with breast carcinomas. Cancer Res. May 1, 2005;65(9):3796-805.
Liu et al., Silver-Mediated Oxidative Trifluoromethylation of Alcohols to Alkyl Trifluoromethyl Ethers. Org Lett. Oct. 16, 2015;17(20):5048-51. doi: 10.1021/acs.orglett.5b02522. Epub Sep. 29, 2015.
Long et al., Peroxisome proliferator-activated receptor-gamma increases adiponectin secretion via transcriptional repression of endoplasmic reticulum chaperone protein ERp44. Endocrinology. Jul. 2010;151(7):3195-203. doi: 10.1210/en.2009-1501. Epub May 19, 2010.
Narumi et al., Anterior gradient 2 is correlated with EGFR mutation in lung adenocarcinoma tissues. Int J Biol Markers. May 26, 2015;30(2):e234-42. doi: 10.5301/jbm.5000131.
Negi et al., Anterior Gradient-2 monoclonal antibody inhibits lung cancer growth and metastasis by upregulating p53 pathway and without exerting any toxicological effects: A preclinical study. Cancer Lett. May 1, 2019;449:125-134. doi: 10.1016/j.canlet.2019.01.025. Epub Jan. 25, 2019.
Nesvizhskii et al., A statistical model for identifying proteins by tandem mass spectrometry. Anal Chem. Sep. 1, 2003;75(17):4646-58. doi: 10.1021/ac0341261.
Otsu et al., Dynamic retention of Erolalpha and Erolbeta in the endoplasmic reticulum by interactions with PDI and ERp44. Antioxid Redox Signal. Mar.-Apr. 2006;8(3-4):274-82. doi: 10.1089/ars.2006.8.274.
Pan et al., Higher-Order Clustering of the Transmembrane Anchor of DR5 Drives Signaling. Cell. Mar. 7, 2019;176(6): 1477-1489.e14. doi: 10.1016/j.cell.2019.02.001. Epub Feb. 28, 2019.
Park et al., Metabolism of fluorine-containing drugs. Annu Rev Pharmacol Toxicol. 2001;41:443-70. doi: 10.1146/annurev.pharmtox.41.1.443.
Park et al., The protein disulfide isomerase AGR2 is essential for production of intestinal mucus. Proc Natl Acad Sci U S A. Apr. 28, 2009;106(17):6950-5. doi: 10.1073/pnas.0808722106. Epub Apr. 9, 2009.
Pollard et al., Ero1p: a novel and ubiquitous protein with an essential role in oxidative protein folding in the endoplasmic reticulum. Mol Cell. Jan. 1998;1(2):171-82. doi: 10.1016/s1097-2765(00)80018-0.
Rieger et al., APO2 ligand: a novel lethal weapon against malignant glioma? FEBS Lett. May 1, 1998;427(1):124-8. doi: 10.1016/s0014-5793(98)00409-8.
Rodriguez Sarmiento et al., Chemoenzymatic preparation of non-racemic N-Boc-pyrrolidine-3,4-dicarboxylic acid 3-ethyl esters and their 4-hydroxymethyl derivatives. Tetrahedron: Asymmetry. Jun. 6, 2003;14(11):1547-51.
Sannino et al., Progressive quality control of secretory proteins in the early secretory compartment by ERp44. J Cell Sci. Oct. 1, 2014;127(Pt 19):4260-9. doi: 10.1242/jcs.153239. Epub Aug. 5, 2014.
Schroeder et al., AGR2 is induced in asthma and promotes allergen-induced mucin overproduction. Am J Respir Cell Mol Biol. Aug. 2012;47(2):178-85. doi: 10.1165/rcmb.2011-0421OC. Epub Mar. 8, 2012.
Shergalis et al., Role of the ERO1-PDI interaction in oxidative protein folding and disease. Pharmacol Ther. Jun. 2020;210:107525. doi: 10.1016/j.pharmthera.2020.107525. Epub Mar. 20, 2020. Author manuscript, 40 pages.
Stockhausen et al., Maintenance of EGFR and EGFRvIII expressions in an in vivo and in vitro model of human glioblastoma multiforme. Exp Cell Res. Jul. 1, 2011;317(11):1513-26. doi: 10.1016/j.yexcr.2011.04.001. Epub Apr. 15, 2011.
Stojak et al., Protein Disulphide Isomerase A1 Is Involved in the Regulation of Breast Cancer Cell Adhesion and Transmigration via Lung Microvascular Endothelial Cells. Cancers (Basel). Oct. 2, 2020;12(10):2850. doi: 10.3390/cancers12102850.
Stopa et al., Kinetic-based trapping by intervening sequence variants of the active sites of protein-disulfide isomerase identifies platelet protein substrates. J Biol Chem. Jun. 2, 2017;292(22):9063-9074. doi: 10.1074/jbc.M116.771832. Epub Mar. 31, 2017.
Tempio et al., The pivotal role of ERp44 in patrolling protein secretion. J Cell Sci. Nov. 10, 2020;133(21):jcs240366. doi: 10.1242/jcs.240366.
Thapa et al., TRAIL therapy and prospective developments for cancer treatment. J Control Release. Oct. 10, 2020;326:335-349. doi: 10.1016/j.jconrel.2020.07.013. Epub Jul. 17, 2020.
Tomoshige et al., An EGFTOMR ligand promotes EGFR-mutant but not KRAS-mutant lung cancer in vivo. Oncogene. Jul. 2018;37(28):3894-3908. doi: 10.1038/s41388-018-0240-1. Epub Apr. 17, 2018.
Toyama et al., Frequently increased epidermal growth factor receptor (EGFR) copy numbers and decreased BRCA1 mRNA expression in Japanese triple-negative breast cancers. BMC Cancer. Oct. 25, 2008;8:309. doi: 10.1186/1471-2407-8-309.
Wang et al., A novel proteotoxic combination therapy for EGFR+ and HER2+ cancers. Oncogene. May 2019;38(22):4264-4282. doi: 10.1038/s41388-019-0717-6. Epub Feb. 4, 2019.
Wang et al., Disulfide bond-disrupting agents activate the tumor necrosis family-related apoptosis-inducing ligand/death receptor 5 pathway. Cell Death Discov. Dec. 10, 2019;5:153. doi: 10.1038/s41420-019-0228-9.

(56) References Cited

OTHER PUBLICATIONS

Wang et al., Fluorine in pharmaceutical industry: fluorine-containing drugs introduced to the market in the last decade (2001-2011). Chem Rev. Feb. 26, 2014;114(4):2432-506. doi: 10.1021/cr4002879. Epub Dec. 3, 2013.
Wang et al., Mechanistic Elucidation of the Antitumor Properties of a Novel Death Receptor 5 Activator. bioRxiv. Jul. 14, 2019. doi: https://doi.org/10.1101/700906.
Wang et al., Secretion of the adipocyte-specific secretory protein adiponectin critically depends on thiol-mediated protein retention. Mol Cell Biol. May 2007;27(10):3716-31. doi: 10.1128/MCB.00931-06. Epub Mar. 12, 2007.
Wang et al., The adenocarcinoma-associated antigen, AGR2, promotes tumor growth, cell migration, and cellular transformation. Cancer Res. Jan. 15, 2008;68(2):492-7. doi: 10.1158/0008-5472.CAN-07-2930.
Wiley et al., Identification and characterization of a new member of the TNF family that induces apoptosis. Immunity. Dec. 1995;3(6):673-82. doi: 10.1016/1074-7613(95)90057-8.
Wolf, New insights into thiol-mediated regulation of adiponectin secretion. Nutr Rev. Nov. 2008;66(11):642-5. doi: 10.1111/j.1753-4887.2008.00115.x.
Xu et al., Inhibition of protein disulfide isomerase in glioblastoma causes marked downregulation of DNA repair and DNA damage response genes. Theranostics. Apr. 12, 2019;9(8):2282-2298. doi: 10.7150/thno.30621.
Yaaghubi, Cyclic Thiosulfonates (DDAS) as Novel Anticancer Therapeutics against EGFR+ and HER2+ Tumors. University of Florida Dissertation. Jan. 2021.
Yaaghubi, Optimizing cyclic thiosulfonates, DDAs, as potent anti-cancer agents against HER2+ and EGFR+ breast cancer cells. American Chemical Society Fall 2020 Virtual Meeting. Aug. 2020. Presentation and Abstract.
Yang et al., Crystal Structure of the ERp44-Peroxiredoxin 4 Complex Reveals the Molecular Mechanisms of Thiol-Mediated Protein Retention. Structure. Oct. 4, 2016;24(10):1755-1765. doi: 10.1016/j.str.2016.08.002. Epub Sep. 15, 2016.
Zamai et al., Natural killer (NK) cell-mediated cytotoxicity: differential use of TRAIL and Fas ligand by immature and mature primary human NK cells. J Exp Med. Dec. 21, 1998;188(12):2375-80. doi: 10.1084/jem.188.12.2375.
Zhang et al., AGR2, an androgen-inducible secretory protein overexpressed in prostate cancer. Genes Chromosomes Cancer. Jul. 2005;43(3):249-59. doi: 10.1002/gcc.20188.

* cited by examiner

TcyDTDO

DMtcyDTDO

Pancreatic PDX tumors treated with vehicle for 4 days

SMALL MOLECULE ANTICANCER AGENTS, COMBINATIONS AND USES THEREOF

RELATED APPLICATIONS

This application is a national stage filing under 35 U.S.C. § 371 of International Patent Application Serial No. PCT/US2021/022542, filed Mar. 16, 2021, which claims priority under 35 U.S.C. § 119 (e) to U.S. Provisional Application, U.S. Ser. No. 62/990,544, filed on Mar. 17, 2020, and U.S. Provisional Application, U.S. Ser. No. 63/067,651, filed on Aug. 19, 2020, the contents of each are incorporated herein by reference in their entireties.

GOVERNMENT SUPPORT

The invention was made with government support under Grant No. R21 CA252400 awarded by the National Institutes of Health. The government has certain rights in the invention.

BACKGROUND OF THE INVENTION

AGR2 is a protein disulfide isomerase (PDI) localized predominantly to the endoplasmic reticulum (ER) of cells that functions as an oncogene and has been implicated in breast, pancreatic, prostate, lung and several other human cancers [1-9], and AGR2 expression is associated with metastasis [1, 10-12]. Although AGR2-specific antibodies are under development for inhibiting the functions of AGR2 [12-14], therapeutics are not available for blocking the intracellular functions of AGR2 in protein folding. AGR2 within the ER is required to facilitate the proper disulfide bonding, cell surface presentation, and function of the Epidermal Growth factor Receptor (EGFR) [15-17], which plays a key role in the development and progression of multiple human cancers. EGFR shares its disulfide-bonded extracellular domains with family members HER2 and HER3, which also play important roles in human cancer. Inhibition of AGR2 is expected to prevent the production of EGFR, HER2, and HER3 and the survival of cancer cells that are dependent on these oncoproteins.

The PDI catalytic activity of AGR2 is mediated by its thioredoxin-like repeat, which contains the single active site Cysteine residue, Cys81, which is the only Cys residue in AGR2. Disulfide bond disrupting agents (DDAs) are thiol-reactive compounds that have strong activity against human breast tumors growing in rodent models [18-22]. Recent results indicate that genetic inactivation of AGR2 produces the same anticancer responses as the DDAs, and DDAs form covalent adducts with AGR2. Molecular docking studies of an AGR2 surface pocket adjacent to Cys81 led to the identification of NSC322072 as a second chemical class of novel AGR2 inhibitors, and competition experiments show that NSC322072 and DDAs bind to the same site on AGR2.

Herein we describe the compounds of any of the formulae herein and their use in treating various diseases and disorders (e.g., breast cancer, pancreatic cancer).

SUMMARY OF THE INVENTION

In one aspect, the invention provides a compound of Formula I, or salt, solvate, hydrate or prodrug thereof:

Formula I

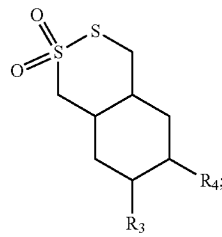

wherein, (i) $R_3$ is halo or haloalkoxy; and $R_4$ is halo or haloalkoxy; or (ii) $R_3$ is H or $C_1$-$C_6$ alkoxy; and $R_4$ is halo or haloalkoxy; or (iii) $R_3$ is halo or haloalkoxy; and $R_4$ is H or $C_1$-$C_6$ alkoxy.

In another aspect, the compound of Formula (I), or salt, solvate, hydrate or prodrug thereof, is according to Formula (II):

Formula II

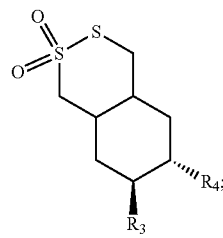

or salt, solvate, hydrate or prodrug thereof.

In another aspect, the compound of Formula (I), or salt, solvate, hydrate or prodrug thereof, is according to Formula (III):

Formula III

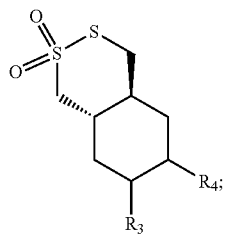

or salt, solvate, hydrate or prodrug thereof.

In another aspect, the compound of Formula (I), or salt, solvate, hydrate or prodrug thereof, is according to any of Formula (IV-XI):

IV

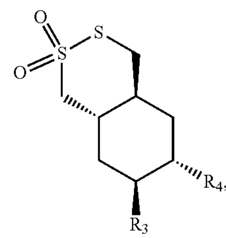

-continued

V

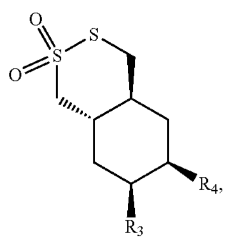

VI

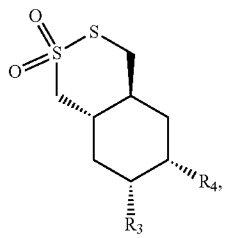

VII

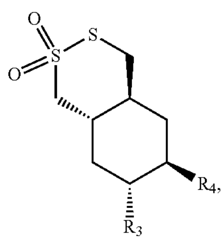

VIII

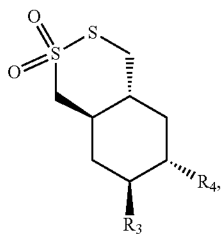

IX

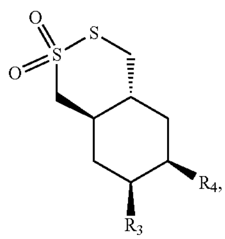

X

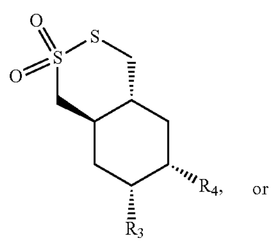

or

-continued

XI

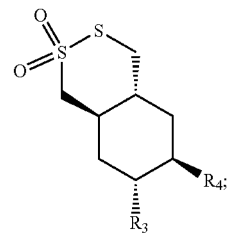

or salt, solvate, hydrate or prodrug thereof.

In another aspect, the invention provides a pharmaceutical composition comprising a compound of a compound of any one of the formulae herein (e.g., any of Formulae I-XI), or salt, solvate, hydrate or prodrug thereof, and a pharmaceutically acceptable carrier. In another aspect, the pharmaceutical composition comprises an additional agent.

In one aspect, the invention provides a method of treating a subject suffering from or susceptible to a cell proliferative disorder. The method includes administering to a subject in need thereof a therapeutically effective amount of a compound of any of the formulae herein (e.g., a compound of any one of Formulae I-XI), or salt, solvate, hydrate or prodrug thereof:

Formula I

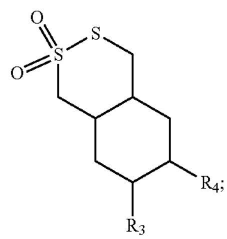

wherein, (iv) $R_3$ is halo or haloalkoxy; and $R_4$ is halo or haloalkoxy; or (v) $R_3$ is H or $C_1$-$C_6$ alkoxy; and $R_4$ is halo or haloalkoxy; or (vi) $R_3$ is halo or haloalkoxy; and $R_4$ is H or $C_1$-$C_6$ alkoxy.

In another aspect, the cell proliferative disorder is cancer. In a further aspect, the cancer is ARG2 mediated. In a further aspect, the cancer is breast cancer. In a further aspect, the cancer is pancreatic cancer. In a further aspect, the breast cancer is HER2-positive breast cancer. In another aspect, the breast cancer is mediated by HER2, HER3, and/or EGFR.

In another aspect, the invention provides a method of inhibiting cancer cell metastasis. The method includes administering to a subject in need thereof a therapeutically effective amount of a compound of any of the formulae herein (e.g., a compound of any one of Formulae I-XI), or salt, solvate, hydrate or prodrug thereof:

Formula I

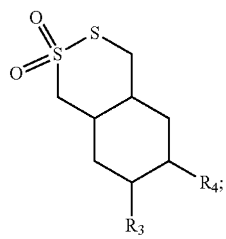

wherein, (i) $R_3$ is halo or haloalkoxy; and $R_4$ is halo or haloalkoxy; or (ii) $R_3$ is H or $C_1$-$C_6$ alkoxy; and $R_4$ is halo or haloalkoxy; or (iii) $R_3$ is halo or haloalkoxy; and $R_4$ is H or $C_1$-$C_6$ alkoxy.

In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR. In another aspect, the method includes administering to a subject in need thereof a therapeutically effective amount of a compound of any of the formulae herein (e.g., Formulae I-XI), or salt, solvate, hydrate or prodrug thereof. In another aspect, the cell is in vitro. In another aspect, the cell is in a subject.

In another aspect, the invention provides a kit for treating a cell proliferative disorder in a subject. The kit includes a compound of any of the formulae herein (e.g., Formulae I-XI), or salt, solvate, hydrate or prodrug thereof.

In one aspect, the kit comprises a compound of Formula I (e.g., Formulae II-XI), or salt, solvate, hydrate or prodrug thereof:

Formula I

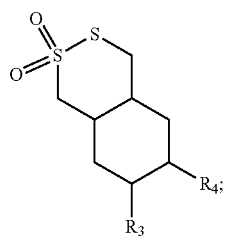

wherein, (i) $R_3$ is halo or haloalkoxy; and $R_4$ is halo or haloalkoxy; or (ii) $R_3$ is H or $C_1$-$C_6$ alkoxy; and $R_4$ is halo or haloalkoxy; or (iii) $R_3$ is halo or haloalkoxy; and $R_4$ is H or $C_1$-$C_6$ alkoxy; and instructions for use.

In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer.

Other aspects and embodiments of the invention are disclosed infra.

BRIEF DESCRIPTION OF THE DRAWINGS

The present invention is further described below with reference to the following non-limiting examples and with reference to the following figures, in which.

DETAILED DESCRIPTION OF THE INVENTION

1. Definitions

Figure 1A:
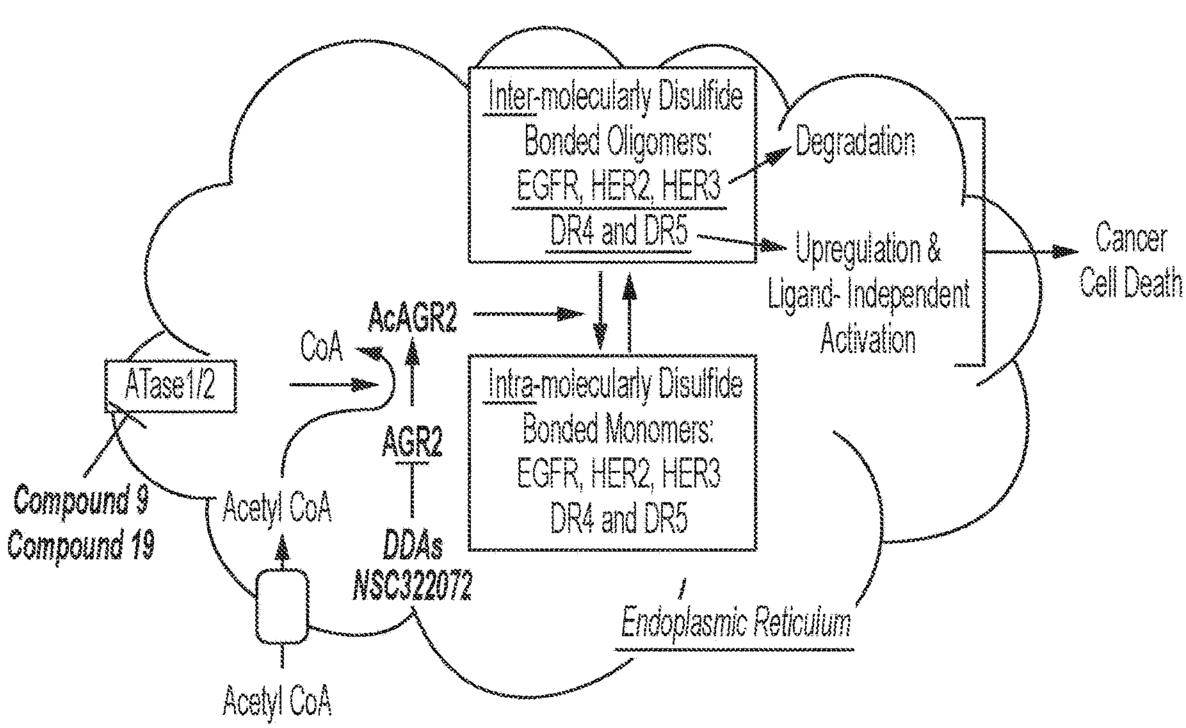
FIG. 1 depicts a model for Disulfide bond disrupting agents (DDA) mechanism of action and DDA structures. A. DDAs inhibit the PDI activity of AGR2. AGR2 activity is controlled by the endoplasmic reticulum acetyltransferases 1 and 2 (ATase 1/2). ATase 1/2 inhibition blocks acetylation-dependent activation of the PDI AGR2, resulting in disulfide bond-dependent oligomerization of EGFR (HER1), HER2, HER3, DR4, and DR5. Oligomerization of HER1-3 causes their degradation, while oligomerization of DR4/5 increases their stimulation of Caspase 8/3-dependent cell death. DDA actions are mimicked by established ATase 1/2 inhibitors, Compounds 9 and 19. B. Chemical structures of DDA TcyDTDO, a compound with established in vivo anticancer activity, and DMtcyDTDO, a DDA twice as potent as TcyDTDO. C. Decreased production of AGR2 mimics the effects of DDAs, including disulfide bond-mediated oligomerization of EGFR and DR5, and activation of Caspase 8 (CC8), leading to cancer cell death. D. Incubation of a biotinylated DDA derivative with AGR2 results in biotin-DDA attachment to AGR2. Labeling is not observed for the disulfide bonded dimeric form of AGR2, indicating that DDAs react with the AGR2 active site Cysteine, Cys81, which is the only Cysteine residue in the AGR2 protein.
Figure 1B:
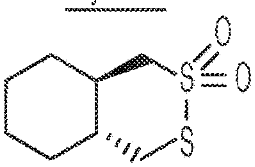
Figure 1B:
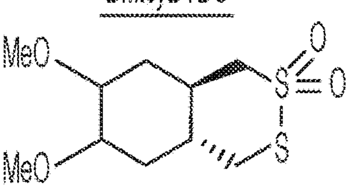
Figure 1C:
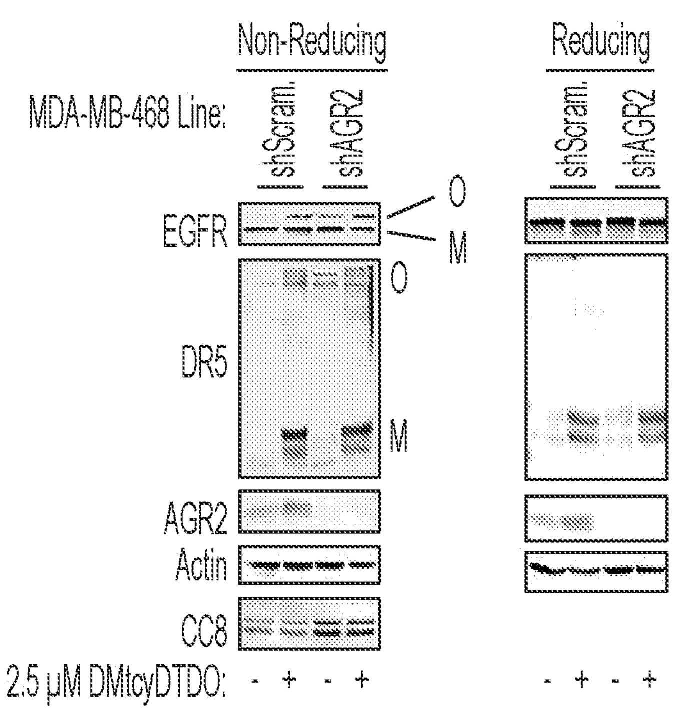
Figure 1D:
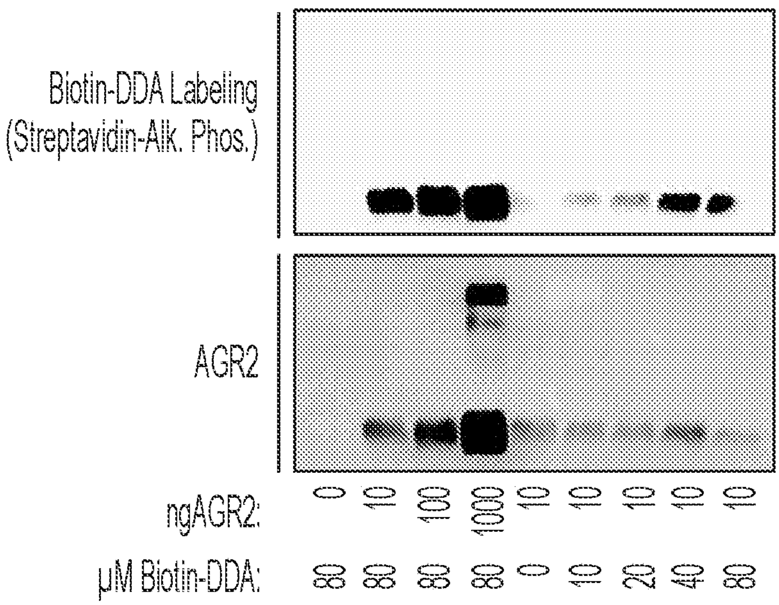
Figure 2A:
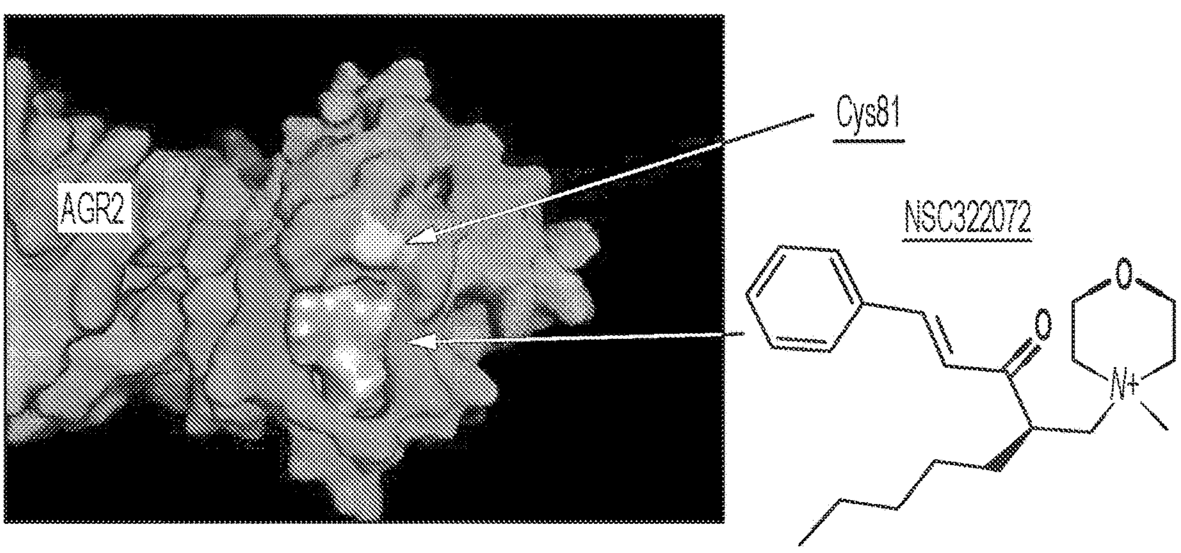
FIG. 2 depicts identification of a new AGR2 inhibitor that mimics the anticancer actions of DDAs. A. Molecular docking model showing the compound NSC322072 binding to a pocket adjacent to the AGR2 enzyme active site residue Cys81 (yellow). B. Immunoblot analysis showing that the DDA DMtcyDTDO and NSC322072 are similar in their ability to increase DR4, DR5, and HER3 oligomerization (O) and decrease Akt phosphorylation in the MDA-MB-468 TNBC and BT474 HER2+ lines. C. Cell viability assays showing that increasing concentrations of NSC322072 decrease the viability of three different breast cancer cell lines in a concentration-dependent manner.
Figure 2B:
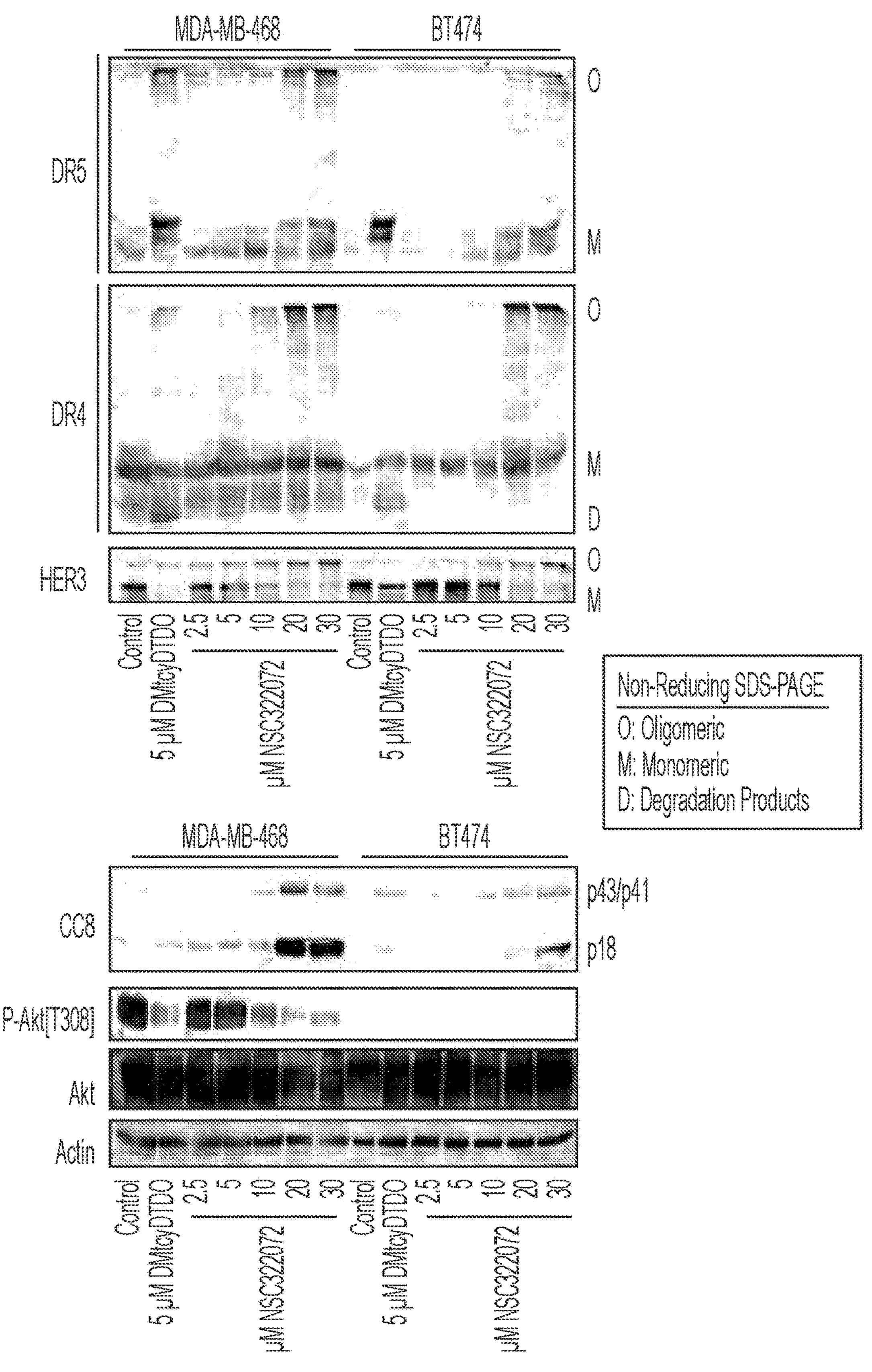
Figure 2C:
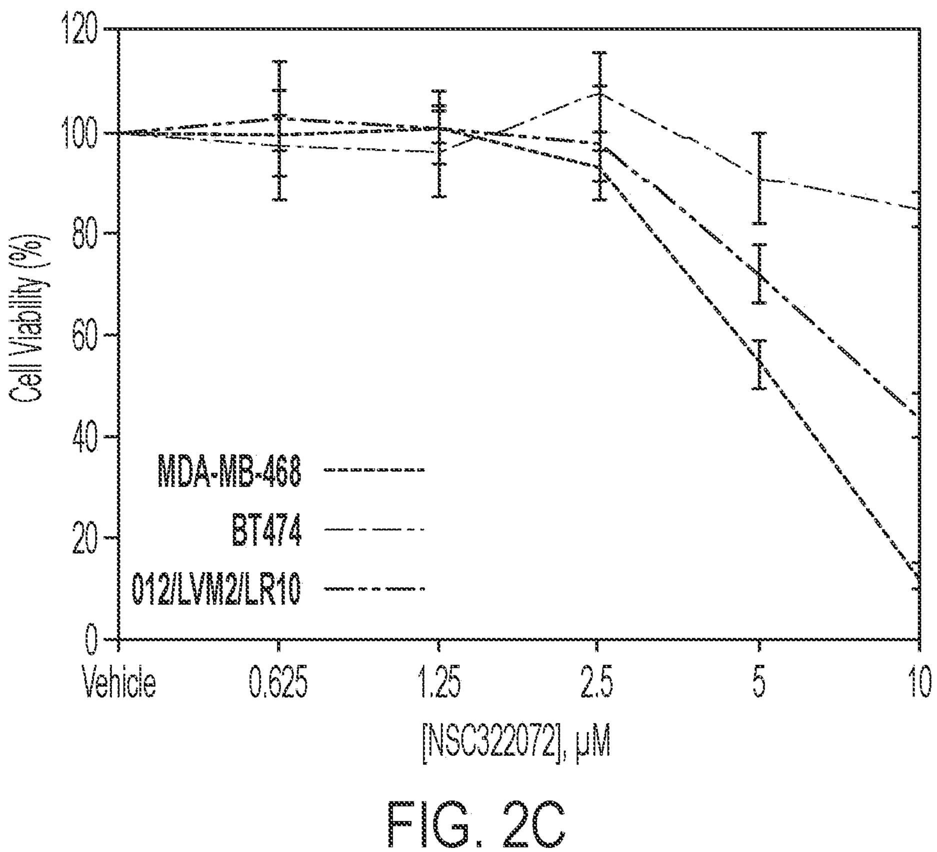
Figure 3A:
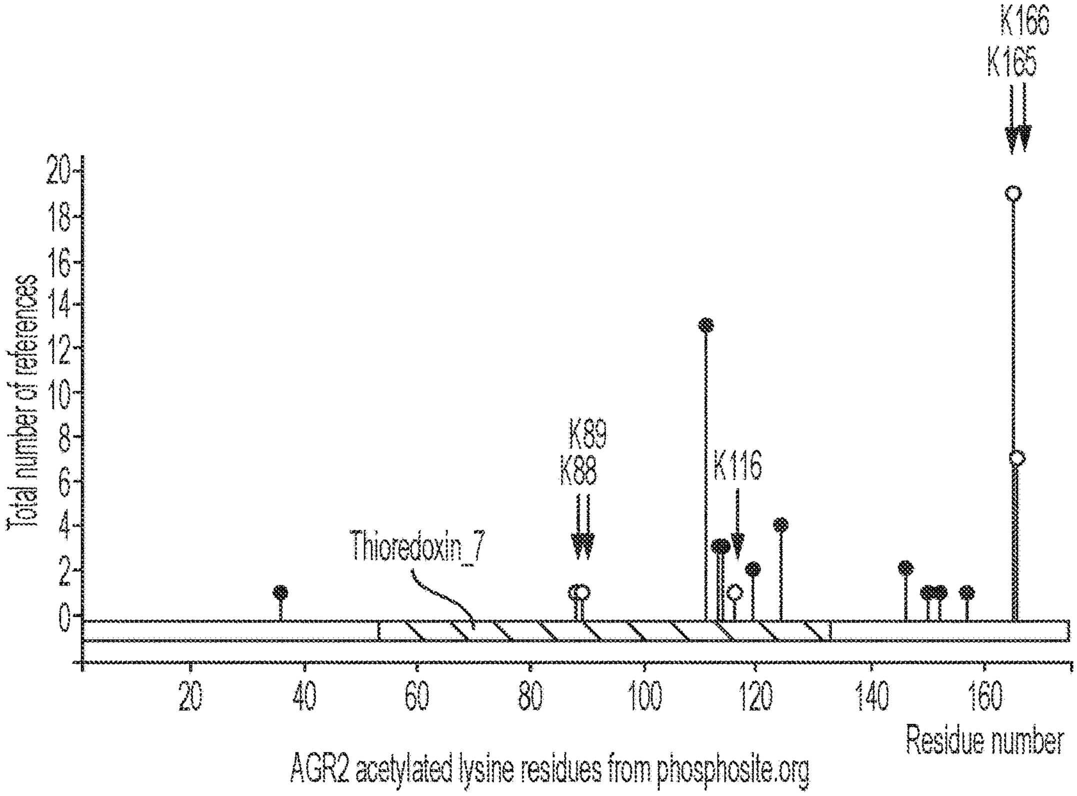
FIG. 3 depicts DR4, DR5, and EGFR disulfide bonding is controlled by ER acetyltransferases ATase 1 and ATase 2. A. AGR2 lysine (K) residues that were identified to be acetylated. The function of these acetylation sites is unknown. B. Inhibition of the ER acetyltransferases with Compound 9 ("C9") decreases the viability of breast cancer cell lines. C. Inhibitors of ER acetyltransferases, Compounds 9 ("C9") and 19 ("C19"), cause DR4, DR5, and EGFR oligomerization (O), but A-485, an inhibitor of the nuclear acetyltransferase p300 is without effect. D. Reducing the production of ATase 1 causes oligomerization of DR4, DR5, and EGFR, mimicking the effects of DDAs and AGR2 knockdown.
Figure 3B:
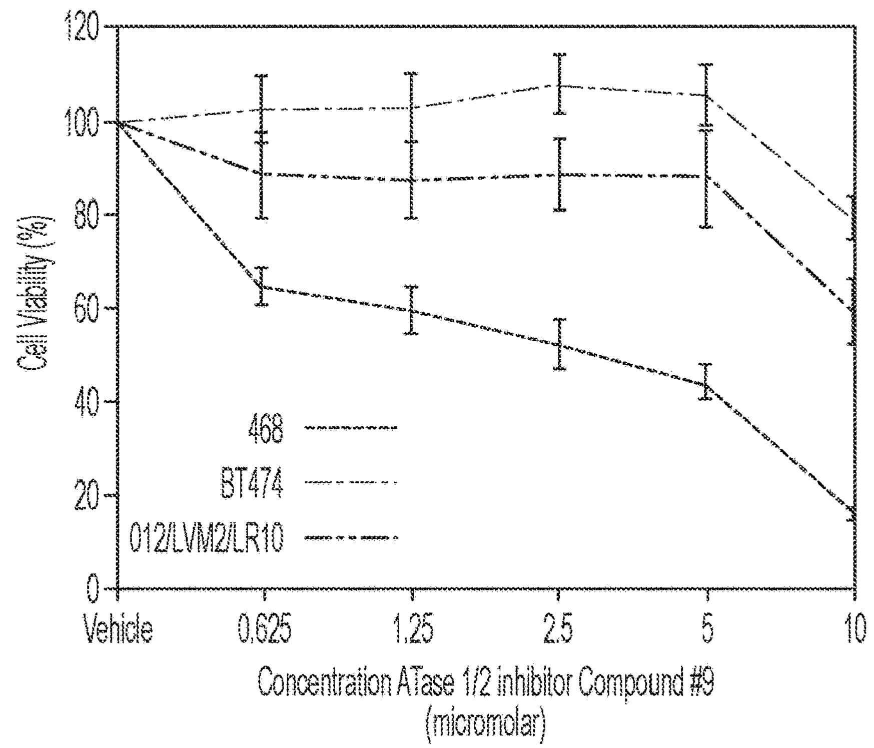
Figure 3C:
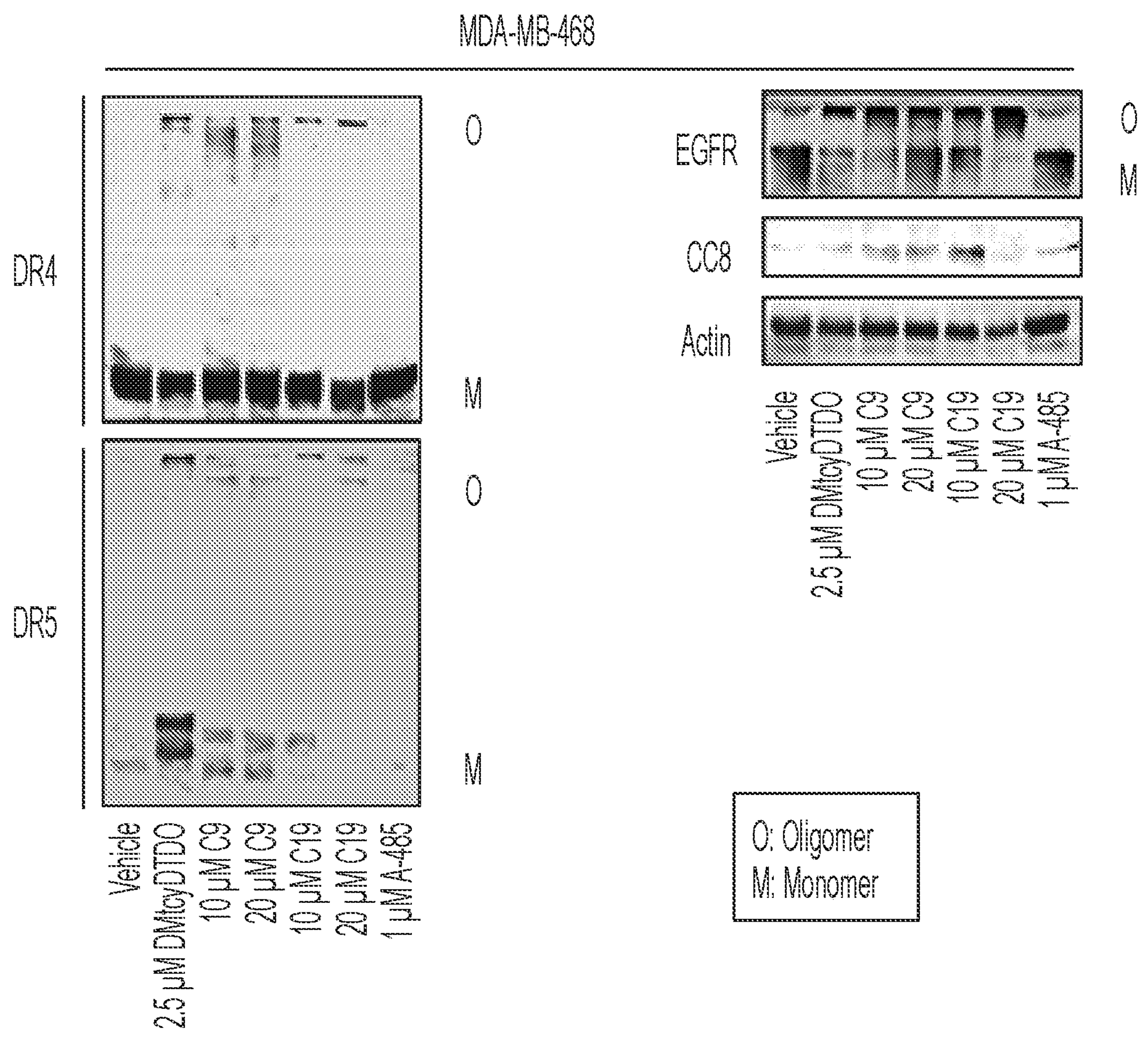
Figure 3D:
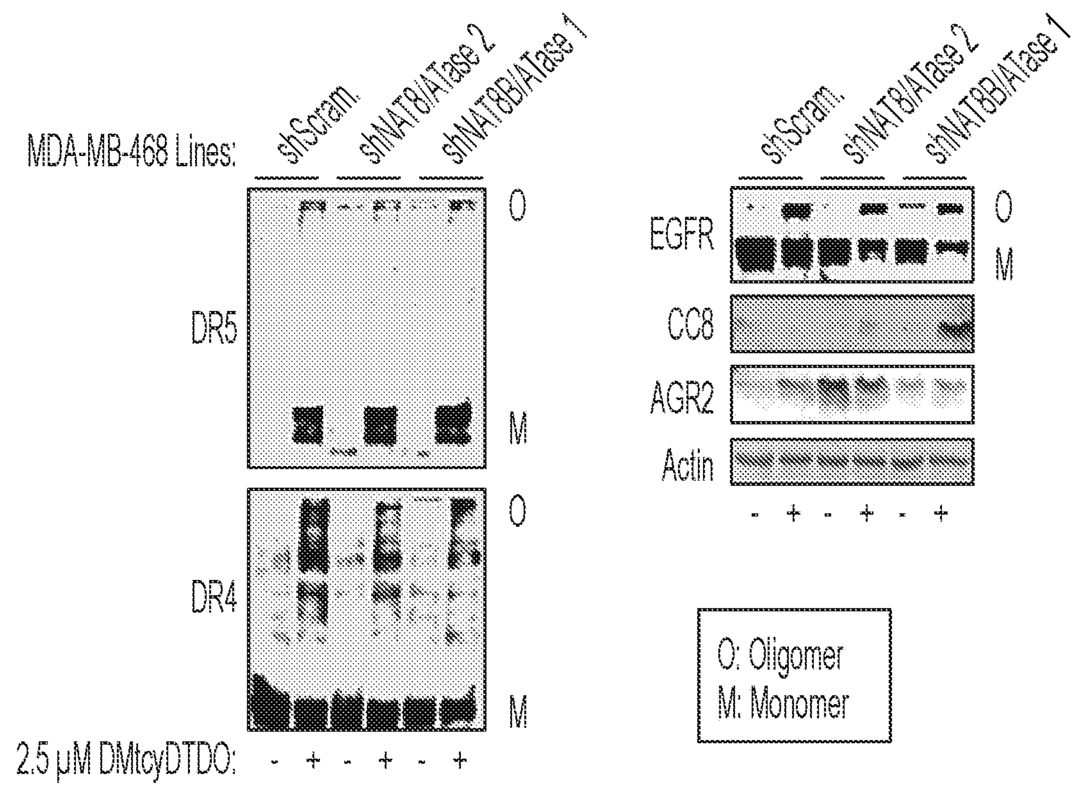
Figure 4A:
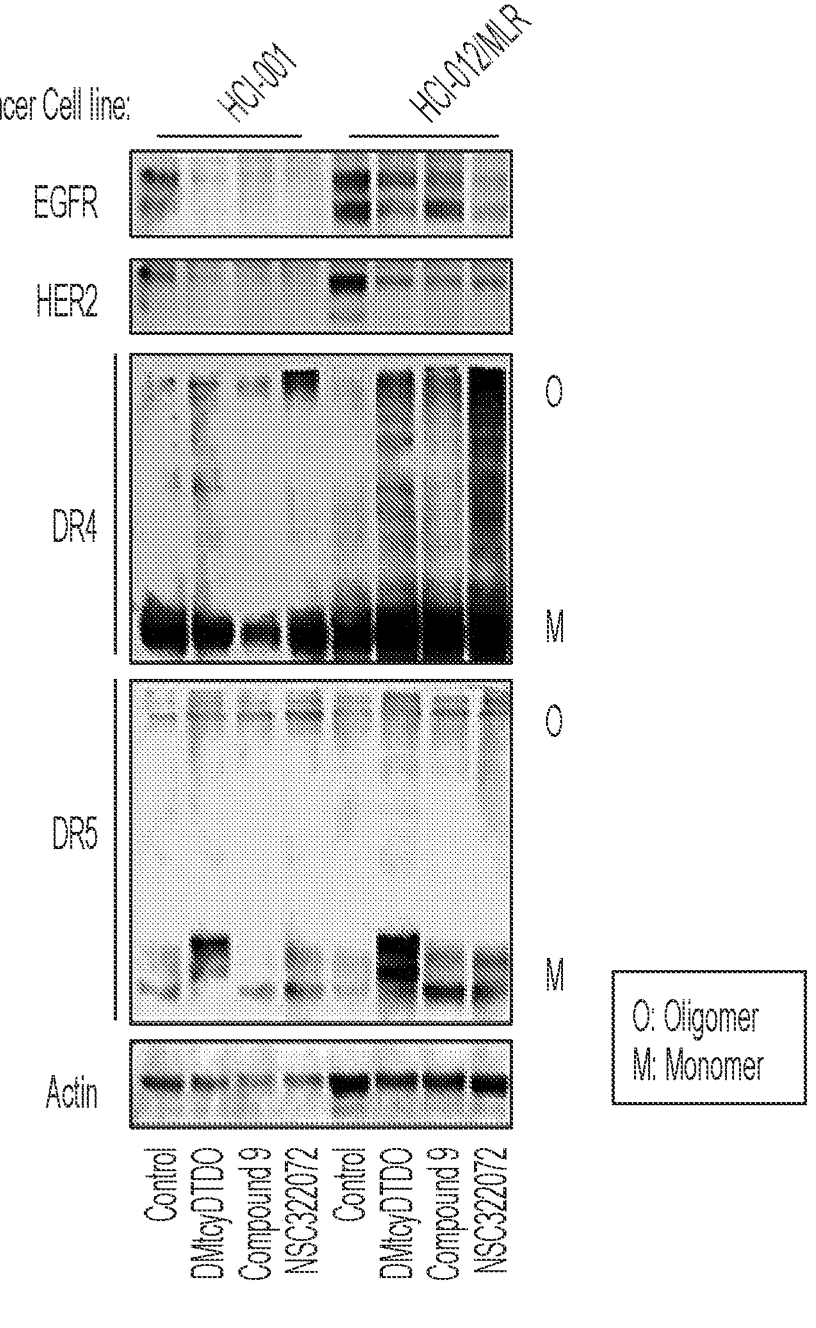
FIG. 4 depicts DDA effects on patient-derived breast cancer cell lines and patient derived pancreatic tumors. A. DMtcyDTDO, Compound 9 ("C9", and NSC322072 each decrease EGFR and HER2 levels in patient-derived breast cancer cells from a TNBC (HCI-001) and a drug resistant, metastatic, HER2+ breast cancer (HCI-012/MLR). B. Treatment of mice bearing pancreatic PDX tumors with the DDA TcyDTDO causes disintegration of the tumors indicated by separation of cancer cells from the surrounding stroma and pancreatic cancer cell death (red arrows). V1 and V2 are Hematoxylin and Eosin (H&E)-stained tumors from vehicle treated mice and T1-T3 are tumors from TcyDTDO treated mice.
Figure 4B:
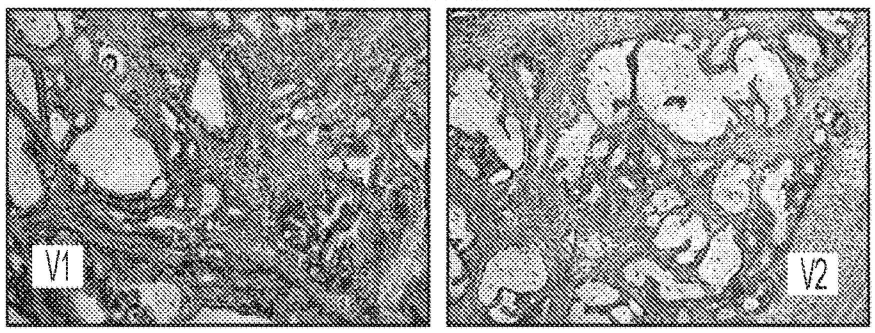
Figure 4B:
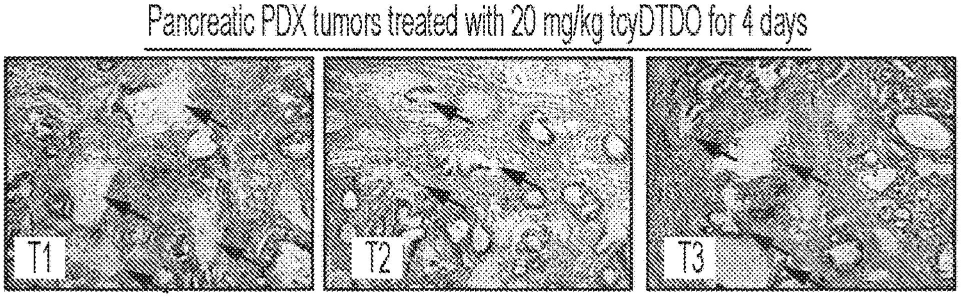
Figure 5:
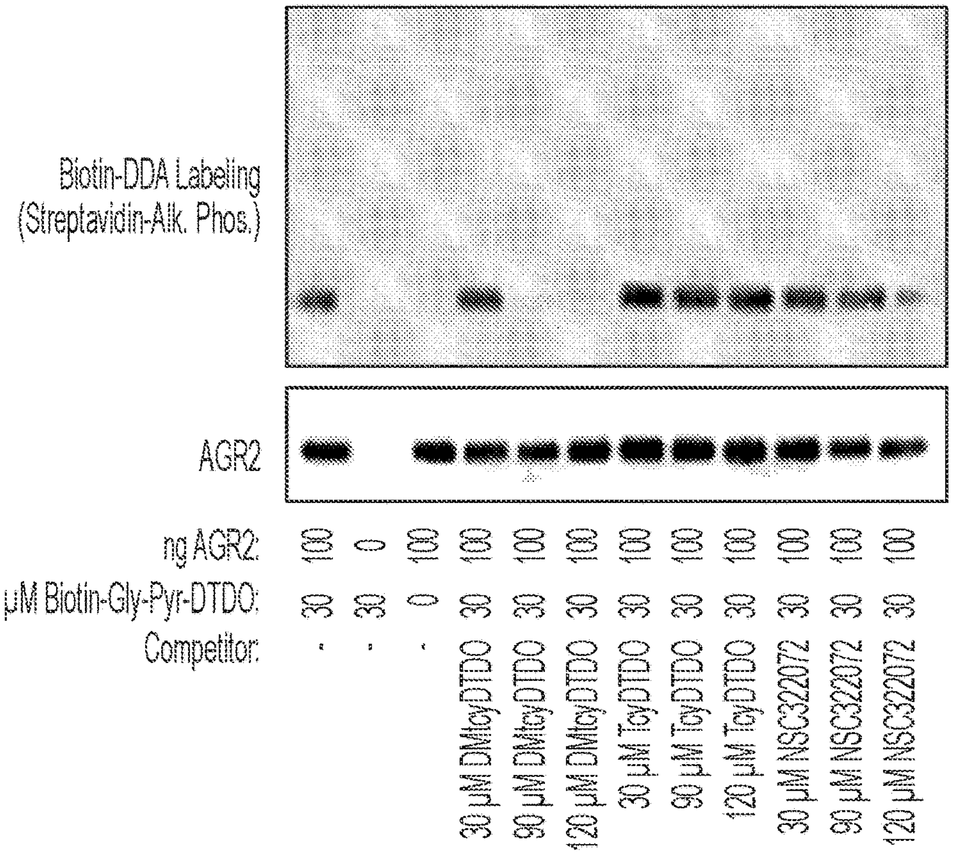
FIG. 5 depicts inhibition results at various concentrations of DMtcyDTDO, TcyDTDO, and NSC322072, based on incubation of a biotinylated DDA derivative with AGR2.
Figure 6:
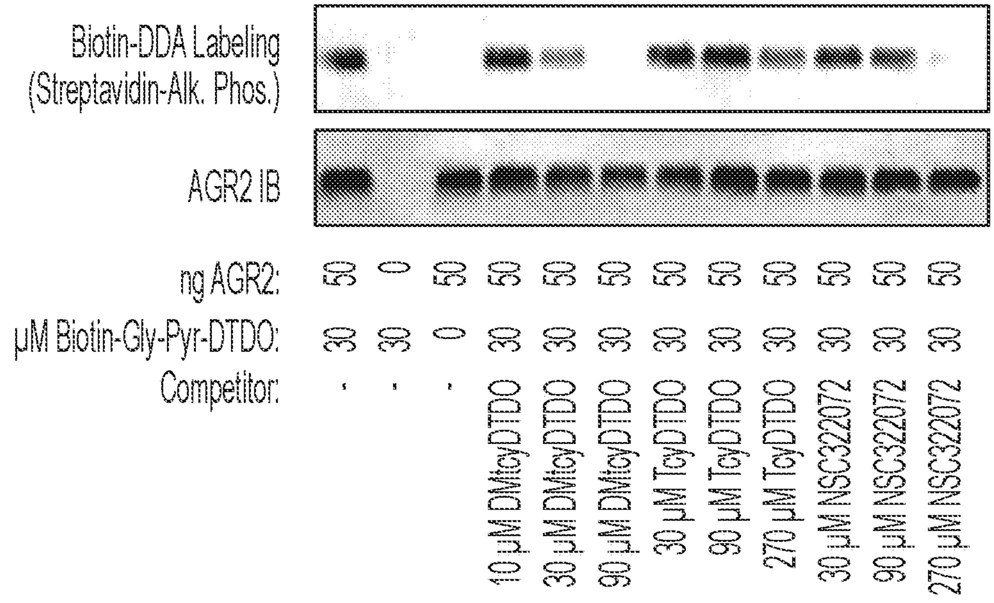
FIG. 6 depicts inhibition results at various concentrations of DMtcyDTDO, TcyDTDO, and NSC322072, based on incubation of a biotinylated DDA derivative with AGR2.

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In certain embodiments, the term "lower alkyl" includes a straight chain alkyl having 4 or fewer carbon atoms in its backbone, e.g., $C_1$-$C_4$ alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The term "haloalkoxy" as used herein, refers to the radical of —O-alkyl substituted with 1-5 halo atoms (e.g., fluoromethoxy, trifluoromethoxy, pentafluoroethoxy, and the like). The alkyl can be straight chain or branched chain containing 1-10 carbon atoms. Halo atoms independently are F, Cl, Br, or I, which can be the same or different in a haloalkoxy moiety.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In one embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In certain embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, or about 0.01 to 25 mg/kg body weight, or about 0.1 to 20 mg/kg body weight, or about 1 to 10 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or can include a series of treatments. In one example, a subject is treated with a compound of the invention in the range of between about 0.1 to 20 mg/kg body weight, one time per week for between about 1 to 10 weeks, or between 2 to 8 weeks, or between about 3 to 7 weeks, or for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In certain embodiments, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors (e.g., brain, lung (small cell and non-small cell), ovary, prostate, breast or colon) or other carcinomas or sarcomas (e.g., leukemia, lymphoma).

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —$CONH_2$, mono- or di-($C_1$-$C_8$alkyl)aminocarbonyl, —$SO_2NH_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound capable of inhibiting CDCP1" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a cell proliferative disorder.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" of the invention includes all vertebrates, e.g., mammals; e.g., rodents; e.g., mice; and non-mammals, such as non-human primates; e.g., sheep, dog, cow, chickens, amphibians, reptiles, etc.

The term "susceptible to a cell proliferative disorder" is meant to include subjects at risk of developing disorder of cell proliferation, e.g., cancer, i.e., subjects suffering from viral infection with cancer causing viruses, subjects that have been exposed to ionizing radiation or carcinogenic compounds, subjects having a family or medical history of cancer, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment.

With respect to the nomenclature of a chiral center, terms "d" and "1" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides a compound (e.g., any compound of a formulae herein) that inhibits or is capable of inhibiting AGR2.

In one aspect, the invention provides a pharmaceutical composition that inhibits or is capable of inhibiting AGR2, the pharmaceutical composition comprising: 1) a compound of any of the formula herein (i.e., any of Formula I-XI), or salt, solvate, hydrate or prodrug thereof.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

In some embodiments, haloalkoxy is fluoro-$C_1$-$C_6$-alkoxy. In some embodiments, haloalkoxy is fluoro-$C_1$-$C_3$-alkoxy, and $C_1$-$C_6$ alkoxy is $C_1$-$C_3$-alkoxy. In some embodiments, haloalkoxy is —$OCF_3$ and $C_1$-$C_6$ alkoxy is $C_1$-$C_3$-alkoxy. In some embodiments, haloalkoxy is —$OCF_3$ and $C_1$-$C_6$ alkoxy is methoxy. In some embodiments, halo is fluoro, haloalkoxy is —$OCF_3$, and $C_1$-$C_6$ alkoxy is methoxy.

In some embodiments, $R_3$ is halo or haloalkoxy; and $R_4$ is halo or haloalkoxy. In some embodiments, $R_3$ is halo; and $R_4$ is halo. In some embodiments, $R_3$ is fluoro; and $R_4$ is fluoro.

In certain embodiments, $R_3$ is haloalkoxy; and $R_4$ is haloalkoxy. In certain embodiments, $R_3$ is —$OCF_3$; and $R_4$ is —$OCF_3$. In some embodiments, $R_3$ is haloalkoxy; and $R_4$ is halo. In some embodiments, $R_3$ is —$OCF_3$; and $R_4$ is halo. In some embodiments, $R_3$ is haloalkoxy; and $R_4$ is fluoro. In certain embodiments, $R_3$ is halo; and $R_4$ is haloalkoxy. In certain embodiments, $R_3$ is halo; and $R_4$ is —$OCF_3$. In certain embodiments, $R_3$ is fluoro; and $R_4$ is haloalkoxy.

In some embodiments, $R_3$ is H or $C_1$-$C_6$ alkoxy; and $R_4$ is halo or haloalkoxy. In some embodiments, $R_3$ is H; and $R_4$ is halo. In some embodiments, $R_3$ is H; and $R_4$ is fluoro. In certain embodiments, $R_3$ is H; and $R_4$ is haloalkoxy. In certain embodiments, $R_3$ is H; and $R_4$ is —$OCF_3$. In some embodiments, $R_3$ is $C_1$-$C_6$ alkoxy; and $R_4$ is halo. In some embodiments, $R_3$ is methoxy; and $R_4$ is halo. In some embodiments, $R_3$ is $C_1$-$C_6$ alkoxy; and $R_4$ is fluoro. In certain embodiments, $R_3$ is $C_1$-$C_6$ alkoxy; and $R_4$ is haloalkoxy. In certain embodiments, $R_3$ is $C_1$-$C_6$ alkoxy; and $R_4$ is —$OCF_3$. In certain embodiments, $R_3$ is methoxy; and $R_4$ is haloalkoxy.

In certain embodiments, $R_3$ is halo or haloalkoxy; and $R_4$ is H or $C_1$-$C_6$ alkoxy. In some embodiments, $R_3$ is halo or haloalkoxy; and $R_4$ is H. In some embodiments, $R_3$ is halo or —$OCF_3$; and $R_4$ is H. In some embodiments, $R_3$ is fluoro or haloalkoxy; and $R_4$ is H. In some embodiments, $R_3$ is halo or —$OCF_3$; and $R_4$ is H. In certain embodiments, $R_3$ is halo or haloalkoxy; and $R_4$ is $C_1$-$C_6$ alkoxy. In certain embodiments, $R_3$ is halo or haloalkoxy; and $R_4$ is methoxy. In certain embodiments, $R_3$ is fluoro or haloalkoxy; and $R_4$ is $C_1$-$C_6$ alkoxy. In certain embodiments, $R_3$ is halo or —$OCF_3$; and $R_4$ is $C_1$-$C_6$ alkoxy.

3. Uses of the Compounds of the Invention

Thus, in one embodiment, the invention provides methods for treating a subject for a cell proliferative disorder, by administering to the subject an effective amount of a compound of Formula (I)-(XI), or salt thereof; or a pharmaceutical composition comprising a compound of Formula (I)-(XI) or salt thereof. A cell proliferative disorder includes cancer. In certain embodiments, the subject is a mammal, e.g., a primate, e.g., a human.

A further aspect presents a method of treating a subject suffering from or susceptible to cancer, including administering to the subject an effective amount of a compound of any one of Formulae I-XI, or salt, solvate, hydrate or prodrug thereof; or a pharmaceutical composition thereof, to thereby treat the subject suffering from or susceptible to cancer.

In certain embodiments, the aforementioned methods of the invention include administering to a subject a therapeutically effective amount of a compound of any of the formulae herein (e.g., Formula (I)-(XI)), or salt thereof, in combination with another pharmaceutically active compound. Examples of pharmaceutically active compounds include compounds known to treat cell proliferative disorders, e.g., breast cancer therapeutics; pancreatic cancer therapeutics, etc. Other pharmaceutically active compounds that may be used include antibodies to AGR2, including antibodies to extracellular AGR2. Exemplary DR5 antibodies include, but are not limited to, conatumumab, drozitumab, apomab, DAB4, PR095780, lexatumumab, HGS-ETR2, tigatuzumab, CS-1008, TRA-8, HGSTR2J, KMTRS, LBY-135, and the like. Other pharmaceutically active compounds that may be used include a DR5 agonist, including TRAIL or TRAIL analog (e.g., TRAIL 10 trimer, stabilized form of TRAIL, and the like), a DR5 agonist antibody, or a TRAIL synthesis inducer (e.g., TIC10), all of which are described in WO 2019/241644 (published Dec. 19, 2019; incorporated by reference). The compound of the invention and the pharmaceutically active compound may be administered to the subject in the same pharmaceutical composition or in different pharmaceutical compositions (at the same time or at different times).

In certain embodiments, the aforementioned methods of the invention include administering to a subject a therapeutically effective amount of a compound of any of the formulae herein (e.g., Formula (I)-(XI)), or salt thereof, in combination with another conventional treatment regimen known in the art. Conventional treatment regimens for cancer and for other tumors include radiation, surgery, drugs, or combinations thereof.

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a cell proliferative disorder by methods well known in the art (e.g., determining tumor size or screening for tumor markers where the cell proliferative disorder is cancer) and then administering a therapeutically effective amount of an inhibitor of cell proliferation (e.g., a compound of any formula herein or otherwise described herein) according to the invention to the subject. After an appropriate period of time after the administration of the compound (e.g., 1 day, 1 week, 2 weeks, one month, six months), the extent of the cell proliferative disorder is determined again. The modulation (e.g., decrease) of the extent or invasiveness of the cell proliferative disorder indicates efficacy of the treatment. The extent or invasiveness of the cell proliferative disorder may be determined periodically throughout treatment. For example, the extent or invasiveness of the cell proliferative disorder may be checked every few hours, days or weeks to assess the further efficacy of the treatment. A decrease in extent or invasiveness of the cell proliferative disorder indicates that the treatment is efficacious. The method described may be used to screen or select patients that may benefit from treatment with an inhibitor of a cell proliferative disorder.

As used herein, "obtaining a biological sample from a subject," includes obtaining a sample for use in the methods described herein. A biological sample is described above.

In another aspect, a compound of any of the formulae herein (e.g., Formula (I)-(XI)), or salt thereof, or pharmaceutical composition comprising a compound of any of the formulae herein (e.g., Formula (I)-(XI)) or salt thereof is packaged in a therapeutically effective amount with a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In another aspect, methods of inhibiting a cell proliferative disorder in a subject include administering an effective amount of a compound of the invention to the subject. The administration may be by any route of administering known in the pharmaceutical arts. The subject may have a cell proliferative disorder, may be at risk of developing a cell proliferative disorder, or may need prophylactic treatment prior to anticipated or unanticipated exposure to conditions capable of increasing susceptibility to a cell proliferative disorder, e.g., exposure to carcinogens or to ionizing radiation.

In one aspect, a method of monitoring the progress of a subject being treated includes determining the pre-treatment status (e.g., size, growth rate, or invasiveness of a tumor) of the cell proliferative disorder, administering a therapeutically effective amount of a compound of any of the formulae herein (e.g., Formulae (I)-(XI)), or salt, solvate, hydrate or prodrug thereof, (or a dosing regimen or pharmaceutical composition thereof) to the subject, and determining the status of the cell proliferative disorder after an initial period of treatment, wherein the modulation of the status indicates efficacy of the treatment.

The subject may be at risk of a cell proliferative disorder, may be exhibiting symptoms of a cell proliferative disorder, may be susceptible to a cell proliferative disorder and/or may have been diagnosed with a cell proliferative disorder.

The initial period of treatment may be the time in which it takes to establish a stable and/or therapeutically effective blood serum level of any of the compounds, compound combinations, dosing regimens, or pharmaceutical compositions delineated herein, or the time in which it take for the subject to clear a substantial portion of the compound, or any period of time selected by the subject or healthcare professional that is relevant to the treatment.

If the modulation of the status indicates that the subject may have a favorable clinical response to the treatment, the subject may be treated with the compound. For example, the subject can be administered a therapeutically effective dose or doses of the compound.

In another aspect, the invention provides methods for inhibiting EGFR, HER2, and/or HER3 signaling in a cell. The methods include contacting the cell with an effective amount of any of the compounds, compound combinations, dosing regimens, or pharmaceutical compositions delineated herein, such that the signaling of EGFR, HER2, and/or HER3 is reduced. The contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

The EGFR, HER2, and/or HER3 may be within a cell, isolated from a cell, recombinantly expressed, purified or isolated from a cell or recombinant expression system or partially purified or isolated from a cell or recombinant expression system.

The contacting may be in vitro, e.g., by addition of the compound to a solution containing purified EGFR, HER2, and/or HER3, or, if EGFR, HER2, and/or HER3 is present in cells, by adding the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

Kits of the invention include kits for treating a cell proliferative disorder in a subject. The invention also includes kits for downregulating expression of EGFR, HER2, and/or HER3, stabilizing an interaction of EGFR, HER2, and/or HER3, assessing the efficacy of a treatment for a cell proliferative disorder in a subject, monitoring the progress of a subject being treated for a cell proliferative disorder, selecting a subject with a cell proliferative disorder for treatment according to the invention, and/or treating a subject suffering from or susceptible to a cell proliferative disorder. The kit may include any of the compounds, compound combinations, dosing regimens, or pharmaceutical compositions delineated herein and instructions for use. The instructions for use may include information on dosage, method of delivery, storage of the kit, etc. The kits may also include reagents, for example, test compounds, buffers, media (e.g., cell growth media), cells, etc. Test compounds may include known compounds or newly discovered compounds, for example, combinatorial libraries of compounds. One or more of the kits of the invention may be packaged together, for example, a kit for assessing the efficacy of a treatment for a cell proliferative disorder may be packaged with a kit for monitoring the progress of a subject being treated for a cell proliferative disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

Alternatively, the effects of compound of the invention can be characterized in vivo using animals models.

4. Pharmaceutical Compositions

In another aspect, the invention provides a pharmaceutical composition comprising: a compound of any of the formulae herein (e.g., Formula (I)-(XI)), or salt, solvate, hydrate or prodrug thereof; and a pharmaceutically acceptable carrier.

In another aspect, the invention provides a method for making a pharmaceutical composition comprising combining: a compound of any of the formulae herein (e.g., Formula (I)-(XI)), or salt, solvate, hydrate or prodrug thereof; and a pharmaceutically acceptable carrier.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, oxalic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also be used in the pharmaceutical compositions herein.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount of a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

By “pharmaceutically effective amount” as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, or from about 5 percent to about 70 percent, or from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH 5 to pH 7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of an enzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in an in vitro assay, such as those described in the Examples section. Calculating dosages to achieve such circulating blood or serum concentrations taking into account the bioavailability of the particular compound is well within the capabilities of skilled artisans. For guidance, see Goodman and Gilman's *The Pharmacological Basis of Therapeutics,* 13th or latest edition, McGraw Hill Medical, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a disorder or disease (e.g., any disorder or disease herein). Another object of the present invention is the use of a compound as described herein (e.g., of any formulae herein) for use in the treatment of a disorder or disease (e.g., any disorder or disease herein).

EXAMPLES

The invention is further illustrated by the following examples which are intended to illustrate but not limit the scope of the invention.

General Methods

Reagents and solvents were purchased from commercial sources and used without further purification unless otherwise specified. Anhydrous solvents were obtained using a commercial solvent drying system (using activated alumina for THF, dichloromethane) and transferred via syringe to flame-dried glassware that had been cooled under an argon or nitrogen atmosphere. $^1H$ and $^{13}C$ NMR spectra were recorded using commercially-obtained deuterated solvents on a Bruker-400 ($^1H$ at 400 MHz; $^{13}C$ at 101 MHz) spectrometer. Chemical shifts (δ) are given in parts per million (ppm) relative to TMS and referenced to residual protonated solvent ($CDCl_3$: $\delta_H$ 7.26 ppm, $\delta_C$ 77.16 ppm; $CD_3OD$: $\delta_H$ 4.87 ppm, $\delta_C$ 49.00 ppm; DMSO-$d_6$: $\delta_H$ 2.50 ppm, $\delta_C$ 39.52 ppm; $D_2O$: $\delta_H$ 4.79 ppm). Coupling constants (J) are reported in Hz. Spin multiplicities are presented by the following symbols: s (singlet), bs (broad singlet), d (doublet), t (triplet), q (quartet), p (pentet), and m (multiplet). Electrospray ionization (ESI) high-resolution mass spectra (HRMS) were recorded on an Agilent 6230 ESI-TOF instrument, operating in positive or negative ion mode as stated, with methanol as the carrier solvent.

Example 1—Compound Synthesis

Method: Synthesis of Cyclic Analogs

Generally, a solution of the appropriate dithiol (24.7 mmol) in AcOH (25 mL) is cooled in an ice bath and a 30% aqueous $H_2O_2$ solution (8.8 mL) is added slowly such that the temperature does not rise above 35° C. After stirring for an appropriate amount of time, the solvent is removed under vacuum, and the residue is diluted with water (25 mL), neutralized with $NaHCO_3$, and extracted with toluene (4×50 mL). The organic extract is dried with $MgSO_4$, and the solvent is removed under vacuum. The resulting solid may be recrystallized (e.g., from $Et_2O$) to afford the product.

A pathway to generate difluorinated derivative 7 is outlined in Scheme 1. The synthesis starts with epoxidation of the double bond on the cyclohexene diester (±)-1 using mCPBA. (Costero, A. M.; Villarroya, J. P.; Gil, S.; Aurell, M. J.; Ramirez de Arellano, M. C., Crown ethers derived from cyclohexane. Influence of their stereochemistry in complexation and transport. *Tetrahedron* 2002, 58 (33), 6729-6734.) Treatment of the epoxide with $Et_3N$-3HF as a source of nucleophilic fluoride provides hydrofluorinated compound 2 as a single stereoisomer in 85% yield (Scheme 1). Compound 3 can be obtained by inverting the stereochemistry of the hydroxyl group on compound 2. This can be achieved by triflation of the hydroxy group followed by displacement using tetrabutylammonium benzoate and subsequent cleavage of the benzoyl group under basic conditions to provide the fluorohydrin 3. Installation of the second fluorine is achieved by triflation followed by treatment with $Et_3N$-3HF to furnish compound 4. Ester reduction using lithium aluminum hydride provides the dihydroxy intermediate that can be mesylated to give compound 5. Thioacetate substitution followed by acetyl cleavage furnishes dithiol that can be oxidized to disulfide 6. Ultimately, oxidation of 6 using $H_2O_2$ (30%) affords compound 7 (Scheme 1). Methylation of the hydroxy group on compound 2 then following similar chemistry provides DDA derivatives 33 and 34 (Table 2)

Scheme 1.

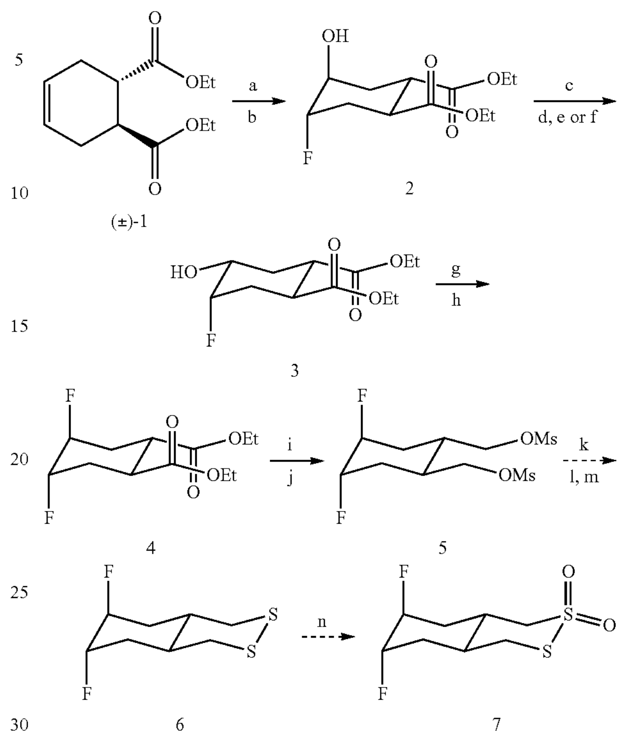

(±)-1, 2, 3, 4, 5, 6, 7

Proposed pathway to get (4aS,6S,7S,8aS) and (4aR,6R,7R,8aR) -6,7-difluorooctahydrobenzo[d][1,2]dithiine 2,2-dioxide, (±)-7. a) mCPBA, DCM, 16 h, 0° C. to rt., 95% b) $Et_3N$-3HF, 55° C., 2 days, 90% c) $Tf_2o$, pyridine, DCM, 2 h, 0° C. to rt., 86% d) $(Bu)_4N^+BzO^-$, toluene, 6 h, rt., 56% e) NaOEt, EtOH, 16 h, rt., 85% f) $Et_3N$-3HF, 24 h, rt., 75% g) $Tf_2O$, pyridine, DCM, 85% h) $Et_3N$-3HF 35% i) LAH, THF, 87% j) MsCl, $Et_3N$, DCM, 77% k) KSAc, 18-crown-6, DMF, rt., 60% l) $LiBH_4$, THF, 0° C. to rt., m) $SiO_2$, $Br_2$, $H_2O$, DCM, rt., n) $H_2O_2$ (30%), AcOH.

TABLE 2

Fluorinated tcyDTDO derivatives on C-4 and/or C-5.

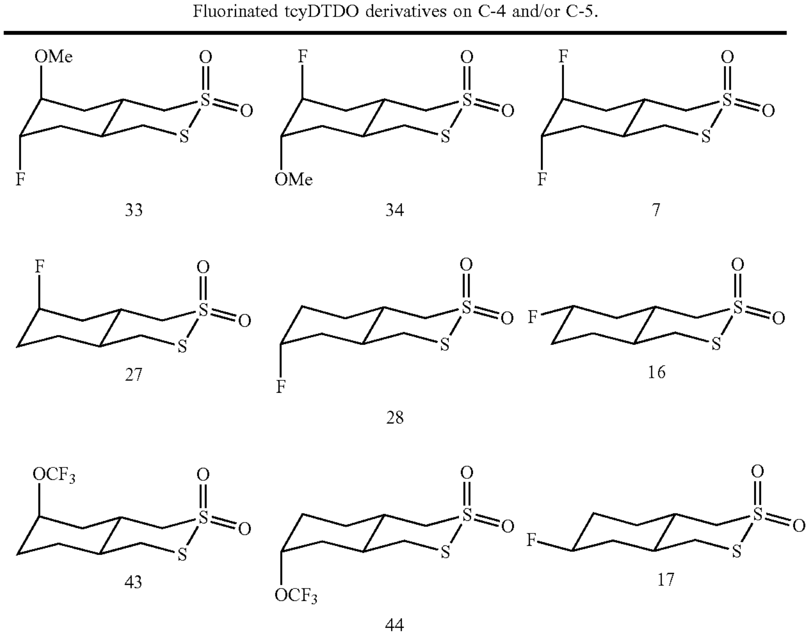

33, 34, 7

27, 28, 16

43, 44, 17

TABLE 2-continued

Fluorinated tcyDTDO derivatives on C-4 and/or C-5.

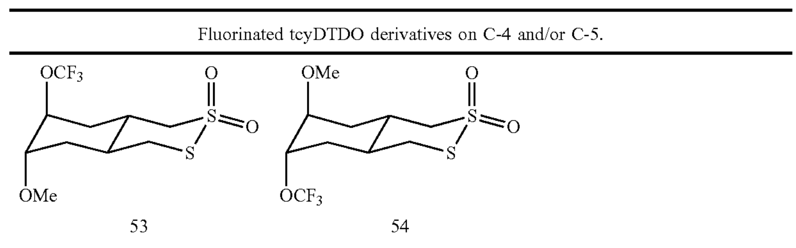

53 54

Mono, difluorinated, and O-trifluoromethylated derivatives as well as their related regio- and stereoisomers (Table 2) is achieved by analogous protocols to determine the importance of various substituents and their relative stereochemistry on the TcyDTDO scaffold, and subsequently their effect on the biological activity of the molecules. For example, a general pathway to obtain monofluorinated derivatives, 16 and 17, is shown in Scheme 2. In this case treatment of the epoxide intermediate with $NaBH_4$ provides hydroxy compound 8 that can be protected by a Boc group. Then a series of reduction, mesylation, thioacetate substitution, and acetyl cleavage gives dithiol 11. Oxidation of dithiol 11 by mCPBA provides regioisomers 12 and 13. Deprotection of the Boc group followed by deoxyfluorination using DAST gives monofluorinated derivatives 16 and 17.

Scheme 2. Proposed pathway to get monofluorinated derivatives, (±)-16 and 17. a) mCPBA, DCM, 16 h, 0° C. to rt., 94% b) $NaBH_4$, EtOH, 4 h, reflux 74% c) $Boc_2O$, MEIM, DCM, 24 h, rt., d) LAH, THF, 12 h, 0° C. to rt., 80%, e) MsCl, $Et_3N$, DCM, 2 h, 0° C. to rt., 45% f) KSAc, 18-crown-6, DMF, rt., g) $LiBH_4$, THF, 0° C. to rt., h) MCPBA, DCM, 0° C. to rt., i) TFA, DCM, rt., j) DAST, -78 to 40° C.

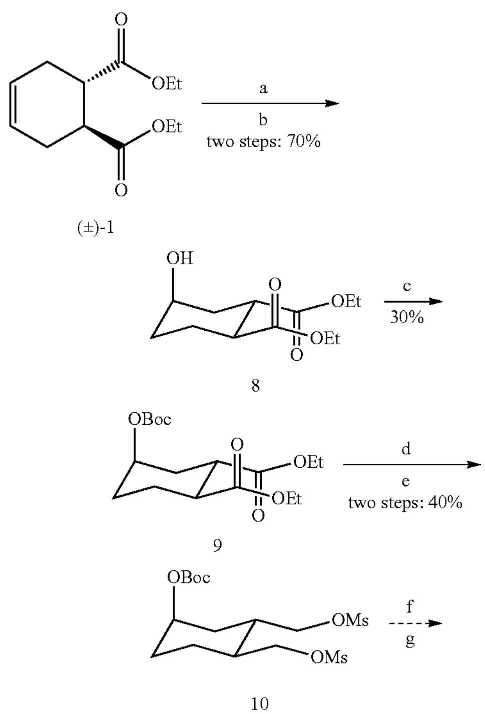

(±)-1

8

9

10

-continued

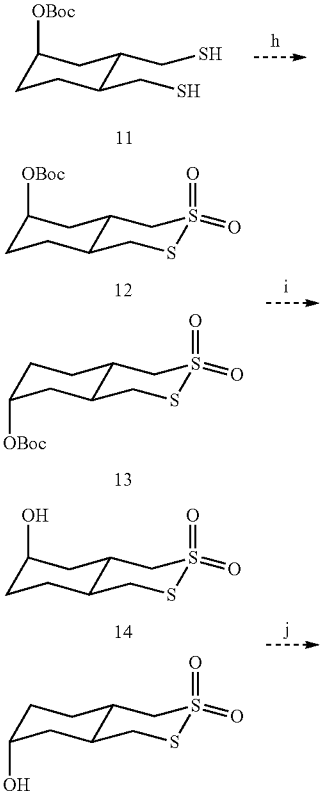

11

12

13

14

15

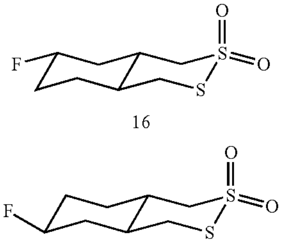

16

17

O-Trifluoromethylated derivatives (Table 2) are obtained by late-stage trifluoromethylation of the hydroxyl intermediate using literature defined conditions. (A) Koller, R.; Stanek, K.; Stolz, D.; Aardoom, R.; Niedermann, K.; Togni, A., *Angewandte Chemie International Edition* 2009, 48 (24), 4332. (B) Liu, J.-B.; Xu, X.-H.; Qing, F.-L., *Organic Letters* 2015, 17 (20), 5048.

Example 2—Synthesis of (±)-DFtcyDTDO

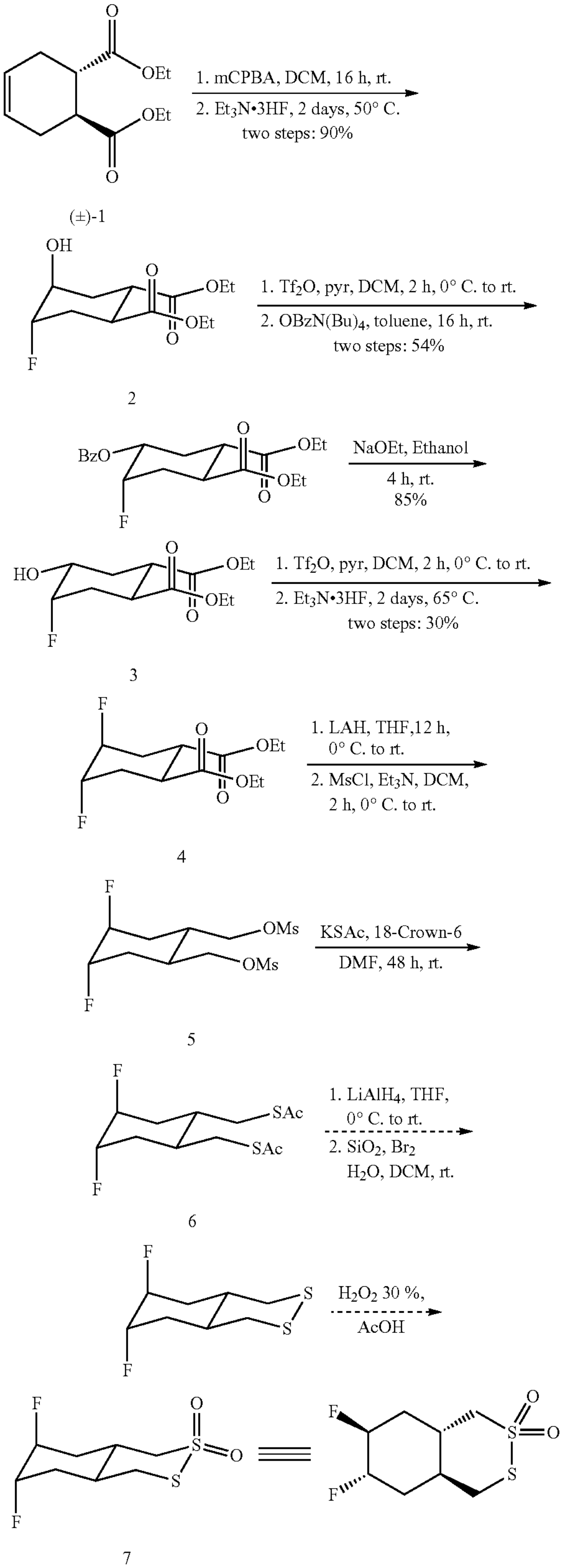

(±)-1, 2, 3, 4, 5, 6, 7

Diethyl (1S,2S,4S,5S) and (1R,2R,4R,5R)-4-fluoro-5-hydroxycyclohexane-1,2-dicarboxylate, 2

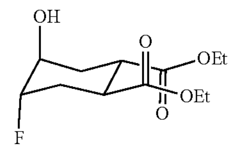

2

MCPBA 77% (6.9 g, 31 mmol) was added to a solution of diester 1 (5.0 g, 22 mmol) in anhydrous DCM (85 mL) at 0° C. The solution then was stirred at rt for 16 hours, monitoring by TLC. After reaction completion, the white precipitate was filtered off and saturated $NaHSO_3$ was then added to the filtrate and stirred for 10 min. The organic layer was separated, washed with $NaHCO_3$, dried over $Na_2SO_4$, and concentrated to give the crude epoxy diester (7.4 g, 30.5 mmol), which was used without further purification for the next step.

Epoxy diester (5.0 g, 20.6 mmol) was added to triethylamine trihydrofluoride (14.0 mL, 4.0 mmol) and stirred for 48 hours under nitrogen at 50° C. After full consumption of the epoxy diester, sat. $NaHCO_3$ solution was added until all the HF was neutralized and then extracted by EtOAc. Combined organic layers were washed with $NaHCO_3$ and brine, dried over $Na_2SO_4$, filtered, and concentrated. The mixture was purified by flash chromatography on silica (0-30% EtOAc/hexanes) to afford the desired 2 (4.9 g, 18.7 mmol, 90%) as a pale-yellow oil. $^1H$ NMR ($CDCl_3$, 600 MHz): δ 4.61 (dq, J=47.1, 4.5 Hz, 1H), 4.18-4.10 (m, 4H), 4.05-3.99 (m, 1H), 3.07 (td, J=9.9, 4.1 Hz, 1H), 3.01 (td, J=9.7, 4.7 Hz, 1H), 2.15-1.98 (m, 3H), 1.94 (dt, J=9.6, 4.5 Hz, 1H), 1.28-1.22 (m, 6H). $^{13}C$ NMR ($CDCl_3$, 151 MHz): δ 174.32, 174.12, 89.61 (d, J=173.6 Hz), 66.57 (d, J=26.4 Hz), 61.04, 61.01, 39.51 (d, J=3.3 Hz), 38.92, 30.56, 28.34 (d, J=20.4 Hz), 14.25. HRMS calcd for $C_{12}H_{19}FO_5$ $[M+Na]^+$: 285.1109; found: 285.1110.

Diethyl (1S,2S,4S,5S) and (1R,2R,4R,5R)-4-(benzoyloxy)-5-fluorocyclohexane-1,2-dicarboxylate

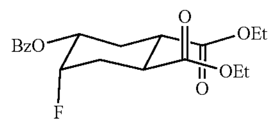

Pyridine (3.50 mL, 43.5 mmol) and compound 2 (6.0 g, 23.0 mmol) in dry DCM (35 mL) was added drop wise over a period of 10 minutes to a solution of trifluoromethanesulfonic anhydride (7.3 mL, 43.5 mmol) in dry DCM (35 mL) previously stirred for 10 minutes at 0° C. under Ar. The reaction mixture was stirred for 30 minutes at 0° C. and then stirred at rt. After reaction completion as evident by TLC, DCM was added and quenched with adding ice cold water. The organic solution was washed with ice cold water, dried over $MgSO_4$, filtered and the solvent removed in vacuo, to give the crude as a light brown oil (8.7 g, 22.1 mmol, 96%). The freshly provided crude was then used as is for the next step. $^1H$ NMR ($CDCl_3$, 400 MHz) δ 5.11-5.04 (m, 1H), 4.79 (dq, J=46.9, 5.5 Hz, 1H), 4.23-4.12 (m, 4H), 3.14-3.04 (m, 2H), 2.37-2.26 (m, 1H), 2.24-2.11 (m, 3H), 1.42-1.11 (m, 6H). $^{13}$C NMR ($CDCl_3$, 101 MHz): δ 172.6, 172.3, 118.5 (q, J=319.6 Hz), 86.4 (d, J=178.3 Hz), 82.6 (d, J=28.2 Hz), 61.6, 61.5, 39.4, 39.2 (d, J=4.9 Hz), 28.7, 28.45 (d, J=20.4 Hz) 14.2, 14.1. HRMS calcd for $C_{13}H_{18}F_4O_7S$ $[M+H]^+$: 395.0782; found: 395.0791.

Tetrabutylammonium benzoate (15.0 g, 41.1 mmol) was added to the solution of freshly provided triflate (8.10 g, 20.5 mmol) from previous step in anhydrous toluene (300 mL) and stirred under Ar for 2 h. After completion of the reaction, as evident by TLC, the solvent was removed in vacuo added DCM and washed with water and dried over $Na_2SO_4$. The product was purified by flash column chromatography on silica (0-20% EtOAc/hexanes) to give the title compound as colorless oil (4.50 g, 13.3 mmol, 65%). $^1$H NMR ($CDCl_3$, 400 MHz) δ 8.06 (dd, J=8.3, 1.2 Hz, 2H), 7.58 (tt, J=7.0, 1.3 Hz, 1H), 7.44 (t, J=7.7 Hz, 2H), 5.15-4.93 (m, 2H), 4.21-4.08 (m, 4H), 3.09 (td, J=12.2, 4.1 Hz, 1H), 2.90 (td, J=11.5, 3.6 Hz, 1H), 2.52 (ddt, J=14.6, 8.6, 4.4 Hz, 1H), 2.30 (dt, J=12.4, 4.6 Hz, 1H), 2.14 (q, J=11.7 Hz, 1H), 1.79 (dt, J=38.7, 12.9 Hz, 1H), 1.30-1.20 (m, 6H). $^{13}$C NMR ($CDCl_3$, 101 MHz): δ 173.9, 172.9, 165.8, 133.5, 130.0, 129.7, 128.6, 87.33 (d, J=178.7 Hz), 71.70 (d, J=17.8 Hz), 61.2, 42.7, 38.7, 31.74 (d, J=21.0 Hz), 27.5, 14.3, 14.2. HRMS calcd for $C_{19}H_{23}FO_6$ $[M+Na]^+$: 389.1371; found: 389.1375.

Diethyl (1S,2S,4S,5R) and (1R,2R,4R,5R)-4-fluoro-5-hydroxycyclohexane-1,2-dicarboxylate, 3

3

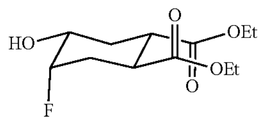

NaOEt (1.3 mL of 21% NaOEt in EtOH, 3.6 mmol) was added to the solution of benzoate intermediate (3.3 g, 8.9 mmol) in ethanol (90 mL) and stirred under nitrogen. After completion of the reaction, as evident by TLC, pH 7.4 phosphate buffer silane was added until pH gets close to neutral, then ethanol was removed under vacuum. The aqueous solution was extracted with EtOAc, then combined organic extracts were washed with sat. $NaHCO_3$ and brine, then dried over $NaSO_4$, filtered, and evaporated. The crude was purified by flash column chromatography on silica (0-40% EtOAc/hexanes) to give the title compound 3 as colorless oil (2 g, 7.6 mmol, 86% %). $^1$H NMR ($CDCl_3$, 400 MHz) δ 4.80 (d, J=50.3 Hz, 1H), 4.16-4.03 (m, 4H), 3.63 (dddd, J=27.6, 11.5, 4.5, 1.8 Hz, 1H), 2.89 (td, J=12.3, 4.1 Hz, 1H), 2.77 (bs, 1H), 2.69 (td, J=12.0, 3.7 Hz, 1H), 2.39 (ddd, J=18.9, 8.4, 4.2 Hz, 1H), 2.12 (dt, J=12.7, 4.2 Hz, 1H), 1.74 (q, J=12.4 Hz, 1H), 1.58 (dt, J=42.0, 13.1 Hz, 1H), 1.2-1.17 (m, 6H). $^{13}$C NMR ($CDCl_3$, 101 MHz): δ 174.1, 173.2, 89.97 (d, J=174.0 Hz), 69.51 (d, J=19.2 Hz), 60.9, 43.0, 38.6, 31.61 (d, J=20.8 Hz), 30.85 (d, J=3.3 Hz), 14.1. HRMS calcd for $C_{12}H_{19}FO_5$ $[M+Na]^+$: 285.1109; found: 285.1095.

Diethyl (1S,2S,4S,5S) and (1R,2R,4R,5R)-4,5-difluorocyclohexane-1,2-dicarboxylate, 4

4

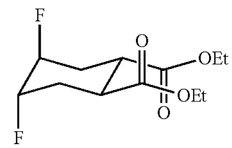

Pyridine (1.3 mL, 16 mmol) and compound 3 (2.4 g, 9.1 mmol) in dry DCM (15 mL) was added drop-wise over a period of 10 minutes to a solution of trifluoromethanesulfonic anhydride (3.0 mL, 18 mmol) in dry DCM (15 mL) previously stirred for 10 minutes at 0° C. under Ar. The reaction mixture was stirred for 30 minutes at 0° C. and then stirred at rt. After reaction completion as evident by TLC, DCM was added and quenched with adding ice-cold water. The organic solution was washed with ice-cold water, dried over $MgSO_4$, filtered and organic solvent removed in vacuo, to give the crude as a light brown oil (3.3 g, 8.4 mmol, 92%) that was used as is for the next step. $^1$H NMR ($CDCl_3$, 400 MHz) δ 5.14-4.73 (m, 2H), 4.25-3.95 (m, 4H), 3.03 (td, J=11.7, 4.2 Hz, 1H), 2.85 (td, J=10.8, 4.2 Hz, 1H), 2.50 (ddt, J=14.8, 8.0, 4.8 Hz, 1H), 2.40-2.17 (m, 2H), 1.77 (dt, J=37.9, 13.5 Hz, 1H), 1.40-1.09 (m, 2H). $^{13}$C NMR ($CDCl_3$, 101 MHz): δ 173.1, 171.7, 118.5 (q, J=319.3 Hz), 86.6 (d, J=183.1 Hz), 84.7 (d, J=18.4 Hz), 61.6, 61.4, 42.2, 38.1, 31.1 (d, J=20.7 Hz), 28.3 (d, J=2.8 Hz), 14.2, 14.1. HRMS calcd for $C_{13}H_{18}F_4O_7S$ $[M+Na]^+$: 417.0602; found: 417.0612.

Triflate intermediate (3.3 g, 8.4 mmol) was added to triethylamine trihydrofluoride (5.8 mL, 50 mmol) and stirred for 24 hours under Ar at 65° C. After full consumption of the triflate, sat. $NaHCO_3$ solution was added until all the HF was neutralized and then extracted by DCM. Combined organic layers were washed with $NaHCO_3$ and brine, dried over $Na_2SO_4$, filtered, and concentrated. The mixture was purified by flash chromatography on silica (0-5% EtOAc/hexanes) to afford the desired 4 (0.8 g, 3.0 mmol, 36%) as a colorless oil. $^1$H NMR ($CDCl_3$, 400 MHz) δ 4.80 (d, J=47.5 Hz, 2H), 4.31-3.99 (m, 4H), 3.16-2.85 (m, 2H), 2.36-2.15 (m, 2H), 2.08-1.80 (m, 2H), 1.41-1.10 (m, 6H). $^{13}$C NMR ($CDCl_3$, 101 MHz): δ 173.7, 85.9 (dd, J=173.7, 32.0 Hz), 61.1, 38.9, 28.6 (dd, J=12.8, 7.5 Hz), 14.2. HRMS calcd for $C_{12}H_{18}F_2O_4$ $[M+Na]^+$: 287.1065; found: 287.1063.

((1S,2S,4S,5S) and (1R,2R,4R,5R)-4,5-Difluorocyclohexane-1,2-diyl)bis(methylene) dimethanesulfonate, 5

5

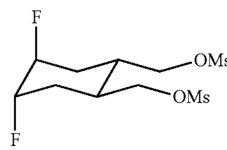

To an ice-cooled solution of compound 4 (0.8 g, 3.0 mmol) in anhydrous THF (15 mL) was added $LiAlH_4$ (0.3 g 9.0 mmol) in small portions then the reaction mixture was stirred under Ar atmosphere for 8 hours at rt. After this time water was added dropwise, and the white precipitate filtered off and washed with DCM. The filtrate extracted with DCM (5×15 mL), the combined organic extracts were dried over $Na_2SO_4$, filtered, and concentrated to give the diol (0.45 g, 2.5 mmol, 87% yield) as white powder which was used without further purification for the next step. $^1H$ NMR (Methanol-$d_4$, 400 MHz) δ 4.77 (d, J=51.8 Hz, 2H), 3.68-3.46 (m, 4H), 2.01-1.91 (m, 2H), 1.88-1.58 (m, 6H). $^{13}C$ NMR (Methanol-$d_4$, 101 MHz) δ 88.8 (dd, J=170.3, 31.5 Hz), 64.9, 36.5, 30.5-30.2 (m). HRMS calcd for $C_{82}H_{14}F_2O_2$ $[M+H]^+$: 181.1035; found: 181.1037.

A solution of the diol (0.45 g, 2.5 mmol) in anhydrous DCM (9 mL) was cooled to 0° C. and added triethylamine (1.0 mL, 7.5 mmol) followed by methanesulfonyl chloride (1.5 mL, 20.0 mmol). The reaction mixture was stirred at 0° C. for 15 min, then at rt for 2 h. After completion of the reaction, water was added, and the reaction mixture was extracted with DCM. Combined organics were dried over $Na_2SO_4$, filtered, and concentrated. The crude was purified by flash silica gel column chromatography (20-60% EtOAc/hexanes) and then recrystallized in methanol to afford the desired dimesylate 5 (0.65 g, 1.9 mmol, 77%) as a crystalline white solid. $^1H$ NMR ($CDCl_3$, 400 MHz) δ 4.84 (d, J=46.2 Hz, 2H), 4.36 (dd, J=10.4, 3.6 Hz, 2H), 4.16 (dd, J=10.4, 2.6 Hz, 2H), 3.04 (s, 6H), 2.16-2.01 (m, 4H), 2.00-1.73 (m, 2H). $^{13}C$ NMR ($CDCl_3$, 101 MHz) δ 86.0 (dd, J=171.6, 33.4 Hz), 70.4, 37.4, 31.9, 30.2-28.7 (m). calcd for $C_{10}H_{18}F_2O_6S_2$ $[M+Na]^+$: 359.0405; found: 359.0395.

((1S,2S,4S,5S) and (1R,2R,4R,5R)-4,5-Difluorocyclohexane1,2-diyl)bis(methylene)) diethanethioate, 6

6

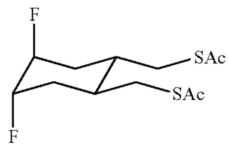

A mixture of the dimesylate 5 (54 mg, 0.16 mmol), KSAc (37 mg, 0.32 mmol), and 18-crown-6 (25 mol %) in anhydrous DMF (3 mL) was stirred for 48 h at room temperature. After this time DMF was evaporated, water added, and the mixture was extracted with DCM (3×20 mL). The combined organic phases were washed with water and brine, dried over $Na_2SO_4$, concentrated, and purified by column chromatography (0-20% DCM/EtOAc) to afford the dithioacetate 6 (30 mg, 0.10 mmol, 63% yield) as a viscous oil.

Example 3—Synthesis of dOBtcyDTDO

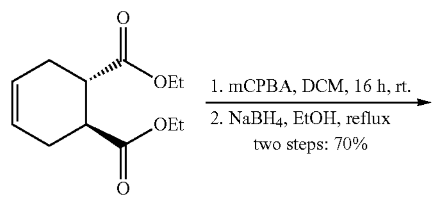

(±)-1

-continued

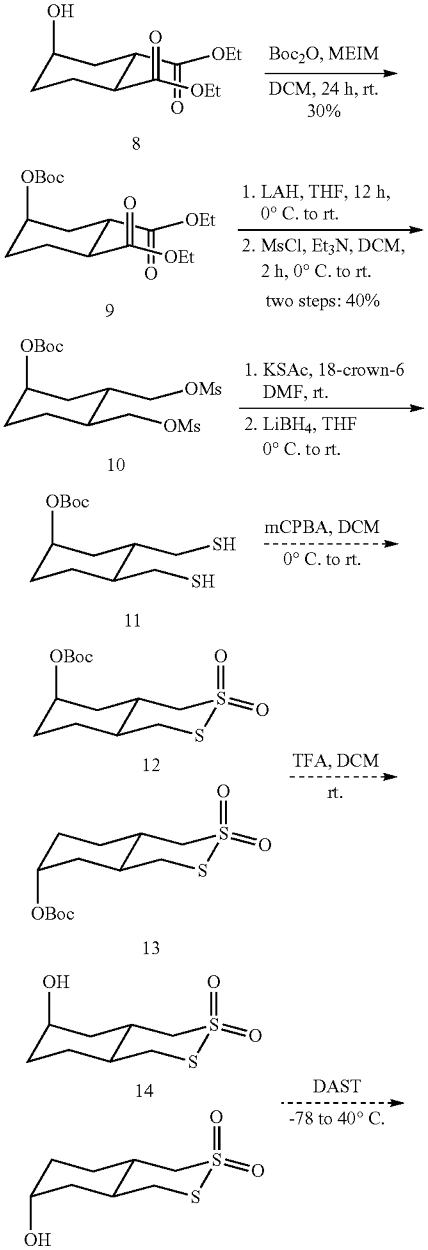

8, 9, 10, 11, 12, 13, 14, 15

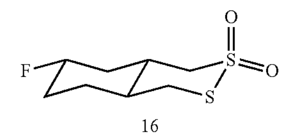

16

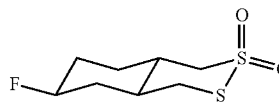

17

Diethyl (1S,2S,4R) and (1R,2R,4S)-4-((tert-butoxycarbonyl)oxy)cyclohexane-1,2-dicarboxylate, 3

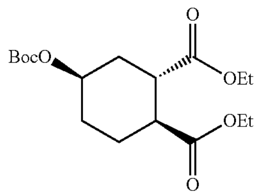

3

$Boc_2O$ (5.90 g, 27.0 mmol) was added to a solution of compound 2 (3.0 g, 12.4 mmol) and N-methylimidazole (MEIM, 100 μL, 1.24 mmol) in 62 mL DCM. The reaction mixture was stirred at rt, under Ar for 48 h, monitoring by TLC. After reaction completion, solvent was evaporated under vacuum and crude was purified by flash silica gel column chromatography (0-20% EtOAc/hexanes) to afford the desired product 3 (1.3 g, 3.7 mmol, 30% yield) as a white solid.

((1S,2S,4R) and (1R,2R,4S)-4-((tert-Butoxycarbonyl)oxy)cyclohexane-1,2-diyl)bis(methylene) dimethanesulfonate, 4

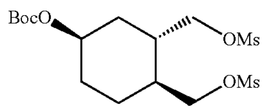

4

To an ice-cooled solution of the 3 (1.1 g, 3.3 mmol) in anhydrous THF (9 mL) was added dropwise a solution of $LiBH_4$ in THF (2.4 mL of a 4.0 M $LiBH_4$ solution in THF diluted with an additional 2 mL of anhydrous THF). The reaction mixture was stirred for 24 hours at rt and quenched with an aqueous 2 M NaOH solution. DCM was added, the layers were separated, and the aqueous phase was back extracted twice with DCM. The combined organic extracts were dried over $Na_2SO_4$, filtered, and concentrated to give the diol which was purified by recrystallization in EtOAc and provided the diol product (0.68 g, 2.62 mmol, 80%) as a white solid. To a stirred solution of the diol intermediate in DCM (26 mL) cooled to 0° C. was added triethylamine (1.1 mL, 7.8 mmol) followed by methanesulfonyl chloride (1.6 mL, 20.9 mmol). The reaction mixture was stirred at 0° C. for 15 min, then at rt for 2 h. After completion of the reaction, water was added, and the reaction mixture was extracted with DCM (3×50 mL). Combined organics were dried over $Na_2SO_4$, filtered, and concentrated. The crude was washed with cold MeOH to afford the desired dimesylate 4 (0.49 g, 1.20 mmol, 45% yield over two steps) as a white solid.

Examples 4-10 can be Prepared Essentially According to Methods Described Herein

Example 4

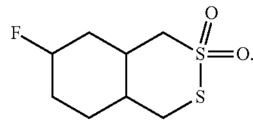

Example 5

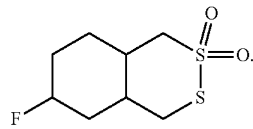

Example 6

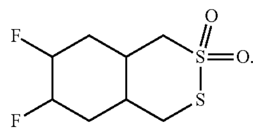

Example 7

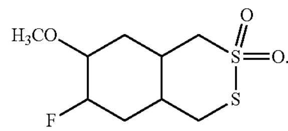

Example 8

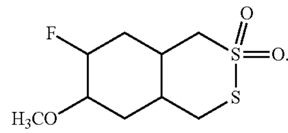

Example 9

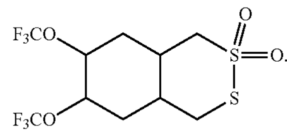

Example 10

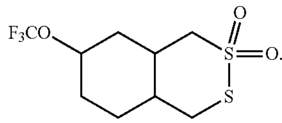

Example 11

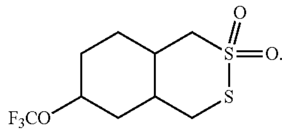

In addition to the aforementioned DDA compounds of the invention (i.e., compounds of the formulae herein, including e.g., Formula I-XI, and salts thereof), other DDA compounds examined include compound NSC322072, (NCI compound library), and compounds TcyDTDO and (±)-DMtcyDTDO as described in WO 2019/241644 (published Dec. 19, 2019).

Example 12—Synthesis of (±)-DMtcyDTDO (as Reproduced from WO 2019/241644)

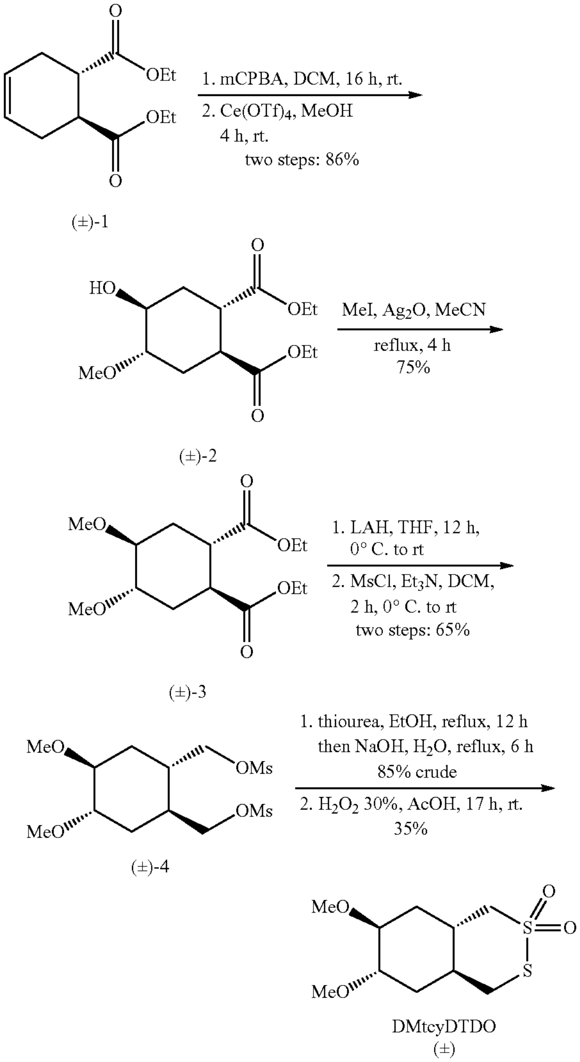

Preparation of Diethyl (1S,2S,4S,5S)- and (1R,2R,4R,5R)-4-hydroxy-5-methoxycyclohexane-1,2-dicarboxylate, (±)-2

MCPBA 77% (6.9 g, 31 mmol) was added to a solution of diester (±)-1 (5.0 g, 22 mmol) in anhydrous DCM (85 mL) at 0° C. The solution then was stirred at rt for 16 h, with monitoring by TLC. After reaction completion, the white precipitate was filtered off and saturated $NaHSO_3$ was then added to the filtrate and stirred for 10 min. The organic layer was separated, washed with $NaHCO_3$, dried over $Na_2SO_4$, and concentrated to give the crude epoxy diester, which was used without further purification in the next step.

Epoxy diester (5.2 g, 22 mmol, 1.0 equiv) was dissolved in dry MeOH (60 mL) then cat. $Ce(OTf)_4$ (0.6 g, 0.9 mmol, 0.04 equiv) was added. The solution was stirred at rt under Ar atmosphere until the starting material was consumed. After completion of the reaction the solvent was evaporated, water was added, and the crude mixture was extracted with DCM. The combined organic layers were dried over $Na_2SO_4$ and concentrated under reduced pressure. The crude material was then purified by flash silica gel column chromatography (0-40% EtOAc/hexanes) to afford the compound (±)-2 (5.2 g, 19 mmol, 86% yield) as a colorless oil. $^1H$ NMR ($CDCl_3$, 400 MHz): δ 4.16-4.05 (m, 4H), 3.86-3.83 (m, 1H), 3.35 (s, 3H), 3.27 (q, J=4.9 Hz, 1H), 3.03 (td, J=10.0, 4.2 Hz, 1H), 2.95 (td, J=9.6, 4.2 Hz, 1H), 2.45 (s, 1H), 2.00-1.93 (m, 2H), 1.89 (dt, J=13.9, 4.7 Hz, 1H), 1.82 (dt, J=13.8, 4.8 Hz, 1H), 1.24-1.17 (m, 6H). $^{13}C$ NMR ($CDCl_3$, 101 MHz): δ 174.6, 78.4, 67.4, 60.8, 56.7, 39.5, 39.2, 30.7, 26.5, 14.2. HRMS calcd for $C_{13}H_{22}O_6[M+H]^+$: 275.1489; found: 275.1492.

Preparation of Diethyl (1S,2S,4S,5S)- and (1R,2R,4R,5R)-4,5-dimethoxycyclohexane-1,2-dicarboxylate, (±)-3

Silver (I) oxide (8.8 g, 38 mmol) was added to a solution of compound (±)-2 (5.2 g, 19 mmol) and iodomethane (11.8 mL, 190 mmol) in acetonitrile (50 mL), then the mixture was heated to reflux for 4 h. After completion of the reaction the solid residue was removed by filtration. An aqueous $NaHCO_3$ solution was added and the reaction mixture was extracted with ethyl acetate, washed with brine, dried over $Na_2SO_4$, and concentrated under reduced pressure. The crude material was purified by flash silica gel column chromatography (0-20% EtOAc/hexanes) to afford the desired product (±)-3 (4.1 g, 14 mmol, 75% yield) as a white solid. $^1H$ NMR ($CDCl_3$, 400 MHz): δ 4.26-4.00 (m, 4H), 3.46-3.42 (m, 2H), 3.36 (s, 6H), 2.92-2.82 (m, 2H), 2.07 (d, J=14.0 Hz, 2H), 1.80-1.69 (m, 2H), 1.22 (t, J=7.1 Hz, 6H). $^{13}C$ NMR ($CDCl_3$, 101 MHz) δ 175.0, 75.4, 60.6, 56.6, 39.0, 27.0, 14.3. HRMS calcd for $C_{14}H_{24}O_6[M+H]^+$: 289.1651; found: 289.1650.

Preparation of ((1S,2S,4S,5S)- and (1R,2R,4R,5R)-4,5-Dimethoxycyclohexane-1,2-diyl)bis(methylene) dimethanesulfonate, (±)-4

To an ice-cooled solution of compound (±)-3 (4.4 g, 15 mmol) in anhydrous THF (85 mL) was added $LiAlH_4$ (1.7 g, 46 mmol) in small portions then the reaction mixture was stirred for 8 h at rt. After this time water was added dropwise, and the white precipitate formed was filtered through celite and washed with DCM. The filtrate was extracted with DCM, and the combined organic extracts were dried over $Na_2SO_4$, filtered, and concentrated to give the diol (2.8 g, 14 mmol, 90% yield) which was used without further purification in the next step.

A solution of the diol (1.5 g, 7.3 mmol) in anhydrous DCM (70 mL) was cooled to 0° C. and treated with triethylamine (4.0 mL, 29 mmol) followed by methanesulfonyl chloride (2.8 mL, 37 mmol). The reaction mixture was stirred at 0° C. for 15 min, then at rt for 2 h. After completion of the reaction, water was added, and the reaction mixture was extracted with DCM (3×50 mL). The combined organic layers were dried over $Na_2SO_4$, filtered, and concentrated. The crude material was purified by flash silica gel column chromatography (0-50% EtOAc/hexanes) to afford the desired dimesylate (±)-4 (1.9 g, 5.3 mmol, 72%) as a pale yellow solid. $^1H$ NMR ($CDCl_3$, 400 MHz) δ 4.26 (dd, J=10.2, 4.1 Hz, 2H), 4.11 (dd, J=10.2, 3.1 Hz, 2H), 3.47-3.43 (m, Hz, 2H), 3.32 (s, 6H), 3.01 (s, 6H), 2.00-1.94 (m, 2H), 1.89-1.74 (m, 2H), 1.72-1.61 (m, 1H). $^{13}C$ NMR ($CDCl_3$, 101 MHz) δ 75.4, 71.7, 56.7, 37.3, 32.5, 27.7. HRMS calcd for $C_{12}H_{24}O_8S_2$ $[M+Na]^+$: 383.0805; found: 383.0805.

Preparation of (4aS,6S,7S,8aS)- and (4aR,6R,7R, 8aR)-6,7-Dimethoxyoctahydrobenzo [d][1,2]dithiine 2,2-dioxide, (±)-DMtcyDTDO Thiourea (0.76 g, 10 mmol) was added to the solution of compound (±)-4 (1.45 g, 4.03 mmol) in EtOH (10 mL) and heated to reflux in an open flask for 8 h. EtOH was then removed under vacuum and the residue was dissolved in $H_2O$ (20 mL) and a solution of NaOH (0.64 g, 16 mmol) in $H_2O$ (6 mL) was added. The mixture was heated to reflux for 6 h, cooled to rt, acidified with HCl, and extracted with DCM. The combined organic extracts were dried over $Na_2SO_4$ and evaporated to afford (±)-(4,5-dimethoxycyclohexane-1,2-diyl)dimethanethiol as a pale yellow oil (0.8 g, 3 mmol, 85% yield). which was used without further purification for the next step.

To an ice-cooled solution of the crude dithiol (0.8 g, 3 mmol) in AcOH (5.0 mL) was added a solution of $H_2O_2$ in AcOH (0.9 mL of aqueous 30% $H_2O_2$ diluted in 1.5 mL of AcOH, 9 mmol of $H_2O_2$) and stirred under nitrogen, monitoring by TLC. After stirring for 17 h, the solvent was removed under vacuum, and the residue was diluted with water, neutralized with $NaHCO_3$, and extracted with $CHCl_3$. The organic extract was dried with $Na_2SO_4$, filtered, and the solvent was removed under vacuum. The crude material was purified by column chromatography (10-40% EtOAc/hexanes) to afford the desired product (±)-DMtcyDTDO (0.32 g, 1.2 mmol, 35% yield) as a white solid. $^1H$ NMR ($CDCl_3$, 400 MHz): δ 3.50 (q, J=2.8 Hz, 1H), 3.43 (q, J=2.8 Hz, 1H), 3.35 (s, 3H), 3.34 (s, 3H), 3.30 (dd, J=14.2, 11.7 Hz, 1H), 3.23-3.10 (m, 2H), 2.82 (dd, J=14.2, 2.9 Hz, 1H), 2.44 (qt, J=11.8, 3.8 Hz, 1H), 1.92 (qt, J=11.6, 3.2 Hz, 1H), 1.80 (dt, J=13.8, 3.0 Hz, 1H), 1.67 (dt, J=13.8, 3.1 Hz, 1H), 1.62-1.47 (m, 2H). $^{13}C$ NMR ($CDCl_3$, 101 MHz) δ 76.2, 74.4, 64.4, 56.8, 56.8, 39.8, 35.9, 35.6, 31.1, 30.1. HRMS calcd for $C_{10}H_{18}O_4S_2$ $[M+Na]^+$: 289.0539; found: 289.0527.

Example 13. Synthesis of (±)-dFtcyDTDO, (±)-FMtcyDTDO1, and (±)-FMtcyDTDO2

The pathway to generate difluorinated derivative dFtcyDTDO is outlined in Scheme 6. The synthesis starts with epoxidation of the double bond on the cyclohexene diester (±)-1 using mCPBA. Treatment of the epoxide with $Et_3N$-3HF as a source of nucleophilic fluoride provides hydrofluorinated compound 2 as a single stereoisomer in 85% yield. Compound 3 is obtained by inverting the stereochemistry of the hydroxyl group on compound 2. This is achieved by triflation of the hydroxy group followed by displacement using tetrabutylammonium benzoate and subsequent cleavage of the benzoyl group under basic conditions to provide the fluorohydrin 3. Installation of the second fluorine is achieved by triflation followed by treatment with $Et_3N$-3HF to furnish compound 4. Ester reduction using lithium aluminum hydride provides the dihydroxy intermediate that is mesylated to give compound 5. Thioacetate substitution followed by acetyl cleavage furnishes the dithiol that is oxidized to disulfide 6. Ultimately, oxidation of 6 using mCPBA affords dFtcyDTDO.

Scheme 6.

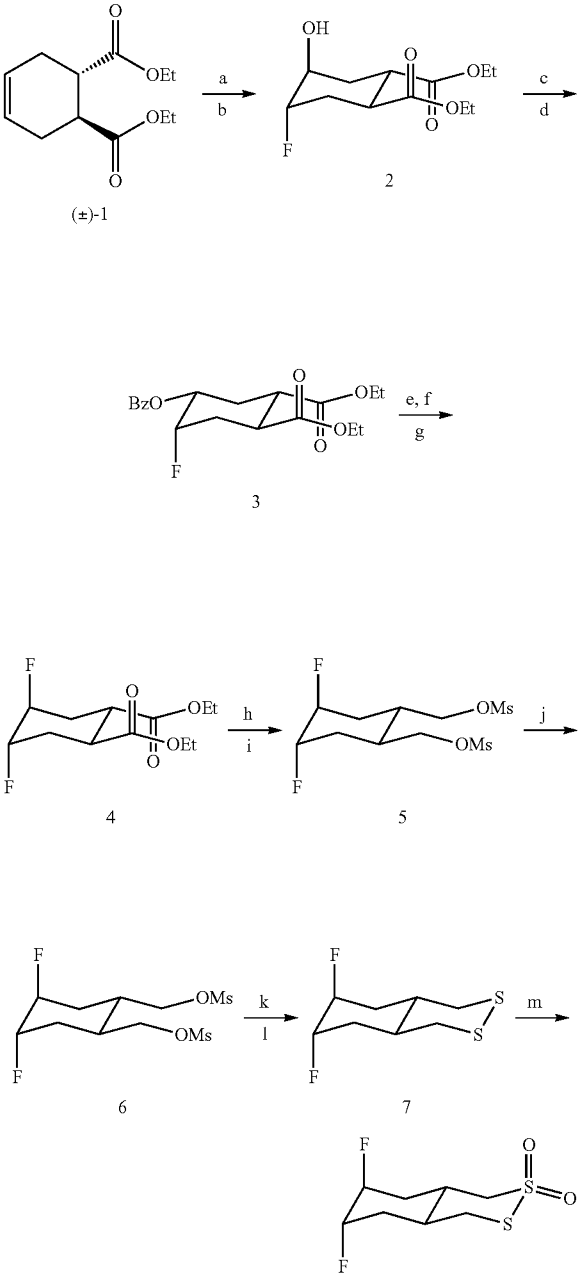

(±)-dFtcyDTDO

Pathway to (4aS,6S,7S,8aS)- and (4aR,6R,7R,8aR)-6,7-difluorooctahydrobenzo[d][1,2]dithiine 2,2-dioxide, (±)-dFtcyDTDO. a) mCPBA, DCM, 16 h, 0° C. to rt; b) $Et_3N$•3HF, 55° C., 2 days, two steps, 90%; c) $Tf_2O$, pyridine, DCM, 2 h, 0° C. to rt;, d) $(Bu)_4N^+BzO^-$, toluene, 6 h, rt, two steps, 54%; e) NaOEt, EtOH, 4 h, rt, 86%; f) $Tf_2O$, pyridine, DCM, 2 h, 0° C. to rt, 92;% g) $Et_3N$•3HF, 2 days, 65° C., 36%; h) $LiAlH_4$, THF, 12 h, 0° C. to rt, 87%; i) MsCl, $Et_3N$, DCM, 0° C. to rt, 77%; j) KSAc, 18-crown-6, DMF, 48 h, rt, 57%; k) $LiAlH_4$, THF, 3 h, 0° C. to rt; l) $SiO_2$, $Br_2$, $H_2O$, DCM, 10 min, rt, two steps, 37%; m) mCPBA, DCM, 2 h, 0° C. to rt, 33%.

Methylation of the hydroxy group of compound 2 using an excess of methyl iodide in the presence of silver(I) oxide affords trans-dimethoxy intermediate 8 (Scheme 7). Then, similar synthetic approaches provide DDA derivatives FMtcyDTDO1 and FMtcyDTDO2.

Scheme 7. Synthesis of (4aS,6S,7S,8aS)- and (4aR,6R,7R,8aR)-6-fluoro-7-methoxyoctahydrobenzo[d][1,2]dithiine 2,2-dioxide, (±)-FMtcyDTDO1 and (4aS,6S,7S,8aS)- and (4aR,6R,7R,8aR)-7- fluoro-6-methoxyoctahydrobenzo[d][1,2]dithiine 2,2-dioxide, (±)-FMtcyDTDO2. a) MeI, $Ag_2O$, MeCN, 4 h, reflux, 70%; b) $LiAlH_4$, THF, 12 h, 0° C. to rt; c) MsCl, $Et_3N$, DCM, 0° C. to rt, two steps, 61%; d) KSAc, 18-crown-6, DMF, 48 h, rt, 66%; e) $LiAlH_4$, THF, 3 h, 0° C. to rt; f) $SiO_2$, $Br_2$, $H_2O$, DCM, 10 min, rt, crude two steps, 46%; g) mCPBA, DCM, 2 h, 0° C. to rt, 18% (±)-FMtcyDTDO1 and 14% (±)-FMtcyDTDO2.

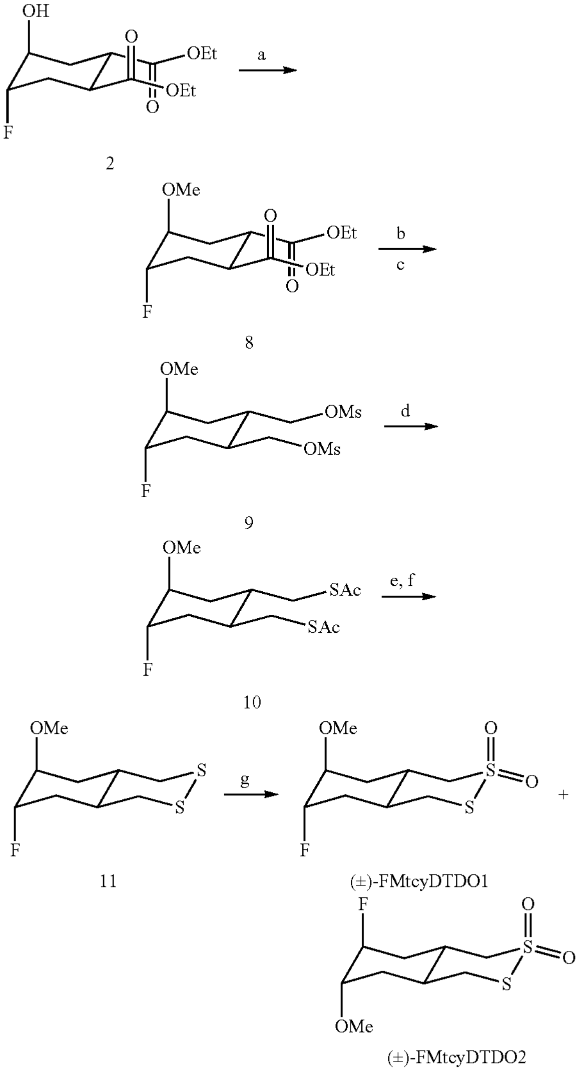

2

8

9

10

11

(±)-FMtcyDTDO1

(±)-FMtcyDTDO2

Experimental Details for the Syntheses of (±)-dFtcyDTDO, (±)-FMtcyDTDO1, and (±)-FMtcyDTDO2: General Methods Reagents and solvents were purchased from commercial sources and used without further purification unless otherwise specified. Anhydrous solvents were obtained using a commercial solvent drying system (using activated alumina for THF, dichloromethane) and transferred via syringe to flame-dried glassware that had been cooled under an argon or nitrogen atmosphere. $^1H$ and $^{13}C$ NMR spectra were recorded using commercially-obtained deuterated solvents on Bruker-400 ($^1H$ at 400 MHz; $^{13}C$ at 101 MHz) spectrometer. Chemical shifts (δ) are given in parts per million (ppm) relative to TMS and referenced to residual protonated solvent ($CDCl_3$: $\delta_H$ 7.26 ppm, $\delta_C$ 77.16 ppm; $CD_3OD$: $\delta_H$ 4.87 ppm, $\delta_C$ 49.00 ppm; DMSO-$d_6$: $\delta_H$ 2.50 ppm, $\delta_C$ 39.52 ppm; $D_2O$: $\delta_H$ 4.79 ppm). Coupling constants (J) are reported in Hz. Spin multiplicities are presented by the following symbols: s (singlet), bs (broad singlet), d (doublet), t (triplet), q (quartet), p (pentet), and m (multiplet). Electrospray ionization (ESI) high-resolution mass spectra (HRMS) were recorded on an Agilent 6230 ESI-TOF instrument, operating in positive or negative ion mode as stated, with methanol as the carrier solvent.

Synthesis of (±)-dFtcyDTDO Diethyl (1S,2S,4S,5S)- and (1R,2R,4R,5R)-4-fluoro-5-hydroxycyclohexane-1,2-dicarboxylate, (±)-2

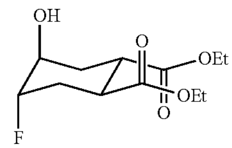

2

MCPBA 77% (6.9 g, 31 mmol) was added to a solution of diester (±)-1 (5.0 g, 22 mmol) in anhydrous DCM (85 mL) at 0° C. The solution then was stirred at rt for 16 hours, monitoring by TLC. After reaction completion, the white precipitate was filtered off and saturated $NaHSO_3$ was then added to the filtrate and stirred for 10 min. The organic layer was separated, washed with $NaHCO_3$, dried over $Na_2SO_4$, and concentrated to give the crude epoxy diester (7.4 g, 31 mmol), which was used without further purification in the next step.

Epoxy diester (5.0 g, 21 mmol) was added to triethylamine trihydrofluoride (14 mL, 4.0 mmol) and stirred for 48 hours under nitrogen at 50° C. After full consumption of the epoxy diester, sat. $NaHCO_3$ solution was added until all the HF was neutralized and then extracted by EtOAc. Combined organic layers were washed with $NaHCO_3$ and brine, dried over $Na_2SO_4$, filtered, and concentrated. The mixture was purified by flash chromatography on silica (0-30% EtOAc/hexanes) to afford the desired 2 (4.9 g, 19 mmol, 90%) as a pale-yellow oil. $^1H$ NMR ($CDCl_3$, 600 MHz): δ 4.61 (dq, J=47.1, 4.5 Hz, 1H), 4.18-4.10 (m, 4H), 4.05-3.99 (m, 1H), 3.07 (td, J=9.9, 4.1 Hz, 1H), 3.01 (td, J=9.7, 4.7 Hz, 1H), 2.15-1.98 (m, 3H), 1.94 (dt, J=9.6, 4.5 Hz, 1H), 1.28-1.22 (m, 6H). $^{13}C$ NMR ($CDCl_3$, 151 MHz): δ 174.32, 174.12, 89.61 (d, J=173.6 Hz), 66.57 (d, J=26.4 Hz), 61.04, 61.01, 39.51 (d, J=3.3 Hz), 38.92, 30.56, 28.34 (d, J=20.4 Hz), 14.25. HRMS calcd for $C_{12}H_{19}FO_5$ $[M+Na]^+$: 285.1109; found: 285.1110.

Diethyl (1S,2S,4S,5S)- and (1R,2R,4R,5R)-4-(benzoyloxy)-5-fluorocyclohexane-1,2-dicarboxylate, (±)-3

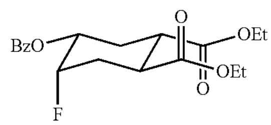

3

Pyridine (3.5 mL, 44 mmol) and compound 2 (6.0 g, 23 mmol) in dry DCM (35 mL) was added drop wise over a period of 10 minutes to a solution of trifluoromethanesulfonic anhydride (7.3 mL, 44 mmol) in dry DCM (35 mL) previously stirred for 10 minutes at 0° C. under Ar. The reaction mixture was stirred for 30 minutes at 0° C. and then stirred at room temperature. After reaction completion as evident by TLC, DCM was added and quenched with adding ice-cold water. The organic solution was washed with ice-cold water, dried over $MgSO_4$, filtered and the solvent removed in vacuo, to give the crude as a light brown oil (8.7 g, 22 mmol) the freshly provided crude was then used as is for the next step. $^1H$ NMR ($CDCl_3$, 400 MHz) δ 5.11-5.04 (m, 1H), 4.79 (dq, J=46.9, 5.5 Hz, 1H), 4.23-4.12 (m, 4H), 3.14-3.04 (m, 2H), 2.37-2.26 (m, 1H), 2.24-2.11 (m, 3H), 1.42-1.11 (m, 6H). $^{13}C$ NMR ($CDCl_3$, 101 MHz): δ 172.6, 172.3, 118.5 (q, J=319.6 Hz), 86.4 (d, J=178.3 Hz), 82.6 (d, J=28.2 Hz), 61.6, 61.5, 39.4, 39.2 (d, J=4.9 Hz), 28.7, 28.45 (d, J=20.4 Hz) 14.2, 14.1. HRMS calcd for $C_{13}H_{18}F_4O_7S$ $[M+H]^+$: 395.0782; found: 395.0791.

Tetrabutylammonium benzoate (15.0 g, 41.1 mmol) was added to the solution of freshly provided crude (8.1 g, 21 mmol) in anhydrous toluene (300 mL) and stirred under Ar for 2 h. After completion of the reaction, as evident by TLC, the solvent was removed in vacuo added DCM and washed with water and dried over $Na_2SO_4$. The product was purified by flash column chromatography on silica (0-10% EtOAc/hexanes) to give the title compound 3 as a colorless oil (4.10 g, 11.2 mmol, 54%). $^1H$ NMR ($CDCl_3$, 400 MHz) δ 8.06 (dd, J=8.3, 1.2 Hz, 2H), 7.58 (tt, J=7.0, 1.3 Hz, 1H), 7.44 (t, J=7.7 Hz, 2H), 5.15-4.93 (m, 2H), 4.21-4.08 (m, 4H), 3.09 (td, J=12.2, 4.1 Hz, 1H), 2.90 (td, J=11.5, 3.6 Hz, 1H), 2.52 (ddt, J=14.6, 8.6, 4.4 Hz, 1H), 2.30 (dt, J=12.4, 4.6 Hz, 1H), 2.14 (q, J=11.7 Hz, 1H), 1.79 (dt, J=38.7, 12.9 Hz, 1H), 1.30-1.20 (m, 6H). $^{13}C$ NMR ($CDCl_3$, 101 MHz): δ 173.9, 172.9, 165.8, 133.5, 130.0, 129.7, 128.6, 87.33 (d, J=178.7 Hz), 71.70 (d, J=17.8 Hz), 61.2, 42.7, 38.7, 31.74 (d, J=21.0 Hz), 27.5, 14.3, 14.2. HRMS calcd for $C_{19}H_{23}FO_6$ $[M+Na]^+$: 389.1371; found: 389.1375.

Diethyl (1S,2S,4S,5S) and (1R,2R,4R,5R)-4,5-difluorocyclohexane-1,2-dicarboxylate, (±)-4

4

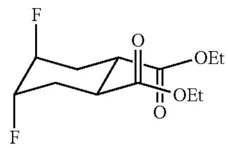

NaOEt (1.3 mL of 21% NaOEt in EtOH, 3.6 mmol) was added to the solution of benzoate intermediate (3.3 g, 8.9 mmol) in ethanol (90 mL) and stirred under nitrogen. After completion of the reaction, as evident by TLC, pH 7.4 phosphate buffer silane was added until pH gets close to neutral, then ethanol was removed under vacuum. The aqueous solution was extracted with EtOAc, then combined organic extracts were washed with sat. $NaHCO_3$ and brine, then dried over $NaSO_4$, filtered, and evaporated. The crude was purified by flash column chromatography on silica (0-40% EtOAc/hexanes) to give the product as colorless oil (2.0 g, 7.6 mmol, 86%). $^1H$ NMR ($CDCl_3$, 400 MHz) δ 4.80 (d, J=50.3 Hz, 1H), 4.16-4.03 (m, 4H), 3.63 (dddd, J=27.6, 11.5, 4.5, 1.8 Hz, 1H), 2.89 (td, J=12.3, 4.1 Hz, 1H), 2.77 (bs, 1H), 2.69 (td, J=12.0, 3.7 Hz, 1H), 2.39 (ddd, J=18.9, 8.4, 4.2 Hz, 1H), 2.12 (dt, J=12.7, 4.2 Hz, 1H), 1.74 (q, J=12.4 Hz, 1H), 1.58 (dt, J=42.0, 13.1 Hz, 1H), 1.2-1.17 (m, 6H). $^{13}C$ NMR ($CDCl_3$, 101 MHz): δ 174.1, 173.2, 89.97 (d, J=174.0 Hz), 69.51 (d, J=19.2 Hz), 60.9, 43.0, 38.6, 31.61 (d, J=20.8 Hz), 30.85 (d, J=3.3 Hz), 14.1. HRMS calcd for $C_{12}H_{19}FO_5$ $[M+Na]^+$: 285.1109; found: 285.1095.

A mixture of pyridine (1.3 mL, 16 mmol) and hydroxy intermediate (2.4 g, 9.1 mmol) in dry DCM (15 mL) was added drop wise over a period of 10 minutes to a solution of trifluoromethanesulfonic anhydride (3.0 mL, 18 mmol) in dry DCM (15 mL) at 0° C. under Ar. The reaction mixture was stirred for 30 minutes at 0° C. and then stirred at room temperature. After reaction completion as evident by TLC, DCM was added and quenched with adding ice cold water. The organic solution was washed with ice cold water, dried over $MgSO_4$, filtered and the solvent removed in vacuo, to give the crude as a light brown oil (3.3 g, 8.4 mmol, 92%) that was used as is for the next step. $^1H$ NMR ($CDCl_3$, 400 MHz) δ 5.14-4.73 (m, 2H), 4.25-3.95 (m, 4H), 3.03 (td, J=11.7, 4.2 Hz, 1H), 2.85 (td, J=10.8, 4.2 Hz, 1H), 2.50 (ddt, J=14.8, 8.0, 4.8 Hz, 1H), 2.40-2.17 (m, 2H), 1.77 (dt, J=37.9, 13.5 Hz, 1H), 1.40-1.09 (m, 2H). $^{13}C$ NMR ($CDCl_3$, 101 MHz): δ 173.1, 171.7, 118.5 (q, J=319.3 Hz), 86.6 (d, J=183.1 Hz), 84.7 (d, J=18.4 Hz), 61.6, 61.4, 42.2, 38.1, 31.1 (d, J=20.7 Hz), 28.3 (d, J=2.8 Hz), 14.2, 14.1. HRMS calcd for $C_{13}H_{18}F_4O_7S$ $[M+Na]^+$: 417.0602; found: 417.0612.

The triflate intermediate (3.3 g, 8.4 mmol) was added to triethylamine trihydrofluoride (5.8 mL, 50 mmol) and stirred for 24 hours under Ar at 65° C. After full consumption of the triflate, sat. $NaHCO_3$ solution was added until all the HF was neutralized and then extracted by DCM. Combined organic layers were washed with $NaHCO_3$ and brine, dried over $Na_2SO_4$, filtered, and concentrated. The mixture was purified by flash chromatography on silica (0-5% EtOAc/hexanes) to afford the desired 4 (0.8 g, 3 mmol, 36%) as a colorless oil. $^1H$ NMR ($CDCl_3$, 400 MHz) δ 4.80 (d, J=47.5 Hz, 2H), 4.31-3.99 (m, 4H), 3.16-2.85 (m, 2H), 2.36-2.15 (m, 2H), 2.08-1.80 (m, 2H), 1.41-1.10 (m, 6H). $^{13}C$ NMR ($CDCl_3$, 101 MHz): δ 173.7, 85.9 (dd, J=173.7, 32.0 Hz), 61.1, 38.9, 28.6 (dd, J=12.8, 7.5 Hz), 14.2. HRMS calcd for $C_{12}H_{18}F_2O_4$ $[M+Na]^+$: 287.1065; found: 287.1063.

(1S,2S,4S,5S)- and (1R,2R,4R,5R)4,5-Difluorocyclohexane-1,2-diyl)bis(methylene) dimethanesulfonate, (±)-5

5

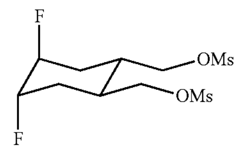

To an ice-cooled solution of compound 4 (0.8 g, 3 mmol) in anhydrous THF (15 mL) was added $LiAlH_4$ (0.3 g, 9 mmol) in small portions then the reaction mixture was stirred under Ar atmosphere for 8 hours at rt. After this time water was added dropwise, and the white precipitate filtered off and washed with DCM. The filtrate extracted with DCM (5×15 mL), the combined organic extracts were dried over $Na_2SO_4$, filtered, and concentrated to give the diol (0.45 g, 2.5 mmol, 87% yield) as a white powder which was used without further purification for the next step. $^1H$ NMR (methanol-$d_4$, 400 MHz) δ 4.77 (d, J=51.8 Hz, 2H), 3.68-3.46 (m, 4H), 2.01-1.91 (m, 2H), 1.88-1.58 (m, 6H). $^{13}$C NMR (Methanol-$d_4$, 101 MHz) δ 88.8 (dd, J=170.3, 31.5 Hz), 64.9, 36.5, 30.5-30.2 (m). HRMS calcd for $C_{82}H_{14}F_2O_2$ $[M+H]^+$: 181.1035; found: 181.1037.

A solution of the diol (0.45 g, 2.5 mmol) in anhydrous DCM (9 mL) was cooled to 0° C. and added triethylamine (1.0 mL, 7.5 mmol) followed by methanesulfonyl chloride (1.5 mL, 20.0 mmol). The reaction mixture was stirred at 0° C. for 15 min, then at rt for 2 h. After completion of the reaction, water was added, and the reaction mixture was extracted with DCM. Combined organics were dried over $Na_2SO_4$, filtered, and concentrated. The crude was purified by flash silica gel column chromatography (20-60% EtOAc/hexanes) and then recrystallized in methanol to afford the desired dimesylate 5 (0.65 g, 1.9 mmol, 77%) as a crystalline white solid. $^1$H NMR ($CDCl_3$, 400 MHz) δ 4.84 (d, J=46.2 Hz, 2H), 4.36 (dd, J=10.4, 3.6 Hz, 2H), 4.16 (dd, J=10.4, 2.6 Hz, 2H), 3.04 (s, 6H), 2.16-2.01 (m, 4H), 2.00-1.73 (m, 2H). $^{13}$C NMR ($CDCl_3$, 101 MHz) δ 86.0 (dd, J=171.6, 33.4 Hz), 70.4, 37.4, 31.9, 30.2-28.7 (m). HRMS calcd for $C_{10}H_{18}F_2O_6S_2[M+Na]^+$: 359.0405; found: 359.0395.

S,S'-(((1S,2S,4S,5S)- and (((1R,2R,4R,5R)-4,5-difluorocyclohexane-1,2-diyl)bis (methylene))di-ethanethioate, (±)-6

6

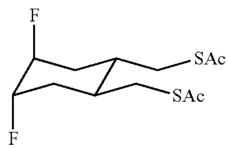

A mixture of the dimesylate 5 (0.1 g, 0.3 mmol), KSAc (70 mg, 0.6 mmol), and 18-crown-6 (25 mol %) in anhydrous DMF (6 mL) was stirred for 24 h at room temperature. After this time DMF was evaporated, water added, and the mixture was extracted with DCM (3×50 mL). The combined organic phases were washed with water and brine, dried over $Na_2SO_4$, concentrated, and purified by column chromatography (0-10% hex/EtOAc) to afford the dithioacetate 6 (54 mg, 0.17 mmol, 57%). $^1$H NMR ($CDCl_3$, 400 MHz) δ 4.75 (d, J=46.7 Hz, 2H), 3.23 (dd, J=13.9, 2.9 Hz, 2H), 2.85 (dd, J=13.9, 7.0 Hz, 2H), 2.36 (s, 6H), 2.12-2.00 (m, 2H), 1.90-1.79 (m, 2H), 1.73-1.50 (m, 2H). $^{13}$C NMR ($CDCl_3$, 101 MHz) δ 195.3, 86.7 (dd, J=171.7, 32.9 Hz), 34.7, 32.1, 31.1-30.8 (m), 30.8. HRMS calcd for $C_{12}H_{18}F_2O_2S_2$ $[M+H]^+$: 297.0789; found: 297.0799.

(4aS,6S,7S,8aS) and (4aR,6R,7R,8aR)-6,7-Difluorooctahydrobenzo[d][1,2]dithiine, (±)-7

7

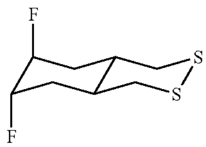

To an ice-cooled solution of the dithioacetate 6 (0.15 g, 0.51 mmol) in anhydrous THF (5 mL) was added $LiAlH_4$ (43.0 mg 1.13 mmol). The reaction mixture was stirred for 3 hours at rt and quenched with dropwise addition of water. The white precipitated was filtered off and washed with DCM. The filtrate was then extracted with DCM, the combined organic extracts used for the next step.

Silica gel (40-60 μm particle size, 60 Å pore size, 1.25 g) was added to a round bottom flask and DI water (2.55 mL) was added with vigorous stirring until a uniform suspension was formed. Then the solution of dithiol in DCM (30 mL) from previous step was added to the suspension while stirring. A solution of $Br_2$ (89.4 mg, 0.56 mmol) in DCM (1 mL) was added dropwise to the suspension while stirring. The reaction was stopped after stirring for 10 minutes, monitoring by TLC. Silica was filtered off into a flask containing a stirred solution of 2 M NaOH (10 mL). The organic phase was separated, washed with water, and dried over $Na_2SO_4$. The solvent was evaporated under vacuum to give the crude product as a pale-yellow solid (40 mg, 0.19 mmol, 37%) that was used as is for the next step. $^1$H NMR ($CDCl_3$, 600 MHz): δ 4.78 (d, J=46.1 Hz, 2H), 2.78 (dd, J=14.1, 10.4 Hz, 2H), 2.57 (dd, J=13.6, 2.7 Hz, 2H), 1.97-1.89 (m, 2H), 1.88-1.81 (m, 2H), 1.72-1.56 (m, 2H). $^{13}$C NMR ($CDCl_3$, 151 MHz) δ 86.6 (dd, J=171.1, 34.0 Hz), 38.9, 37.6, 33.8-33.2 (m).

(4aS,6S,7S,8aS)- and (4aR,6R,7R,8aR)-6,7-Difluorooctahydrobenzo[d][1,2]dithiine 2,2-dioxide, (±)-dFtcyDTDO

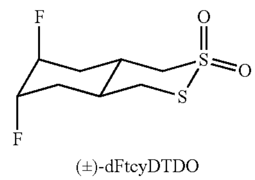 [SMILES: O=S1(=O)CC2CC(F)C(F)CC2CS1]

(±)-dFtcyDTDO

To an ice-cooled solution of the crude disulfide (42 mg, 0.20 mmol) in DCM (4.0 mL) was added mCPBA (94 mg, 0.42 mmol, 2.2 equiv) and let it stir monitoring by TLC. After reaction (±)-dFtcyDTDO completion, saturated $NaHSO_3$ was added to the reaction mixture and stirred for 10 min. The organic layer was separated, washed with $NaHCO_3$, dried over $Na_2SO_4$, and concentrated to give the crude. The crude material was purified by column chromatography (0-30% EtOAc/hexanes) to afford the product (±)-dFtcyDTDO (16 mg, 0.070 mmol, 33% yield) as a white solid. $^1$H NMR ($CDCl_3$, 600 MHz): δ 4.89 (d, J=43.3 Hz, 1H), 4.81 (d, J=43.9 Hz, 1H). 3.36 (dd, J=13.1, 11.5 Hz, 1H), 3.29-3.16 (m, 2H), 2.91 (dd, J=14.3, 2.9 Hz, 1H), 2.62-2.52 (m, 1H), 2.13-1.99 (m, 2H), 1.98-1.90 (m, 1H), 1.84-1.61 (m, 2H). $^{13}$C NMR ($CDCl_3$, 151 MHz) δ 86.0 (dd, J=227.2, 32.6 Hz), δ 84.9 (dd, J=228.1, 32.3 Hz), 63.8, 39.3, 35.4, 35.3, 32.7 (d, J=20.5 Hz), 31.6 (d, J=20.5 Hz). HRMS calcd for $C_8H_{12}F_2O_2S_2[M+NH_4]^+$: 260.0585; found: 260.0595.

Synthesis of (±)-FMtcyDTDO1 and (±)-FMtcyDTDO2

Diethyl (1S,2S,4S,5S)- and (1R,2R,4R,5R)-4-Fluoro-5-methoxycyclohexane-1,2-dicarboxylate, (±)-8

8

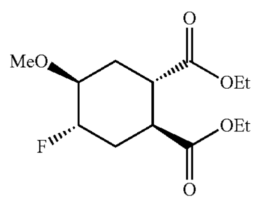

Silver(I) oxide (15.4 g, 66.3 mmol) was added to a solution of compound (±)-2 (8.7 g, 33 mmol) and iodomethane (16.5 mL, 265 mmol) in acetonitrile (90 mL), then the mixture refluxed for 4 h. After completion of the reaction the solid residue was removed by filtration. An aqueous $NaHCO_3$ solution was added and the reaction mixture was extracted with ethyl acetate, washed with brine, dried over $Na_2SO_4$ and concentrated under reduced pressure. The crude was purified by flash silica gel column chromatography (0-20% EtOAc/hexanes) to afford the desired product 8 (6.5 g, 23.5 mmol, 70% yield) as a colorless oil. $^1$H NMR ($CDCl_3$, 600 MHz): δ 4.66 (dq, J=46.6, 2.2 Hz, 1H), 4.17-4.03 (m, 4H), 3.50 (p, J=3.7 Hz, 1H), 3.35 (s, 3H), 2.97-2.82 (m, 2H), 2.17-2.05 (m, 2H), 1.85 (dt, J=43.2, 12.3 Hz, 1H), 1.77-1.70 (m, 1H), 1.25-1.16 (m, 6H). $^{13}$C NMR ($CDCl_3$, 151 MHz) δ 174.4, 174.1, 87.1 (d, J=172.5 Hz), 74.6 (d, J=26.5 Hz), 60.7, 57.0, 39.0, 38.7, 28.7 (d, J=20.5 Hz), 26.9, 14.2, 14.1.

((1S,2S,4S,5S)- and (1R,2R,4R,5R)-4-Fluoro-5-methoxycyclohexane-1,2-diyl)bis(methylene) dimethanesulfonate, (±)-9

9

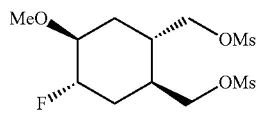

To an ice-cooled solution of compound 8 (4.3 g, 15 mmol) in anhydrous THF (50 mL) was added $LiAlH_4$ (1.3 g, 34 mmol) in small portions then the reaction mixture was refluxed for 8 hours. After this time water was added dropwise, and the white precipitate filtered off through celite and washed with DCM. The filtrate extracted with DCM, the combined organic extracts were dried over $Na_2SO_4$, filtered, and concentrated to give the diol, which was used without further purification for the next step.

A solution of the diol (3.0 g, 16 mmol) in anhydrous DCM (150 mL) was cooled to 0° C. and added triethylamine (8.7 mL, 62 mmol) followed by methanesulfonyl chloride (7.2 mL, 94 mmol). The reaction mixture was stirred at 0° C. for 15 min, then at rt for 2 h. After completion of the reaction, water was added, and the reaction mixture was extracted with DCM. Combined organics were dried over $Na_2SO_4$, filtered, and concentrated. The crude was purified by flash silica gel column chromatography (0-50% EtOAc/hexanes) to afford the desired dimesylate 9 (2.8 g, 8.0 mmol, 51%) as a colorless oil. $^1$H NMR ($CDCl_3$, 600 MHz) δ 4.72 (d, J=46.6 Hz, 1H), 4.30-4.25 (m, 2H), 4.11 (td, J=10.1, 3.2 Hz, 2H), 3.53 (p, J=3.7 Hz, 1H), 3.32 (s, 3H), 3.00 (s, 6H), 2.06-1.99 (m, 2H), 1.96-1.86 (m, 2H), 1.86-1.73 (m, 1H), 1.71-1.62 (m, 1H). $^{13}$C NMR ($CDCl_3$, 151 MHz) δ 87.25 (d, J=170.8 Hz), 74.72 (d, J=27.6 Hz), 71.2, 70.9, 57.0, 37.2, 37.1, 32.4, 31.9, 29.21 (d, J=20.5 Hz), 27.6. HRMS calcd for $C_{11}H_{21}FO_7S_2[M+Na]^+$: 371.0605; found: 371.0620.

S,S'-(((1S,2S,4S,5S)- and (1R,2R,4R,5R)-4-Fluoro-5-methoxycyclohexane-1,2-diyl)bis(methylene)) diethanethioate, (±)-10

10

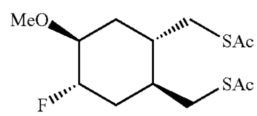

A mixture of the dimesylate 9 (2.7 g, 7.8 mmol), KSAc (2.2 g, 19 mmol), and 18-crown-6 (25 mol %) in anhydrous DMF (120 mL) was stirred for 24 h at room temperature. After this time DMF was evaporated, water added, and the mixture was extracted with DCM. The combined organic phases were washed with water and brine, dried over $Na_2SO_4$, concentrated, and purified by column chromatography (0-20% hex/EtOAc) to afford the dithioacetate 10 (1.7 g, 5.5 mmol, 71%) as orange oil. $^1$H NMR ($CDCl_3$, 600 MHz) δ 4.60 (d, J=46.8 Hz, 1H), 3.42 (p, J=3.5 Hz, 1H), 3.27 (s, 3H), 3.18-3.10 (m, 2H), 2.80-2.71 (m, 2H), 2.29 (s, 3H), 2.28 (s, 3H), 1.96-1.80 (m, 2H), 1.78-1.63 (m, 2H), 1.59-1.44 (m, 1H), 1.49-1.35 (m, 1H). ($CDCl_3$, 151 MHz) δ 195.12, 88.1 (d, J=170.8 Hz), 75.4 (d, J=26.5 Hz), 56.8, 35.1, 34.6, 32.3, 32.2, 31.0 (d, J=19.9 Hz), 30.6, 29.3.

(4aS,6S,7S,8aS)- and (4aR,6R,7R,8aR)-6-Fluoro-7-methoxyoctahydrobenzo[d][1,2]dithiine, (±)-11

11

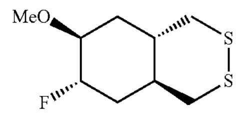

To an ice-cooled solution of the dithioacetate 10 (0.90 g, 2.8 mmol) in anhydrous THF (30 mL) was added $LiAlH_4$ (0.24 g, 6.2 mmol). The reaction mixture was stirred for 3 hours at rt and quenched with dropwise addition of water. The white precipitated was filtered off and washed with DCM. The filtrate extracted with DCM, the combined organic extracts was used for the next step.

The solution of dithiol in DCM (30 mL) from previous step was added to the suspension of silica gel (40-60 μm particle size, 60 Å pore size, 6.9 g) and water (17 mL) with vigorous stirring. A solution of $Br_2$ (0.16 mL, 3.0 mmol) in DCM (1 mL) was added dropwise to the suspension while stirring. The reaction was stopped after stirring for 10 minutes, monitoring by TLC. Silica was filtered off into a flask containing a stirred solution of 2 M NaOH (10 mL). The organic phase was separated, washed with water, and dried over $Na_2SO_4$. The solvent was evaporated under vacuum to give the crude product as a pale-yellow solid (0.29 g, 1.3 mmol, 46%) that was used as is for the next step. $^1$H NMR ($CDCl_3$, 600 MHz): 4.70 (d, J=43.2 Hz, 1H), 3.52 (p, J=3.2 Hz, 1H), 3.36 (s, 3H), 2.75 (ddd, J=13.6, 10.8, 7.0 Hz, 2H), 2.52 (dt, J=13.5, 2.7 Hz, 2H), 1.92-1.81 (m, 2H), 1.78-1.46 (m, 4H). $^{13}$C NMR (151 MHz, $CDCl_3$) δ 88.0 (d, J=170.3 Hz), 75.7 (d, J=28.2 Hz), 57.1, 39.2, 39.0, 38.1, 37.6, 33.5 (d, J=20.5 Hz), 32.0.

(4aS,6S,7S,8aS)- and (4aR,6R,7R,8aR)-6-Fluoro-7-methoxyoctahydrobenzo[d][1,2] dithiine 2,2-dioxide (4aS,6S,7S,8aS), (±)-FMtcyDTDO1, and (4aS,6S,7S,8aS)- and (4aR,6R,7R,8aR)-7-Fluoro-6-methoxyoctahydrobenzo[d][1,2]dithiine 2,2-dioxide, (±)-FMtcyDTDO2

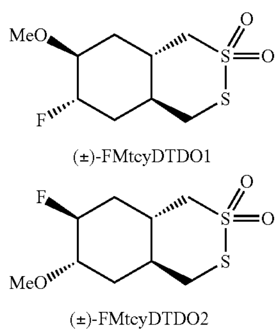

(±)-FMtcyDTDO1

(±)-FMtcyDTDO2

To an ice-cooled solution of the crude disulfide 11 (0.1 g, 0.5 mmol) in DCM (10 mL) was added mCPBA (0.24 g, 1.1 mmol, 2.1 equiv) and the solution was let to stir with monitoring by TLC. After reaction completion, saturated $NaHSO_3$ was added to the reaction mixture and stirred for 5 min. The organic layer was separated, washed with $NaHCO_3$, dried over $Na_2SO_4$, and concentrated to give the crude. The crude material was purified by column chromatography (0-20% EtOAc/hexanes) to afford the products (±)-FMtcyDTDO1 (23 mg, 0.9 mmol, 18% yield) and (±)-FMtcyDTDO2 (17 mg, 0.7 mmol, 14% yield) as a white solid.

(±)-FMtcyDTDO1: $^1$H NMR ($CDCl_3$, 600 MHz) δ 4.78 (d, J=46.7 Hz, 1H), 3.54 (p, J=3.4 Hz, 1H), 3.37 (s, 3H), 3.32 (dd, J=14.4, 12.7 Hz, 1H), 3.26-3.15 (m, 2H), 2.86 (dd, J=14.3, 2.8 Hz, 1H), 2.51 (q, J=11.6 Hz, 1H), 2.04-1.92 (m, 2H), 1.77 (d, J=14.2 Hz, 1H), 1.73-1.56 (m, 21H). $^{13}$C NMR ($CDCl_3$, 151 MHz) δ 87.7 (d, J=171.4 Hz), 73.9 (d, J=27.6 Hz), 64.3, 57.2, 39.5, 35.3, 31.7 (d, J=20.5 Hz), 31.2. HRMS calcd for $C_9H_{15}FO_3S_2$ $[M+NH_4]^+$: 272.0785; found: 272.0789.

(±)-FMtcyDTDO2: $^1$H NMR ($CDCl_3$, 600 MHz) δ 4.72 (d, J=45.4 Hz, 1H), 3.61 (p, J=3.3 Hz, 1H), 3.38 (s, 3H), 3.33 (dd, J=14.4, 11.6 Hz, 1H), 3.25-3.14 (m, 2H), 2.87 (dd, J=14.3, 3.1 Hz, 1H), 2.50 (q, J=11.7 Hz, 1H), 1.98 (q, J=11.8 Hz, 1H), 1.91 (d, J=14.2 Hz, 1H), 1.8-1.79 (m, 1H), 1.72 (dt, J=45.3, 12.4 Hz, 1H), 1.54 (t, J=13.4 Hz, 1H). $^{13}$C NMR ($CDCl_3$, 151 MHz) δ 86.0 (d, J=172.5 Hz), 75.4 (d, J=27.6 Hz), 64.0, 57.3, 39.7, 35.7, 35.5, 32.8 (d, J=20.5 Hz), 30.2. HRMS calcd for $C_9H_{15}FO_3S_2$ $[M+NH_4]^+$: 272.0785; found: 272.0792.

Example 14—MTT Assay

Figure 7:
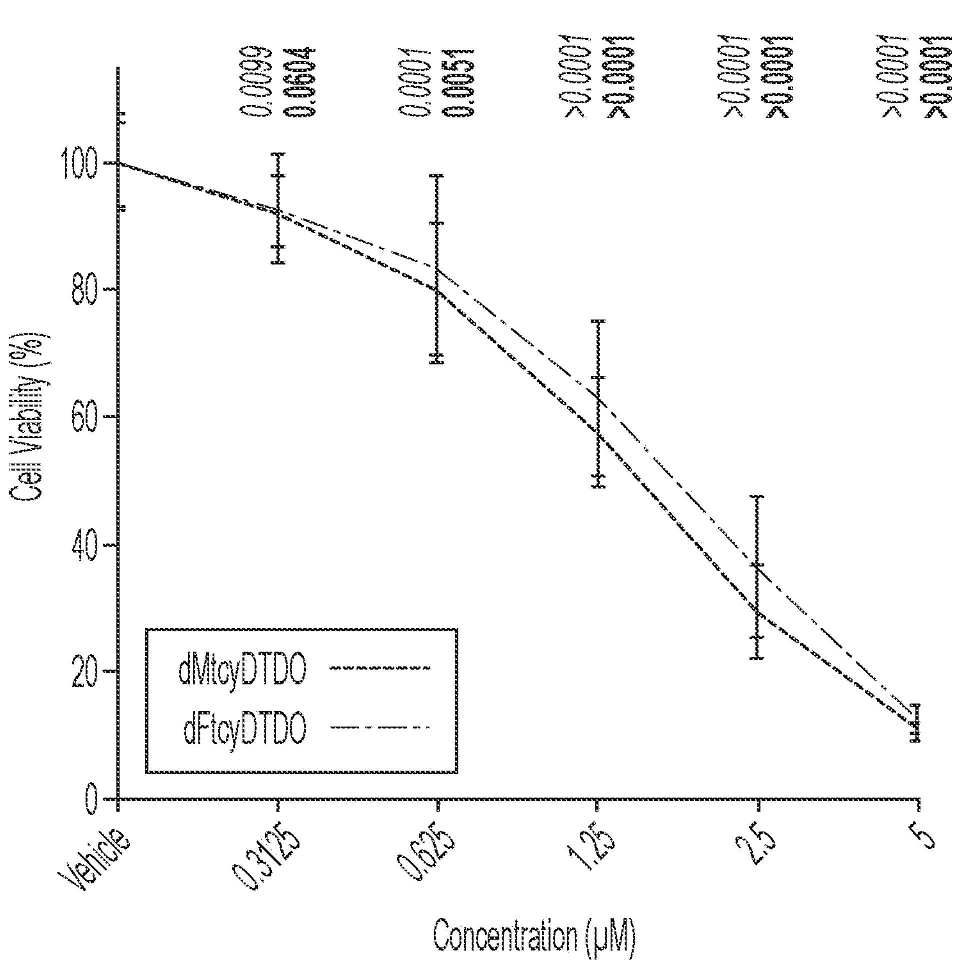
FIG. 7 is a graph depicting the effect of dMtcyDTO and dFtcyDTDO on cell viability of MDA-MB-468 cells. Increasing concentrations of the compounds decrease the viability of the cancer cell lines in a concentration-dependent manner. dMtcyDTDO and dFtcyDTDO exhibit similar cytotoxicity profiles against breast cancer cells and are 2-fold more potent than the previous most potent DDA, tcyDTDO.
Figure 8:
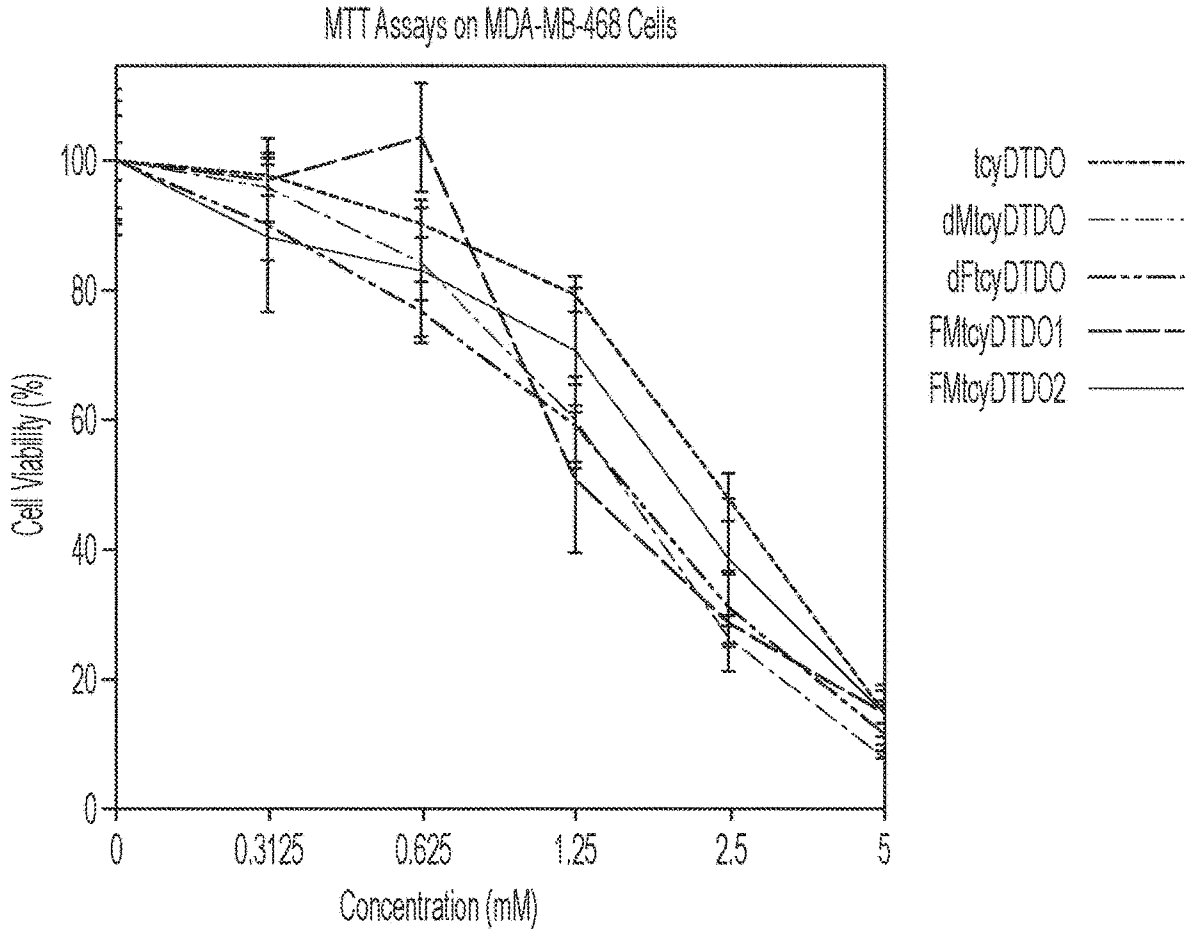
FIG. 8 is a graph comparing the effect of tcyDTO, dMtcyDTO, dFtcyDTDO, FMtcyDTDO1, and FMtcyDTDO2 on cell viability of MDA-MB-468 cells. Mono- and difluorinated tcyDTDO derivatives exhibit similar potencies of cancer cell cytotoxicity to dMtcyDTDO.
Figure 9:
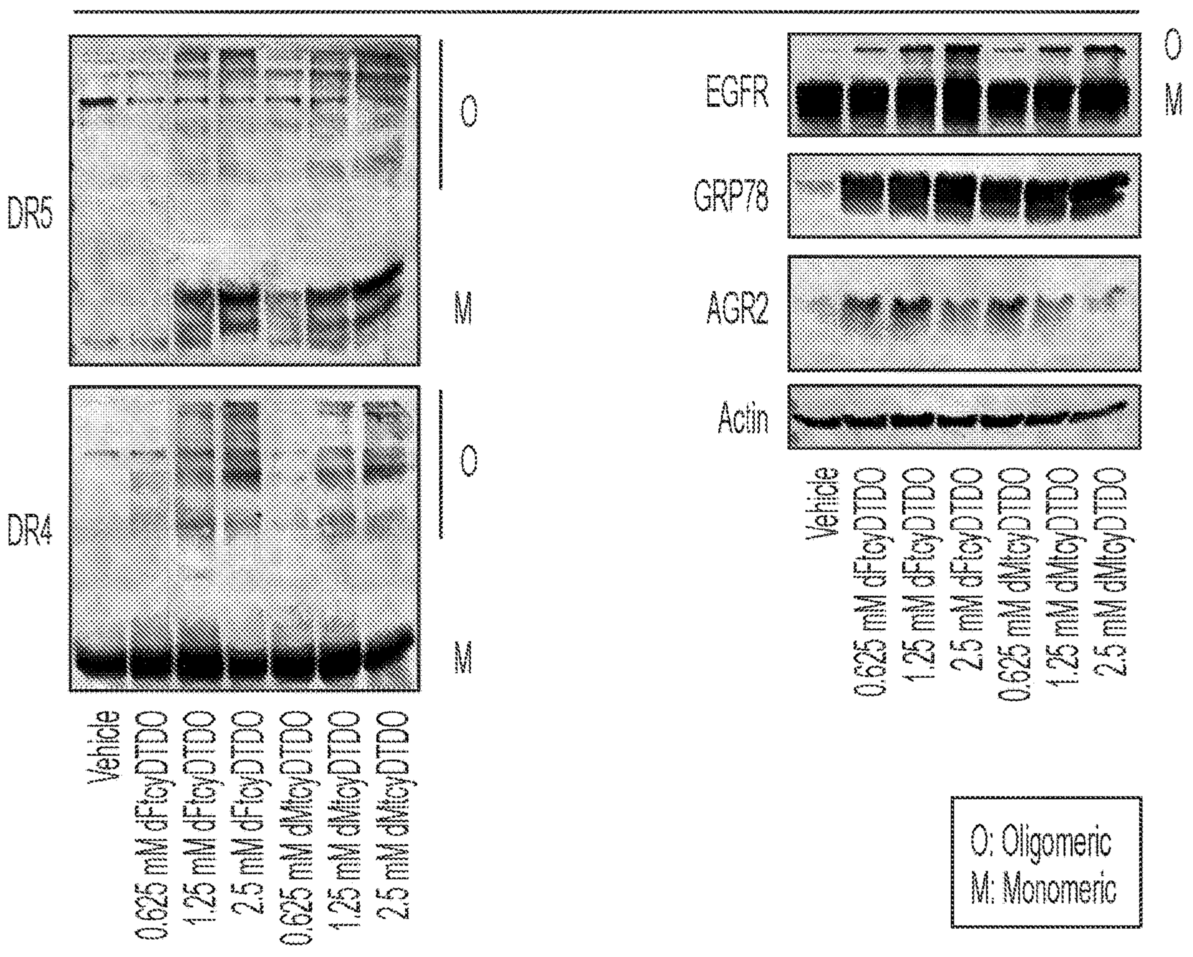
FIG. 9 is a series of immunoblots showing the effect of dMtcyDTDO and dFtcyDTDO at different concentrations in MDA-MB-468 cells. dMtcyDTDO and dFtcyDTDO induce disulfide bond-dependent oligomerization of DR4, DR5, and EGFR (0), upregulate DR5, and increase the ER-stress induced proteins GRP78 and AGR2 at the same concentrations at which these compounds induce cancer cell death.
Figure 10:
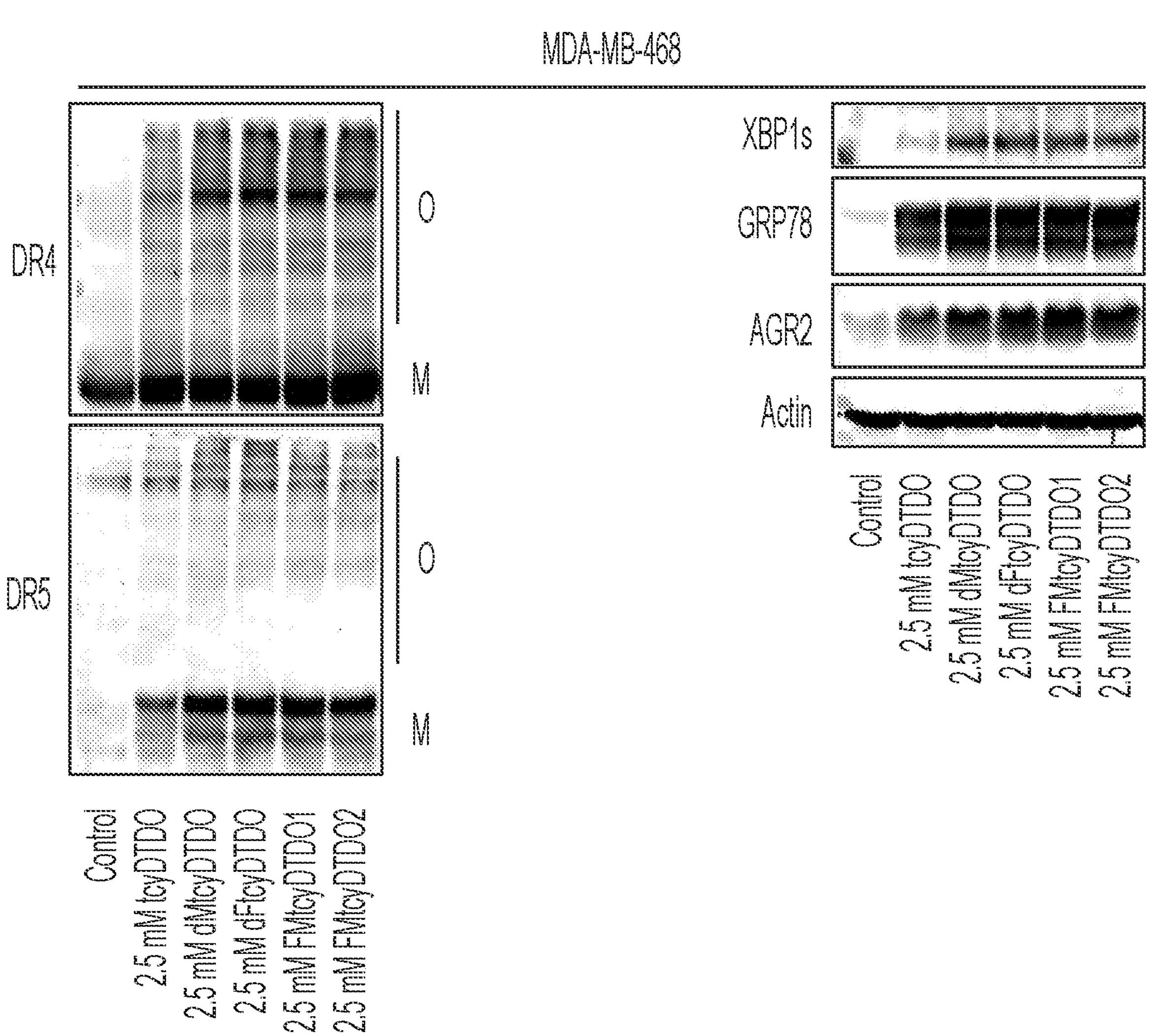
FIG. 10 is a series of immunoblots showing the effect of 2.5 mM tcyDTO, dMtcyDTO, dFtcyDTDO, FMtcyDTDO1, and FMtcyDTDO2 in MDA-MB-468 cells. dMtcyDTDO and dFtcyDTDO are more potent than tcyDTDO in upregulating and oligomerizing DR4 and DR5. and increasing the expression of the ER stress-induced proteins XBP1s, GRP78, and AGR2.

MTT cell viability is evaluated using MTT (3-(4,5-dimethylthiazol-2-yl)-2,5-diphenyltetrazolium bromide) assays carried out based on the manufacturer's instructions (kit CGD1, Sigma-Aldrich, St. Louis, MO). FIGS. 7 and 8 show that dMtcyDTDO and dFtcyDTDO exhibit similar cytotoxicity profiles against breast cancer cells and are 2-fold more potent than DDA and tcyDTDO.

Example 15—Protein Thiolate Reactivity Assay

To measure DDA and NSC322072 covalent binding to AGR2, purified, recombinant AGR2 is incubated with a biotin-tagged DDA compound for 1 h at 37° C. in the presence or absence of non-biotinylated competitor DDAs or NSC322072. Reaction mixtures are boiled with SDS-PAGE sample buffer supplemented with 100 mM N-ethylmaleimide for ca. 10 minutes to block free thiolate groups remaining after the reaction. Conjugation of AGR2 by DDAs is measured by evaluating AGR2 modification in the modified immunoblot assay in Example 16.

Example 16—Immunoblot Assays

Samples from the biotin-DDA/AGR2 reactions (Example 14) are resolved by non-reducing SDS-PAGE and transferred to nitrocellulose membranes. The membranes are blocked and analyzed by immunoblot with antibodies to AGR2 to verify addition of AGR2 protein to the assays. Anti-AGR2 primary antibody is detected with an Alkaline Phosphatase-conjugated secondary antibody. Separate, replicate membranes are probed with Streptavidin-Alkaline phosphatase. The Streptavidin-Alkaline phosphatase conjugate binds with high affinity to the AGR2 that is conjugated by biotin-DDA, but does not bind to unmodified AGR2. Both the AGR2 immunoblots and the Streptavidin-Alkaline phosphatase blots are detected using the standard Alkaline Phosphatase detection compounds, Bromo-chloro-indoyl Phosphate (BCIP)/Nitroblue Tetrazolium (NBT).

Embodiments of the Invention

1. A compound of Formula I, or salt thereof:

Formula I

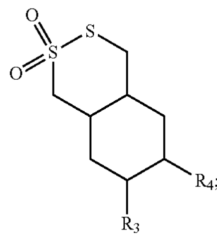

wherein, (iv) $R_3$ is halo or haloalkoxy; and $R_4$ is halo or haloalkoxy; or (v) $R_3$ is H or $C_1$-$C_6$ alkoxy; and $R_4$ is halo or haloalkoxy; or (vi) $R_3$ is halo or haloalkoxy; and $R_4$ is H or $C_1$-$C_6$ alkoxy.

2. A compound of embodiment 1, 12, 13, or 14, or a salt thereof:

wherein, $R_3$ is halo; and $R_4$ is halo.

3. A compound of embodiment 1, 12, 13, or 14, or a salt thereof:

wherein, $R_3$ is haloalkoxy; and $R_4$ is haloalkoxy.

4. The compound of embodiment 1, 12, 13, or 14, or salt thereof:

wherein, $R_3$ is haloalkoxy; and $R_4$ is halo.

5. The compound of embodiment 1, 12, 13, or 14, or salt thereof:

wherein, $R_3$ is halo; and $R_4$ is haloalkoxy.

6. The compound of embodiment 1, 12, 13, or 14, or salt thereof:

wherein, $R_3$ is H; and $R_4$ is halo.

7. The compound of embodiment 1, 12, 13, or 14, or salt thereof:

wherein, $R_3$ is H; and $R_4$ is haloalkoxy.

8. The compound of embodiment 1, 12, 13, or 14, or salt thereof:

wherein, $R_3$ is $C_1$-$C_6$ alkoxy; and $R_4$ is halo.

9. The compound of embodiment 1, 12, 13, or 14, or salt thereof:

wherein, $R_3$ is $C_1$-$C_6$ alkoxy; and $R_4$ is haloalkoxy.

10. The compound of embodiment 1, 12, 13, or 14, or salt thereof:

wherein, $R_3$ is halo or haloalkoxy; and $R_4$ is H.

11. The compound of embodiment 1, 12, 13, or 14, or salt thereof:

wherein, $R_3$ is halo or haloalkoxy; and $R_4$ is $C_1$-$C_6$ alkoxy.

12. The compound of embodiment 1, or a salt thereof, according to Formula (II):

Formula II

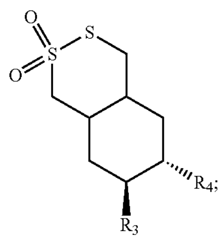

or salt thereof.

13. The compound of embodiment 1, or a salt thereof, according to Formula (III):

Formula III

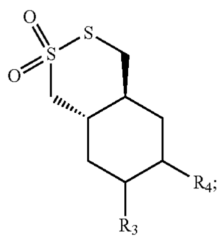

or salt thereof.

14. The compound of embodiment 1, or a salt thereof, according to any of Formula (IV-XI):

IV

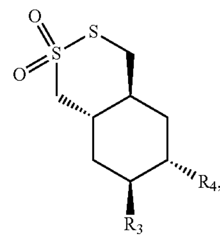

V

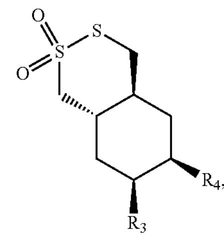

VI

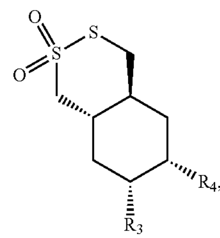

VII

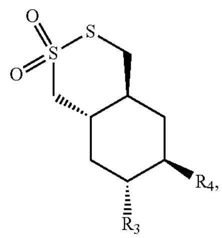

VIII

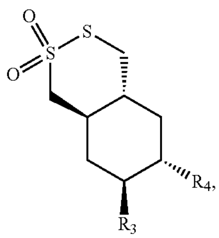

IX

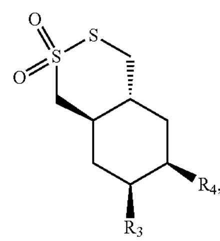

-continued

X

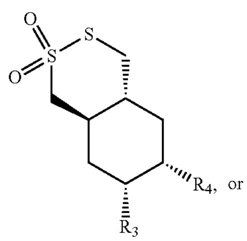

or

XI

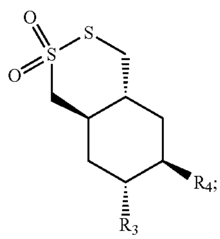

or salt thereof.

15. The compound or a salt thereof of embodiment 1, that is:

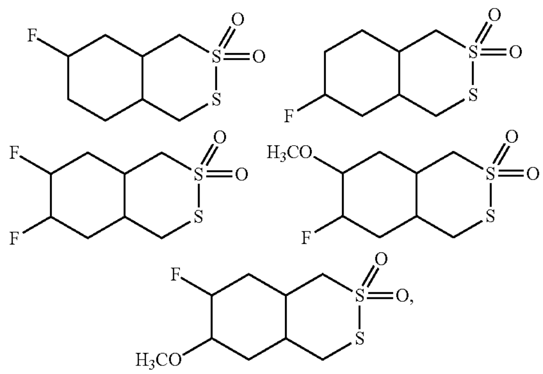

or a salt thereof.

16. The compound or a salt thereof of embodiment 1, that is:

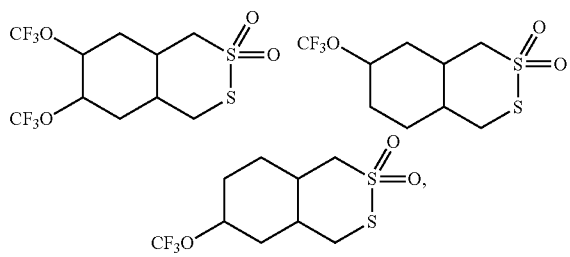

or a salt thereof.

17. The compound or a salt thereof of embodiment 1 that is any compound of Table 2, or salt thereof.

18. A pharmaceutical composition comprising a compound of any of embodiments 1-17, or salt thereof, and a pharmaceutically acceptable carrier.

19. The composition of embodiment 18, further comprising an additional therapeutic agent.

20. The composition of embodiment 19, wherein the additional therapeutic agent is an anti-cancer agent.

21. A method of inhibiting cell proliferation comprising administering to the subject in need thereof a therapeutically effective amount of: 1) a compound of any one of embodiments 1-17 or a salt thereof; or 2) a pharmaceutical composition of any one of embodiments 18-20.

22. The method of embodiment 21, wherein the cell is a cancer cell.

23. The method of embodiment 22, wherein the cancer cell is HER2 mediated.

24. The method of embodiment 23, wherein the cancer cell is a breast cancer cell.

25. The method of embodiment 24, wherein the breast cancer cell is a HER2-positive breast cancer cell.

26. The method of embodiment 25, wherein the breast cancer cell is modulated by HER2, HER3, and/or EGFR.

27. The method of embodiment 21, wherein the compound or salt thereof is a compound of salt thereof of embodiment 15.

28. The method of embodiment 21, wherein the compound or salt thereof is a compound of salt thereof of embodiment 16.

29. The method of embodiment 21, wherein the compound or salt thereof is a compound of salt thereof of embodiment 17.

30. A method of inhibiting cancer cell metastasis comprising administering to the subject in need thereof a therapeutically effective amount of: 1) a compound of any one of embodiments 1-17, or a salt thereof; or 2) a pharmaceutical composition of any one of embodiments 18-20.

31. A method of treating cancer in a subject comprising administering to the subject: 1) a compound of any one of embodiments 1-17, or a salt thereof; or 2) a pharmaceutical composition of any one of embodiments 18-20.

32. The method of embodiment 31, wherein the cancer is breast cancer, pancreatic cancer, prostate, oral, or non-small cell lung cancer (NSCLC).

33. A kit for treating a cell proliferative disorder, the kit comprising: 1) a compound of any one of embodiments 1-17, or a salt thereof; or 2) a pharmaceutical composition of any one of embodiments 18-20.

34. The method of embodiment 23, wherein the cancer cell is a pancreatic cancer cell.

REFERENCES CITED

1 Liu D, Rudland P S, Sibson D R, Platt-Higgins A, Barraclough R. Human homologue of cement gland protein, a novel metastasis inducer associated with breast carcinomas. *Cancer Res* 2005; 65: 3796-3805.

2 Zhang J S, Gong A, Cheville J C, Smith D I, Young C Y. AGR2, an androgen-inducible secretory protein overexpressed in prostate cancer. Genes Chromosomes *Cancer* 2005; 43: 249-259.

3 Fritzsche F R, Dahl E, Pahl S, Burkhardt M, Luo J, Mayordomo E et al. Prognostic relevance of AGR2 expression in breast cancer. *Clin Cancer Res* 2006; 12: 1728-1734.

4 Wang Z, Hao Y, Lowe A W. The adenocarcinoma-associated antigen, AGR2, promotes tumor growth, cell migration, and cellular transformation. *Cancer Res* 2008; 68: 492-497.

5 Hu Z, Gu Y, Han B, Zhang J, Li Z, Tian K et al. Knockdown of AGR2 induces cellular senescence in prostate cancer cells. *Carcinogenesis* 2012; 33: 1178-1186.

6 Brychtova V, Hermanova M, Karasek P, Lenz J, Selingerova I, Vojtesek B et al. Anterior gradient 2 and mucin 4 expression mirrors tumor cell differentiation in pancreatic adenocarcinomas, but aberrant anterior gradient 2 expression predicts worse patient outcome in poorly differentiated tumors. *Pancreas* 2014; 43: 75-81.

7 Di Maro G, Salerno P, Unger K, Orlandella F M, Monaco M, Chiappetta G et al. Anterior gradient protein 2 promotes survival, migration and invasion of papillary thyroid carcinoma cells. *Molecular Cancer* 2014; 13: 160.

8 Lacambra M D, Tsang J Y, Ni Y B, Chan S K, Tan P H, Tse G M. Anterior Gradient 2 is a Poor Outcome Indicator in Luminal Breast Cancer. *Ann Surg Oncol* 2015; 22: 3489-3496.

9 Dumartin L, Alrawashdeh W, Trabulo S M, Radon T P, Steiger K, Feakins R M et al. ER stress protein AGR2 precedes and is involved in the regulation of pancreatic cancer initiation. *Oncogene* 2017; 36: 3094-3103.

10 Innes H E, Liu D, Barraclough R, Davies M P, O'Neill P A, Platt-Higgins A et al. Significance of the metastasis-inducing protein AGR2 for outcome in hormonally treated breast cancer patients. *Br J Cancer* 2006; 94: 1057-1065.

11 Barraclough D L, Platt-Higgins A, de Silva Rudland S, Barraclough R, Winstanley J, West C R et al. The metastasis-associated anterior gradient 2 protein is correlated with poor survival of breast cancer patients. *Am J Pathol* 2009; 175: 1848-1857.

12 Negi H, Merugu S B, Mangukiya H B, Li Z, Zhou B, Sehar Q et al. Anterior Gradient-2 monoclonal antibody inhibits lung cancer growth and metastasis by upregulating p53 pathway and without exerting any toxicological effects: A preclinical study. *Cancer Lett* 2019; 449: 125-134.

13 Guo H, Chen H, Zhu Q, Yu X, Rong R, Merugu S B et al. A humanized monoclonal antibody targeting secreted anterior gradient 2 effectively inhibits the xenograft tumor growth. *Biochem Biophys Res Commun* 2016; 475: 57-63.

14 Liu A Y, Kanan A D, Radon T P, Shah S, Weeks M E, Foster J M et al. AGR2, a unique tumor-associated antigen, is a promising candidate for antibody targeting. *Oncotarget* 2019; 10: 4276-4289.

15 Dong A, Wodziak D, Lowe A W. Epidermal growth factor receptor (EGFR) signaling requires a specific endoplasmic reticulum thioredoxin for the post-translational control of receptor presentation to the cell surface. *J Biol Chem* 2015; 290: 8016-8027.

16 Narumi S, Miki Y, Hata S, Ebina M, Saito M, Mori K et al. Anterior gradient 2 is correlated with EGFR mutation in lung adenocarcinoma tissues. *Int J Biol Markers* 2015; 30: e234-242.

17 Tomoshige K, Guo M, Tsuchiya T, Fukazawa T, Fink-Baldauf I M, Stuart W D et al. An EGFR ligand promotes EGFR-mutant but not KRAS-mutant lung cancer in vivo. *Oncogene* 2018; 37: 3894-3908.

18 Ferreira R B, Law M E, Jahn S C, Davis B J, Heldermon C D, Reinhard M et al. Novel agents that downregulate EGFR, HER2, and HER3 in parallel. *Oncotarget* 2015; 6: 10445-10459.

19 Ferreira R B, Wang M, Law M E, Davis B J, Bartley A N, Higgins P J et al. Disulfide bond disrupting agents activate the unfolded protein response in EGFR- and HER2-positive breast tumor cells. *Oncotarget* 2017; 8: 28971-28989.

20 Besse L, Besse A, Mendez-Lopez M, Vasickova K, Sedlackova M, Vanhara P et al. A metabolic switch in proteasome inhibitor resistant multiple myeloma ensures higher mitochondrial metabolism, protein folding and sphingomyelin synthesis. *Haematologica* 2019.

21 Wang M, Ferreira R B, Law M E, Davis B J, Yaaghubi E, Ghilardi A F et al. A novel proteotoxic combination therapy for EGFR+ and HER2+ cancers. *Oncogene* 2019; 38: 4264-4282.

22 Wang M, Law M E, Davis B J, Yaaghubi E, Ghilardi A F, Ferreira R B et al. Disulfide bond-disrupting agents activate the tumor necrosis family-related apoptosis-inducing ligand/death receptor 5 pathway. *Cell Death Discov* 2019; 5: 153.

What is claimed is:

1. A compound of Formula I, or salt thereof:

Formula I

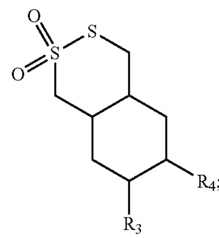

wherein, (i) $R_3$ is halo or haloalkoxy; and $R_4$ is halo or haloalkoxy; or (ii) $R_3$ is H or $C_1$-$C_6$ alkoxy; and $R_4$ is halo or haloalkoxy; or (iii) $R_3$ is halo or haloalkoxy; and $R_4$ is H or $C_1$-$C_6$ alkoxy.

2. The compound of claim 1, or a salt thereof: wherein, $R_3$ is halo; and $R_4$ is halo; or $R_3$ is halo; and $R_4$ is haloalkoxy.

3. The compound of claim 1, or a salt thereof: wherein, $R_3$ is haloalkoxy; and $R_4$ is haloalkoxy; or $R_3$ is haloalkoxy; and $R_4$ is halo.

4. The compound of claim 1, or salt thereof: wherein, $R_3$ is H; and $R_4$ is halo; or $R_3$ is H; and $R_4$ is haloalkoxy.

5. The compound of claim 1, or salt thereof: wherein, $R_3$ is $C_1$-$C_6$ alkoxy; and $R_4$ is halo; or $R_3$ is $C_1$-$C_6$ alkoxy; and $R_4$ is haloalkoxy.

6. The compound of claim 1, or salt thereof: wherein, $R_3$ is halo or haloalkoxy; and $R_4$ is H; or $R_3$ is halo or haloalkoxy; and $R_4$ is $C_1$-$C_6$ alkoxy.

7. The compound of claim 1, or a salt thereof, according to:

(a) Formula (II):

Formula II

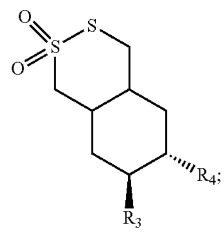

or salt thereof;
(b) Formula (III):
Formula III
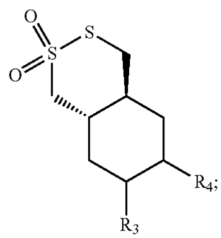
or salt thereof; or
(c) any of Formula (IV-XI):
IV
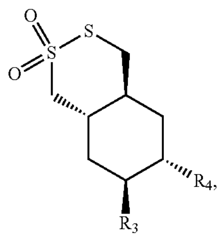
V
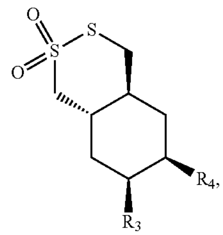
VI
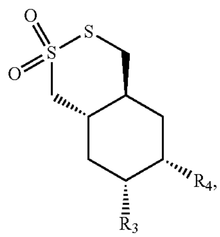
VII
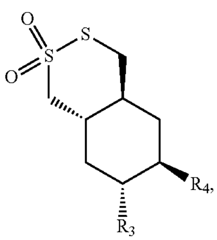
-continued
VIII
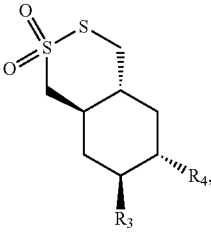
IX
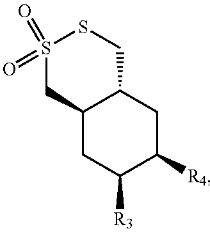
X
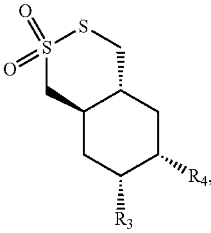
or
XI
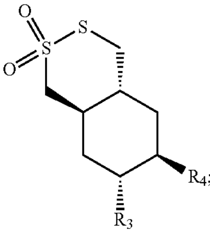
or salt thereof.
8. The compound or a salt thereof of claim 1, wherein the compound is of the formula:
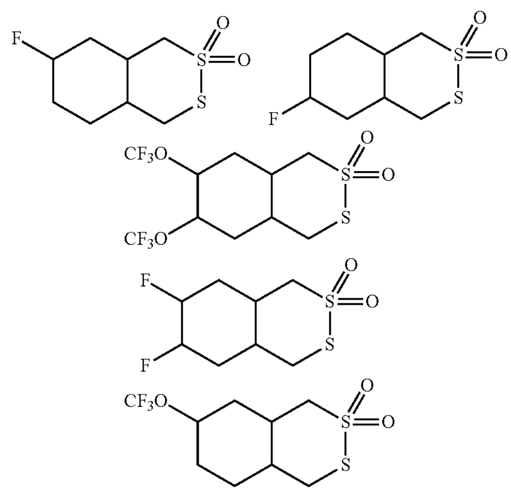

-continued

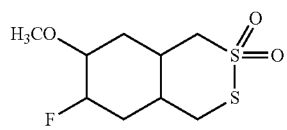

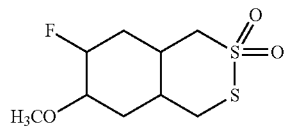

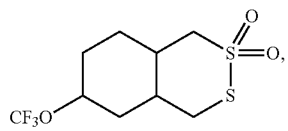

33

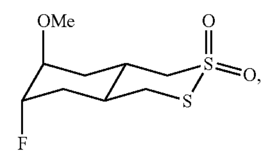

34

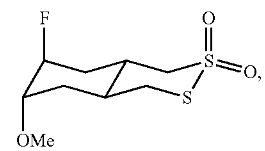

7

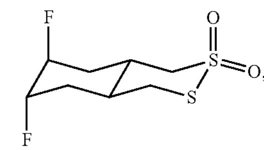

27

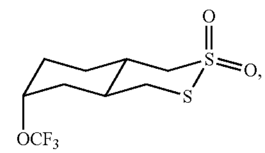

28

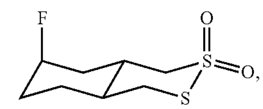

16

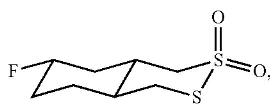

43

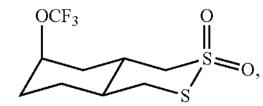

-continued

44

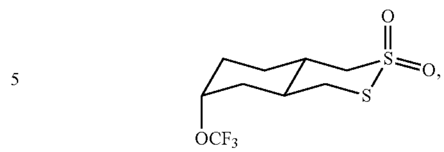

17

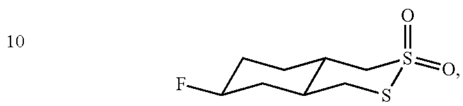

53

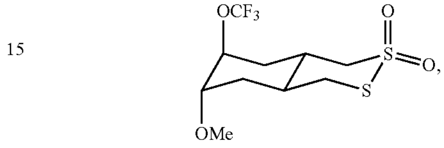

54

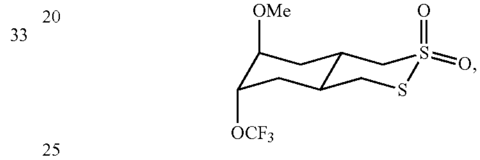

or salt thereof.

9. A pharmaceutical composition comprising a compound of claim 1, or salt thereof, and a pharmaceutically acceptable carrier.

10. The composition of claim 9, further comprising an additional therapeutic agent.

11. A method of inhibiting cell proliferation comprising administering to a subject in need thereof a therapeutically effective amount of a compound of claim 1, or salt thereof, wherein the cell proliferation is modulated by HER2, HER3, and/or EGFR.

12. The method of claim 11, wherein the cell is a cancer cell.

13. The method of claim 12, wherein the cancer cell proliferation is modulated by HER2 mediated.

14. The method of claim 12, wherein the cancer cell is a breast cancer cell.

15. The method of claim 14, wherein the breast cancer cell is a HER2-positive breast cancer cell.

16. The method of claim 14, wherein the breast cancer cell proliferation is modulated by EGFR.

17. A method of inhibiting cancer cell metastasis comprising administering to a subject in need thereof a therapeutically effective amount a compound of claim 1, or a salt thereof, wherein the cancer cell metastasis is modulated by HER2, HER3, and/or EGFR.

18. A method of treating cancer in a subject comprising administering to the subject a compound of claim 1, or a salt thereof, wherein the cancer is modulated by HER2, HER3, and/or EGFR.

19. The method of claim 18, wherein the cancer is breast cancer, pancreatic cancer, prostate, oral, or non-small cell lung cancer (NSCLC).

20. A kit for treating a cell proliferative disorder, the kit comprising a compound of claim 1, or a salt thereof.

* * * * *